US010271841B2

(12) United States Patent
Overmyer et al.

(10) Patent No.: US 10,271,841 B2
(45) Date of Patent: Apr. 30, 2019

(54) BAILOUT ASSEMBLY FOR SURGICAL STAPLER

(71) Applicant: Ethicon Endo-Surgery, LLC, Guaynabo, PR (US)

(72) Inventors: Mark D. Overmyer, Cincinnati, OH (US); Jason E. Zerkle, Blanchester, OH (US); Craig S. Smith, Cincinnati, OH (US); Kevin D. Sackett, Independence, KY (US); Emily A. Schellin, Cincinnati, OH (US); Kevin L. Houser, Springboro, OH (US); Charles J. Scheib, Loveland, OH (US); Frederick E. Shelton, IV, Hillsboro, OH (US)

(73) Assignee: Ethicon LLC, Guaynabo, PR (US)

( * ) Notice: Subject to any disclaimer, the term of this patent is extended or adjusted under 35 U.S.C. 154(b) by 686 days.

(21) Appl. No.: 14/751,426

(22) Filed: Jun. 26, 2015

(65) Prior Publication Data
US 2016/0374669 A1 Dec. 29, 2016

(51) Int. Cl.
*A61B 17/072* (2006.01)
*A61B 17/068* (2006.01)
(Continued)

(52) U.S. Cl.
CPC .......... *A61B 17/068* (2013.01); *A61B 17/105* (2013.01); *A61B 17/1155* (2013.01);
(Continued)

(58) Field of Classification Search
CPC . A61B 17/068; A61B 17/0684; A61B 17/072; A61B 17/07207; A61B 17/115;
(Continued)

(56) References Cited

U.S. PATENT DOCUMENTS 5,205,459 A 4/1993 Brinkerhoff et al.
5,271,544 A 12/1993 Fox et al.
(Continued)

FOREIGN PATENT DOCUMENTS

EP 2 792 308 A2 10/2014

OTHER PUBLICATIONS

European Search Report, Partial, dated Oct. 24, 2016 for Application No. EP 16176164.8, 7 pgs.
(Continued)

*Primary Examiner* — Scott A. Smith
(74) *Attorney, Agent, or Firm* — Frost Brown Todd LLC

(57) ABSTRACT

A surgical instrument includes an anvil, a staple applying assembly, an adjustment member, a user input feature, and a bailout assembly. The staple applying assembly includes a distal surface defining openings and a driver that is operable to drive an annular array of staples through the openings of the distal surface and into tissue. The adjustment member is operable to adjust the position of the anvil to thereby vary a gap distance defined between the anvil and the distal surface. The adjustment member includes a first section and a second section. The user input feature is operable to actuate the driver to thereby drive the staples. The bailout assembly is operable to selectively separate the first section of the adjustment member from the second section of the adjustment member.

20 Claims, 47 Drawing Sheets

(51) Int. Cl.
*A61B 17/115* (2006.01)
*A61B 17/10* (2006.01)
A61B 17/00 (2006.01)
A61B 90/00 (2016.01)

(52) U.S. Cl.
CPC ....... *A61B 17/072* (2013.01); *A61B 17/07207* (2013.01); *A61B 2017/00398* (2013.01); *A61B 2017/07214* (2013.01); *A61B 2090/08021* (2016.02)

(58) Field of Classification Search
CPC ........... A61B 2017/07214; A61B 2017/00398; A61B 17/105; A61B 17/1155
USPC .............. 227/19, 175.1, 175.2, 176.1, 180.1; 606/139, 153, 219
See application file for complete search history.

(56) References Cited

U.S. PATENT DOCUMENTS

| | | | |
|---|---|---|---|
| 5,275,322 A | 1/1994 | Wolf et al. | |
| 5,285,945 A | 2/1994 | Brinkerhoff et al. | |
| 5,292,053 A | 3/1994 | Smith et al. | |
| 5,333,773 A | 8/1994 | Main et al. | |
| 5,350,104 A | 9/1994 | Main et al. | |
| 5,452,836 A * | 9/1995 | Huitema | A61B 17/072 |
| | | | 227/176.1 |
| 5,533,661 A | 7/1996 | Main et al. | |
| 5,632,432 A * | 5/1997 | Schulze | A61B 17/07207 |
| | | | 227/176.1 |
| 5,797,537 A * | 8/1998 | Oberlin | A61B 17/07207 |
| | | | 227/176.1 |
| 6,945,444 B2 | 9/2005 | Gresham et al. | |
| 7,794,475 B2 | 9/2010 | Hess et al. | |
| 8,408,439 B2 | 4/2013 | Huang et al. | |
| 8,453,914 B2 | 6/2013 | Laurent et al. | |
| 8,910,847 B2 | 12/2014 | Nalagatla et al. | |
| 9,161,803 B2 | 10/2015 | Yates et al. | |
| 2014/0144968 A1 | 5/2014 | Shelton | |
| 2014/0144969 A1 | 5/2014 | Scheib et al. | |
| 2014/0151429 A1 | 6/2014 | Scheib et al. | |
| 2014/0151430 A1 | 6/2014 | Scheib et al. | |
| 2014/0158747 A1 | 6/2014 | Measamer et al. | |
| 2014/0166717 A1 | 6/2014 | Swayze et al. | |
| 2014/0166718 A1 | 6/2014 | Swayze et al. | |
| 2014/0166728 A1 | 6/2014 | Swayze et al. | |
| 2014/0305991 A1 * | 10/2014 | Parihar | A61B 17/072 |
| | | | 227/176.1 |
| 2015/0083772 A1 | 3/2015 | Miller et al. | |
| 2015/0083773 A1 | 3/2015 | Measamer et al. | |
| 2015/0083774 A1 | 3/2015 | Measamer et al. | |
| 2015/0083775 A1 | 3/2015 | Leimbach et al. | |

OTHER PUBLICATIONS

European Search Report and Written Opinion dated Apr. 12, 2017 for Application No. EP 16176164.8, 10 pgs.
European Communication, Intention to Grant, dated Jun. 19, 2018 for Application No. EP 16176164.8, 116 pgs.
International Search Report and Written Opinion dated Feb. 9, 2017 for Application No. PCT/US2016/038879, 17 pgs.

* cited by examiner

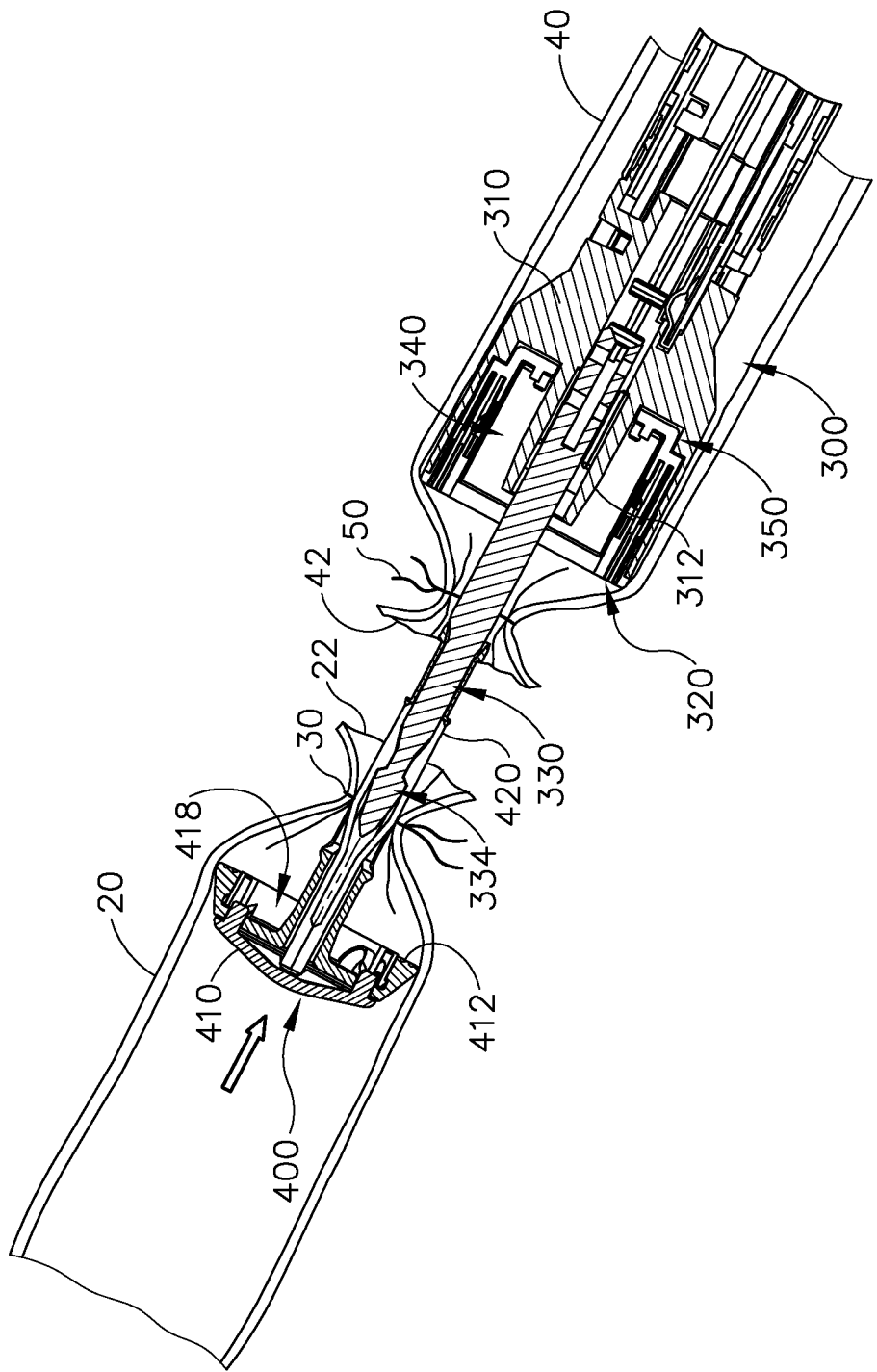

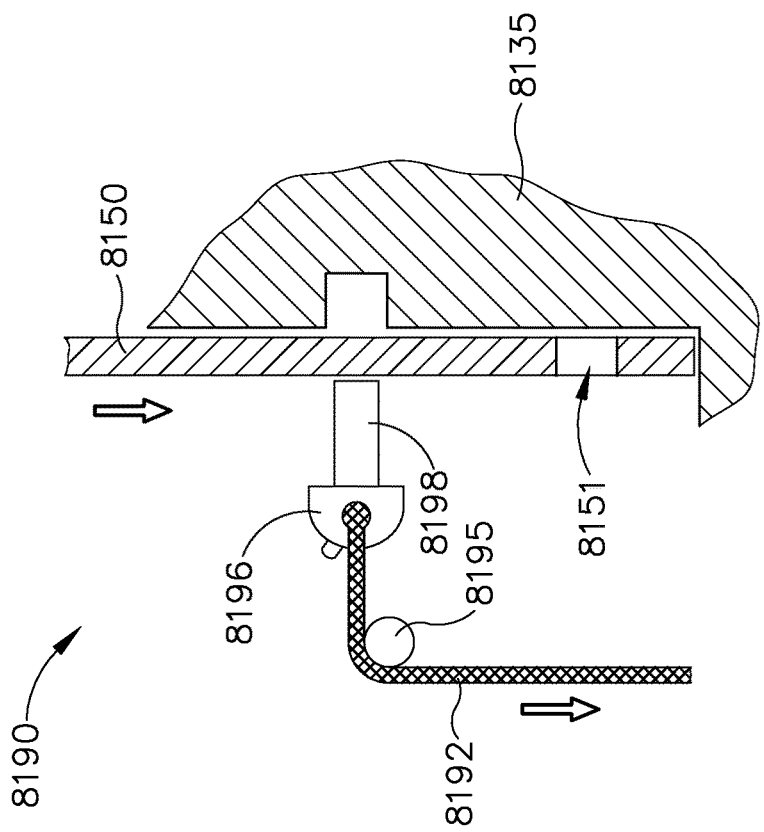
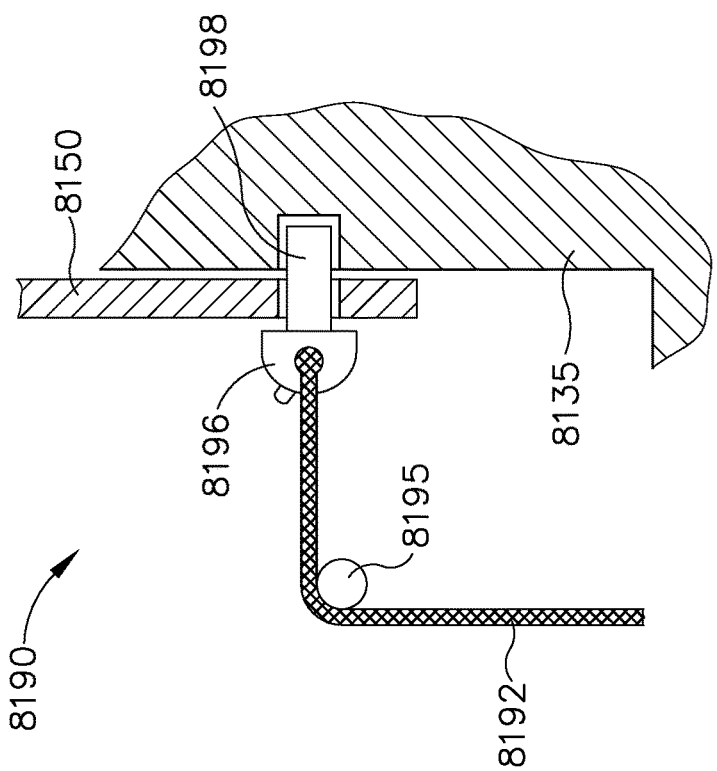

BAILOUT ASSEMBLY FOR SURGICAL STAPLER

BACKGROUND

In some surgical procedures (e.g., colorectal, bariatric, thoracic, etc.), portions of a patient's digestive tract (e.g., the gastrointestinal tract and/or esophagus, etc.) may be cut and removed to eliminate undesirable tissue or for other reasons. Once the tissue is removed, the remaining portions of the digestive tract may be coupled together in an end-to-end anastomosis. The end-to-end anastomosis may provide a substantially unobstructed flow path from one portion of the digestive tract to the other portion of the digestive tract, without also providing any kind of leaking at the site of the anastomosis.

One example of an instrument that may be used to provide an end-to-end anastomosis is a circular stapler. Some such staplers are operable to clamp down on layers of tissue, cut through the clamped layers of tissue, and drive staples through the clamped layers of tissue to substantially seal the layers of tissue together near the severed ends of the tissue layers, thereby joining the two severed ends of the anatomical lumen together. The circular stapler may be configured to sever the tissue and seal the tissue substantially simultaneously. For instance, the circular stapler may sever excess tissue that is interior to an annular array of staples at an anastomosis, to provide a substantially smooth transition between the anatomical lumen sections that are joined at the anastomosis. Circular staplers may be used in open procedures or in endoscopic procedures. In some instances, a portion of the circular stapler is inserted through a patient's naturally occurring orifice.

Examples of circular staplers are described in U.S. Pat. No. 5,205,459, entitled "Surgical Anastomosis Stapling Instrument," issued Apr. 27, 1993; U.S. Pat. No. 5,271,544, entitled "Surgical Anastomosis Stapling Instrument," issued Dec. 21, 1993; U.S. Pat. No. 5,275,322, entitled "Surgical Anastomosis Stapling Instrument," issued Jan. 4, 1994; U.S. Pat. No. 5,285,945, entitled "Surgical Anastomosis Stapling Instrument," issued Feb. 15, 1994; U.S. Pat. No. 5,292,053, entitled "Surgical Anastomosis Stapling Instrument," issued Mar. 8, 1994; U.S. Pat. No. 5,333,773, entitled "Surgical Anastomosis Stapling Instrument," issued Aug. 2, 1994; U.S. Pat. No. 5,350,104, entitled "Surgical Anastomosis Stapling Instrument," issued Sep. 27, 1994; and U.S. Pat. No. 5,533,661, entitled "Surgical Anastomosis Stapling Instrument," issued Jul. 9, 1996; and U.S. Pat. No. 8,910,847, entitled "Low Cost Anvil Assembly for a Circular Stapler," issued Dec. 16, 2014. The disclosure of each of the above-cited U.S. Patents is incorporated by reference herein.

Some circular staplers may include a motorized actuation mechanism. Examples of circular staplers with motorized actuation mechanisms are described in U.S. Pub. No. 2015/0083772, entitled "Surgical Stapler with Rotary Cam Drive and Return," published Mar. 26, 2015, now abandoned; U.S. Pub. No. 2015/0083773, entitled "Surgical Stapling Instrument with Drive Assembly Having Toggle Features," published Mar. 26, 2015, issued as U.S. Pat. No. 9,907,552 on Mar. 6, 2018; U.S. Pub. No. 2015/0083774, entitled "Control Features for Motorized Surgical Stapling Instrument," published Mar. 26, 2015; and U.S. Pub. No. 2015/0083775, entitled "Surgical Stapler with Rotary Cam Drive," published Mar. 26, 2015, issued as U.S. Pat. No. 9,713,469 on July 25, 2017. The disclosure of each of the above-cited U.S. Patent Publications is incorporated by reference herein.

While various kinds of surgical stapling instruments and associated components have been made and used, it is believed that no one prior to the inventor(s) has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 21B depicts a cross-sectional side view of the anvil of FIG. 3 positioned within the first section of the digestive tract and the stapling head assembly of FIG. 6 positioned in the second section of the digestive tract, with the anvil secured to the stapling head assembly;

FIG. 35 depicts a detailed side cross-sectional view of the knife bailout assembly of FIG. 34, the knife bailout assembly in a neutral position;

FIG. 36 depicts another detailed side cross-sectional view of the knife bailout assembly of FIG. 34, the knife bailout assembly in a released position;

Figure 1:
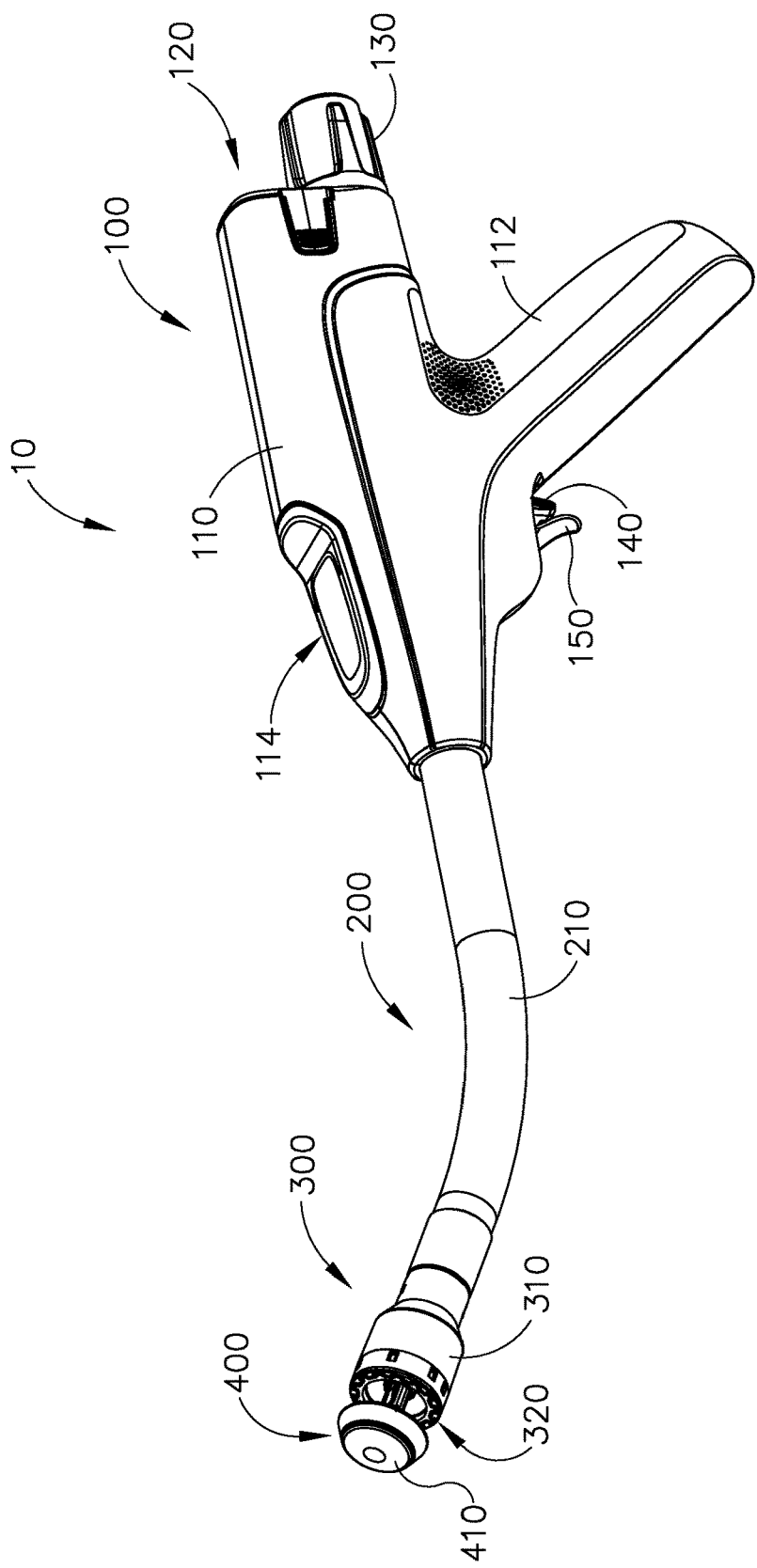
FIG. 1 depicts a perspective view of an exemplary circular stapler.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. Overview of Exemplary Circular Stapling Surgical Instrument

Figure 2:
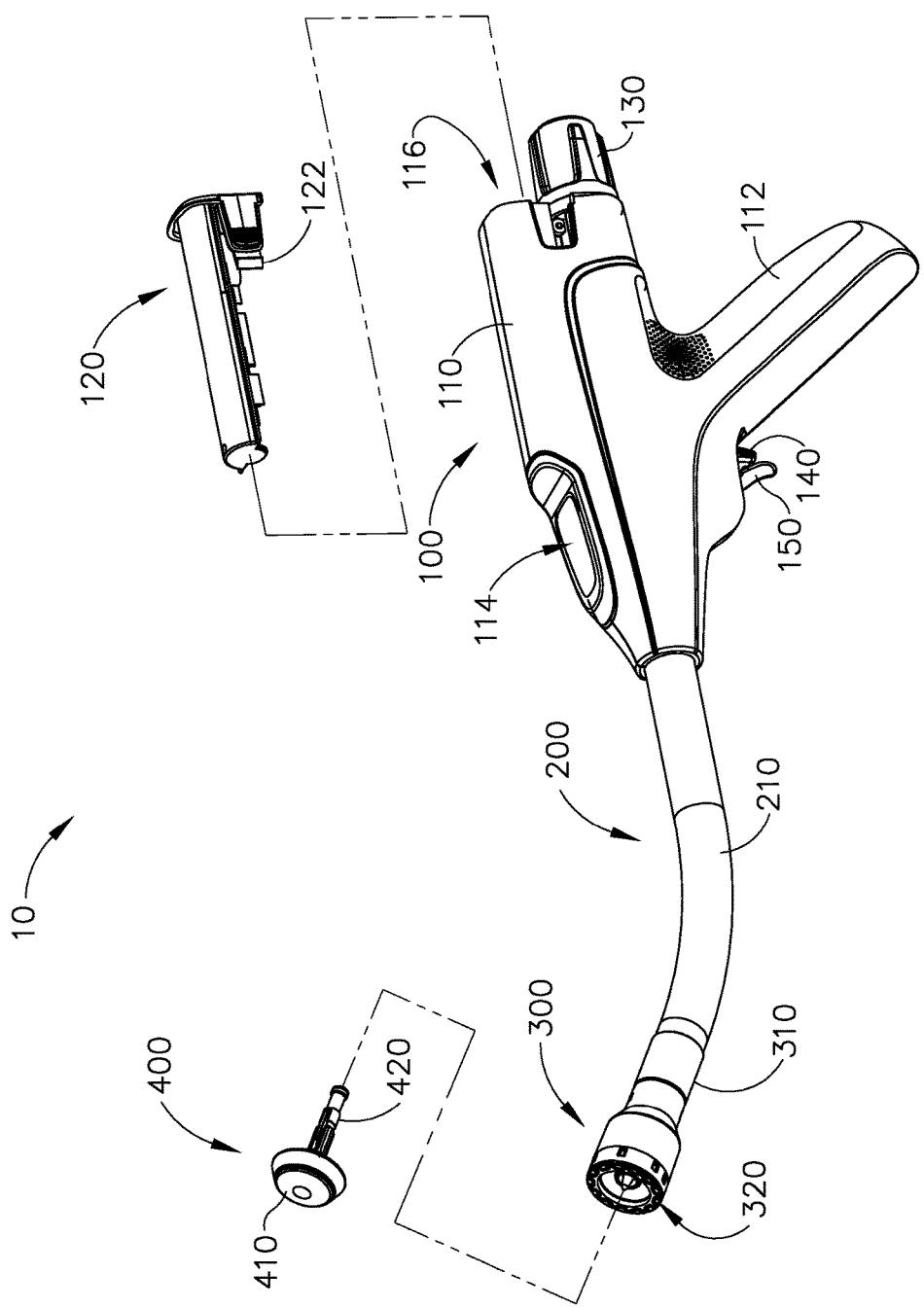
FIG. 2 depicts a perspective view of the circular stapler of FIG. 1, with a battery pack removed from a handle assembly and an anvil removed from a stapling head assembly.

FIGS. 1-2 depict an exemplary surgical circular stapling instrument (10) that may be used to provide an end-to-end anastomosis between two sections of an anatomical lumen such as a portion of a patient's digestive tract. Instrument (10) of this example comprises a handle assembly (100), a shaft assembly (200), a stapling head assembly (300), and an anvil (400). Handle assembly (100) comprises a casing (110) defining an obliquely oriented pistol grip (112). In some versions, pistol grip (112) is perpendicularly oriented. In some other versions, pistol grip (112) is omitted. Handle assembly (110) further includes a window (114) that permits viewing of a movable indicator needle (526) as will be described in greater detail below. In some versions, a series of hash marks, colored regions, and/or other fixed indicators are positioned adjacent to window (114) in order to provide a visual context for indicator needle (526), thereby facilitating operator evaluation of the position of needle (526) within window (114). Various suitable alternative features and configurations for handle assembly (112) will be apparent to those of ordinary skill in the art in view of the teachings herein.

Instrument (10) of the present example further includes a battery pack (120). Battery pack (120) is operable to provide electrical power to a motor (160) in pistol grip (112) as will be described in greater detail below. Battery pack (120) is removable from handle assembly (100). In particular, as shown in FIGS. 1-2, battery pack (120) may be inserted into a socket (116) defined by casing (110). Once battery pack (120) is fully inserted in socket (116), latches (122) of battery pack (120) may resiliently engage interior features of casing (110) to provide a snap fit. To remove battery pack (120), the operator may press latches (122) inwardly to disengage latches (122) from the interior features of casing (110) then pull battery pack (120) proximally from socket (116). It should be understood that battery pack (120) and handle assembly (100) may have complementary electrical contacts, pins and sockets, and/or other features that provide paths for electrical communication from battery pack (120) to electrically powered components in handle assembly (100) when battery pack (120) is inserted in socket (116). It should also be understood that, in some versions, battery pack (120) is unitarily incorporated within handle assembly (100) such that battery back (120) cannot be removed from handle assembly (100).

Shaft assembly (200) extends distally from handle assembly (100) and includes a preformed bend. In some versions, the preformed bend is configured to facilitate positioning of stapling head assembly (300) within a patient's colon. Various suitable bend angles or radii that may be used will be apparent to those of ordinary skill in the art in view of the teachings herein. In some other versions, shaft assembly (200) is straight, such that shaft assembly (200) lacks a preformed bend. Various exemplary components that may be incorporated into shaft assembly (100) will be described in greater detail below.

Stapling head assembly (300) is located at the distal end of shaft assembly (200). As shown in FIGS. 1-2 and as will be described in greater detail below, anvil (400) is configured to removably couple with shaft assembly (200), adjacent to stapling head assembly (300). As will also be described in greater detail below, anvil (400) and stapling head assembly (300) are configured to cooperate to manipulate tissue in three ways, including clamping the tissue, cutting the tissue, and stapling the tissue. A knob (130) at the proximal end of handle assembly (100) is rotatable relative to casing (110) to provide precise clamping of the tissue between anvil (400) and stapling head assembly (300). When a safety trigger (140) of handle assembly (100) is pivoted away from a firing trigger (150) of handle assembly (100), firing trigger (150) may be actuated to thereby provide cutting and stapling of the tissue.

A. Exemplary Anvil

In the following discussion of anvil (400), the terms "distal" and "proximal" (and variations thereof) will be used with reference to the orientation of anvil (400) when anvil (400) is coupled with shaft assembly (200) of instrument (10). Thus, proximal features of anvil (400) will be closer to the operator of instrument (10); while distal features of anvil (400) will be further from the operator of instrument (10).

Figure 3:
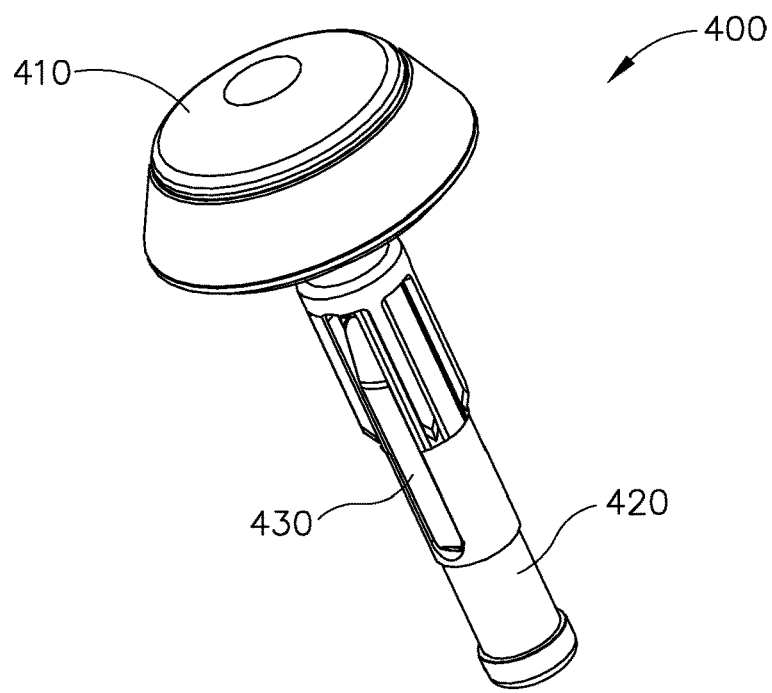
FIG. 3 depicts a perspective view of the anvil of the circular stapler of FIG. 1.
Figure 4:
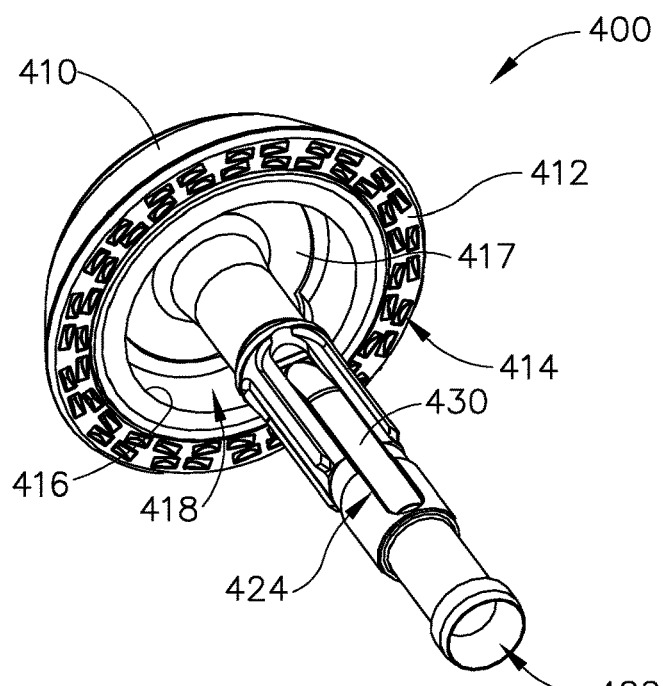
FIG. 4 depicts another perspective view of the anvil of FIG. 3.
Figure 5:
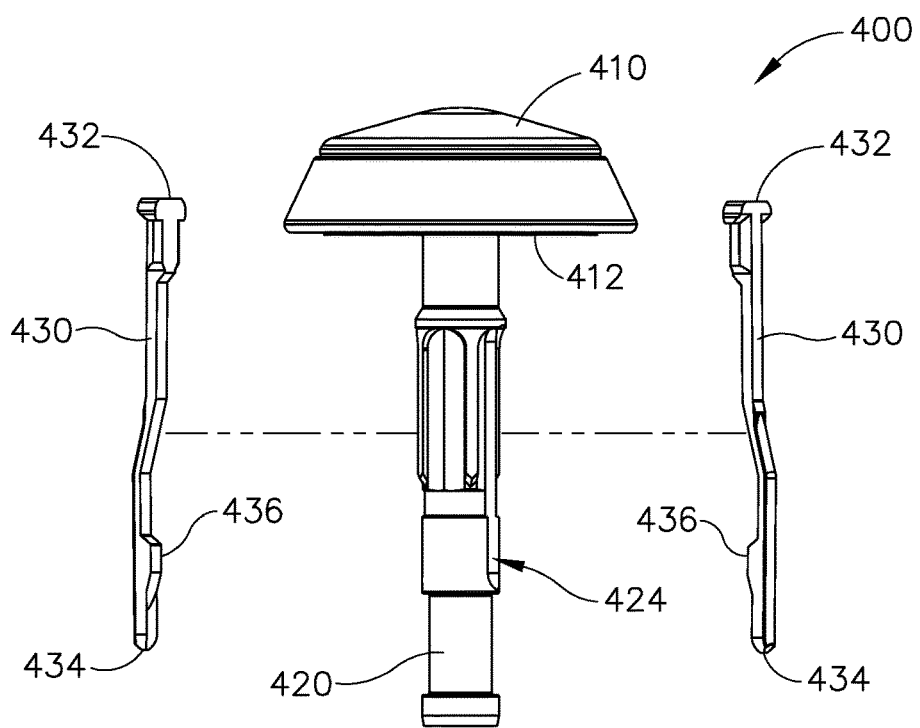
FIG. 5 depicts an exploded side elevational view of the anvil of FIG. 3.

As best seen in FIGS. 3-5, anvil (400) of the present example comprises a head (410) and a shank (420). Head (410) includes a proximal surface (412) that defines a plurality of staple forming pockets (414). Staple forming pockets (414) are arranged in two concentric annular arrays. In some other versions, staple forming pockets (414) are arranged in three or more concentric annular arrays. Staple forming pockets (414) are configured to deform staples as the staples are driven into staple forming pockets (414). For instance, each staple forming pocket (414) may deform a generally "U" shaped staple into a "B" shape as is known in the art. As best seen in FIG. 4, proximal surface (412) terminates at an inner edge (416), which defines an outer boundary of an annular recess (418) surrounding shank (420).

Shank (420) defines a bore (422) and includes a pair of pivoting latch members (430) positioned in bore (422). As best seen in FIG. 5, each latch member (430) includes a "T" shaped distal end (432), a rounded proximal end (434), and a latch shelf (436) located distal to proximal end (434). "T" shaped distal ends (432) secure latch members (430) within bore (422). Latch members (430) are positioned within bore (422) such that distal ends (434) are positioned at the proximal ends of lateral openings (424), which are formed through the sidewall of shank (420). Lateral openings (424) thus provide clearance for distal ends (434) and latch shelves (436) to deflect radially outwardly from the longitudinal axis defined by shank (420). However, latch members (430) are configured to resiliently bias distal ends (434) and latch shelves (436) to radially inwardly toward the longitudinal axis defined by shank (420). Latch members (430) thus act as retaining clips. This allows anvil (400) to be removably secured to a trocar (330) of stapling head assembly (300) as will be described in greater detail below. It should be understood, however, that latch members (436) are merely optional. Anvil (400) may be removably secured to a trocar (330) using any other suitable components, features, or techniques.

In addition to or in lieu of the foregoing, anvil (400) may be further constructed and operable in accordance with at least some of the teachings of U.S. Pat. Nos. 5,205,459; 5,271,544; 5,275,322; 5,285,945; 5,292,053; 5,333,773; 5,350,104; 5,533,661; and/or U.S. Pat. No. 8,910,847, the disclosures of which are incorporated by reference herein. Still other suitable configurations will be apparent to one of ordinary skill in the art in view of the teachings herein.

B. Exemplary Stapling Head Assembly

Figure 6:
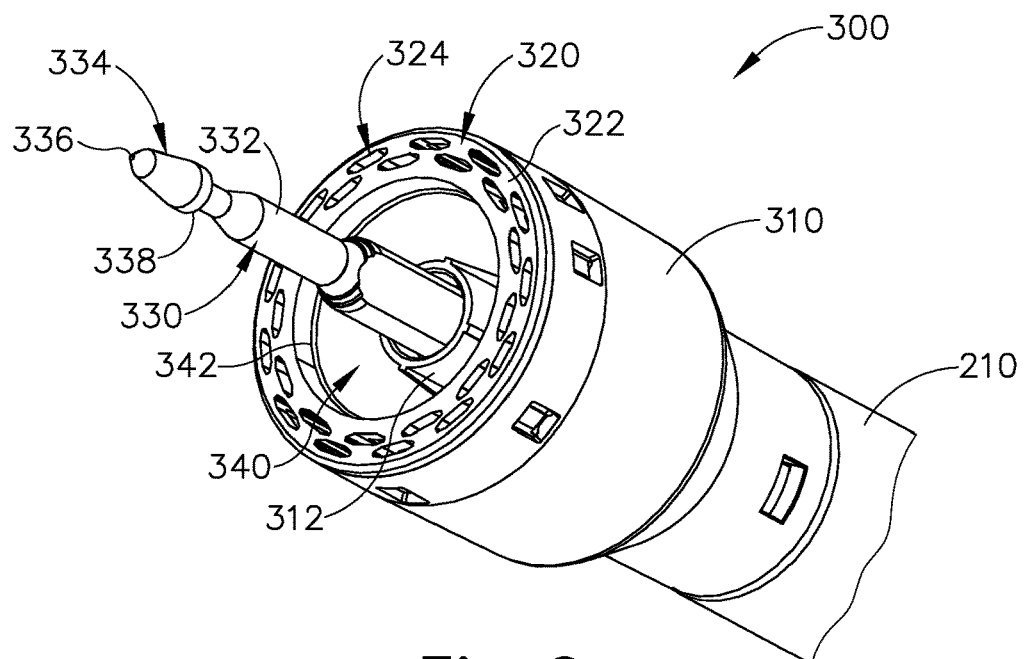
FIG. 6 depicts a perspective view of the stapling head assembly of the circular stapler of FIG. 1.
Figure 7:
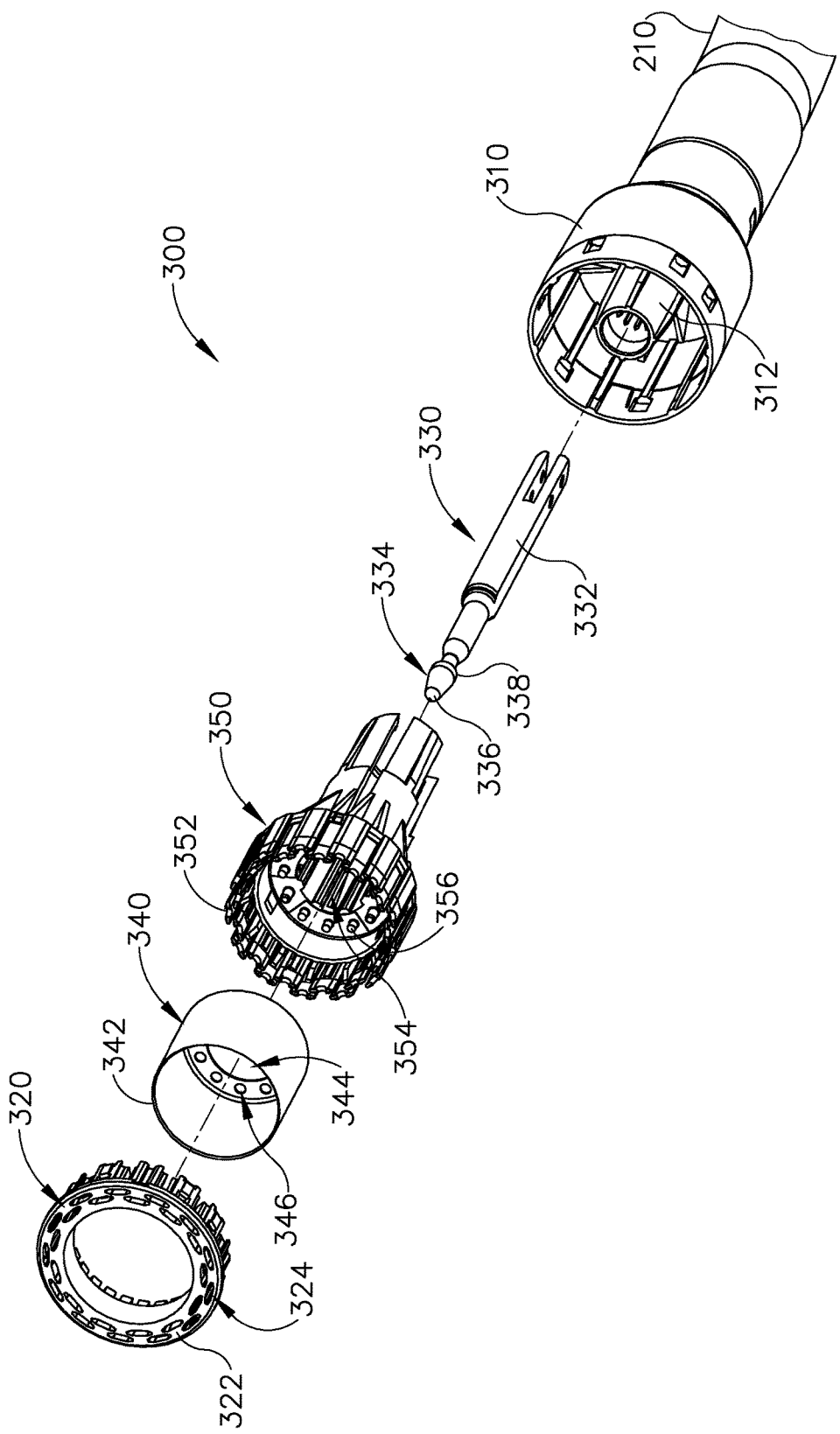
FIG. 7 depicts an exploded perspective view of the stapling head assembly of FIG. 6.

As best seen in FIGS. 6-7, stapling head assembly (300) of the present example is coupled to a distal end of shaft assembly (200) and comprises a tubular casing (310) housing a slidable staple driver member (350). A cylindraceous inner core member (312) extends distally within tubular casing (310). Tubular casing (310) is fixedly secured to an outer sheath (210) of shaft assembly (200), such that tubular casing (310) serves as a mechanical ground for stapling head assembly (300).

Trocar (330) is positioned coaxially within inner core member (312) of tubular casing (310). As will be described in greater detail below, trocar (330) is operable to translate distally and proximally relative to tubular casing (310) in response to rotation of knob (130) relative to casing (110) of handle assembly (100). Trocar (330) comprises a shaft (332) and a head (334). Head (334) includes a pointed tip (336) and an inwardly extending proximal surface (338). Shaft (332) thus provides a reduced outer diameter just proximal to head (334), with surface (338) providing a transition between that reduced outer diameter of shaft (332) and the outer diameter of head (334). While tip (336) is pointed in the present example, tip (336) is not sharp. Tip (336) will thus not easily cause trauma to tissue due to inadvertent contact with tissue. Head (334) and the distal portion of shaft (332) are configured for insertion in bore (422) of anvil (420). Proximal surface (338) and latch shelves (436) have complementary positions and configurations such that latch shelves (436) engage proximal surface (338) when shank (420) of anvil (400) is fully seated on trocar (330). Anvil (400) is thus secured to trocar (330) through a snap fit due to latch members (430).

Staple driver member (350) is operable to actuate longitudinally within tubular casing (310) in response to activation of motor (160) as will be described in greater detail below. Staple driver member (350) includes two distally presented concentric annular arrays of staple drivers (352). Staple drivers (352) are arranged to correspond with the arrangement of staple forming pockets (414) described above. Thus, each staple driver (352) is configured to drive a corresponding staple into a corresponding staple forming pocket (414) when stapling head assembly (300) is actuated. It should be understood that the arrangement of staple drivers (352) may be modified just like the arrangement of staple forming pockets (414) as described above. Staple driver member (350) also defines a bore (354) that is configured to coaxially receive core member (312) of tubular casing (310). An annular array of studs (356) project distally from a distally presented surface surrounding bore (354).

A cylindraceous knife member (340) is coaxially positioned within staple driver member (350). Knife member (340) includes a distally presented, sharp circular cutting edge (342). Knife member (340) is sized such that knife member (340) defines an outer diameter that is smaller than the diameter defined by the inner annular array of staple drivers (352). Knife member (340) also defines an opening that is configured to coaxially receive core member (312) of tubular casing (310). An annular array of openings (346) formed in knife member (340) is configured to complement the annular array of studs (356) of staple driver member (350), such that knife member (340) is fixedly secured to staple driver member (350) via studs (356) and openings (346). Other suitable structural relationships between knife member (340) and stapler driver member (350) will be apparent to those of ordinary skill in the art in view of the teachings herein.

A deck member (320) is fixedly secured to tubular casing (310). Deck member (320) includes a distally presented deck surface (322) defining two concentric annular arrays of staple openings (324). Staple openings (324) are arranged to correspond with the arrangement of staple drivers (352) and staple forming pockets (414) described above. Thus, each staple opening (324) is configured to provide a path for a corresponding staple driver (352) to drive a corresponding staple through deck member (320) and into a corresponding staple forming pocket (414) when stapling head assembly (300) is actuated. It should be understood that the arrangement of staple openings (322) may be modified just like the arrangement of staple forming pockets (414) as described above. It should also be understood that various structures and techniques may be used to contain staples within stapling head assembly (300) before stapling head assembly (300) is actuated. Such structures and techniques that are used to contain staples within stapling head assembly (300) may prevent the staples from inadvertently falling out through staple openings (324) before stapling head assembly (300) is actuated. Various suitable forms that such structures and techniques may take will be apparent to those of ordinary skill in the art in view of the teachings herein.

As best seen in FIG. 6, deck member (320) defines an inner diameter that is just slightly larger than the outer diameter defined by knife member (340). Deck member (320) is thus configured to allow knife member (340) to translate distally to a point where cutting edge (342) is distal to deck surface (322).

In addition to or in lieu of the foregoing, stapling head assembly (300) may be further constructed and operable in accordance with at least some of the teachings of U.S. Pat. Nos. 5,205,459; 5,271,544; 5,275,322; 5,285,945; 5,292,053; 5,333,773; 5,350,104; 5,533,661; and/or U.S. Pat. No. 8,910,847, the disclosures of which are incorporated by reference herein. Still other suitable configurations will be apparent to one of ordinary skill in the art in view of the teachings herein.

C. Exemplary Shaft Assembly

Figure 8:
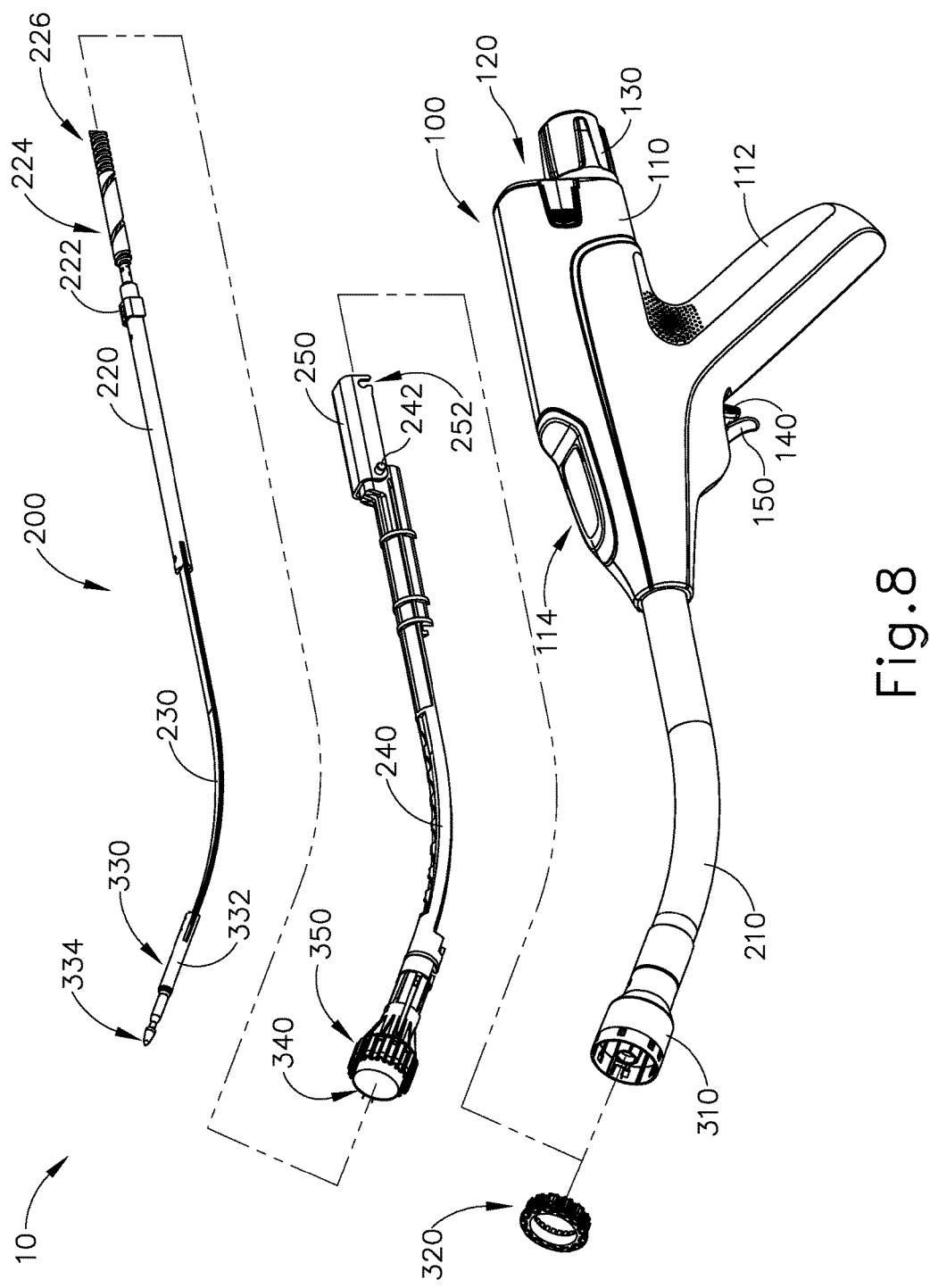
FIG. 8 depicts an exploded perspective view of the circular stapler of FIG. 1, with portions of the shaft assembly shown separately from each other.

FIG. 8 shows various components of shaft assembly (200), which couples components of stapling head assembly (300) with components of handle assembly (100). In particular, and as noted above, shaft assembly (200) includes an outer sheath (210) that extends between handle assembly (100) and tubular casing (310). In the present example, outer sheath (210) is rigid and includes a preformed curved section as noted above.

Shaft assembly (200) further includes a trocar actuation rod (220) and a trocar actuation band assembly (230). The distal end of trocar actuation band assembly (230) is fixedly secured to the proximal end of trocar shaft (332). The proximal end of trocar actuation band assembly (230) is fixedly secured to the distal end of trocar actuation rod (220). It should therefore be understood that trocar (330) will translate longitudinally relative to outer sheath (210) in response to translation of trocar actuation band assembly (230) and trocar actuation rod (220) relative to outer sheath (210). Trocar actuation band assembly (230) is configured to flex such that trocar actuation band assembly (230) may follow along the preformed curve in shaft assembly (200) as trocar actuation band assembly (230) is translated longitudinally relative to outer sheath (210). However, trocar actuation band assembly (230) has sufficient column strength and tensile strength to transfer distal and proximal forces from trocar actuation rod (220) to trocar shaft (332). Trocar actuation rod (220) is rigid. A clip (222) is fixedly secured to trocar actuation rod (220) and is configured to cooperate with complementary features within handle assembly (100) to prevent trocar actuation rod (220) from rotating within handle assembly (100) while still permitting trocar actuation rod (220) to translate longitudinally within handle assembly (100). Trocar actuation rod (220) further includes a coarse helical threading (224) and a fine helical threading (226). Details regarding the movement of trocar actuation rod (220) will be described in greater detail below.

Shaft assembly (200) further includes a stapling head assembly driver (240) that is slidably received within outer sheath (210). The distal end of stapling head assembly driver (240) is fixedly secured to the proximal end of staple driver member (350). The proximal end of stapling head assembly driver (240) is secured to a drive bracket (250) via a pin (242). It should therefore be understood that staple driver member (350) will translate longitudinally relative to outer sheath (210) in response to translation of stapling head assembly driver (240) and drive bracket (250) relative to outer sheath (210). Stapling head assembly driver (240) is configured to flex such that stapling head assembly driver (240) may follow along the preformed curve in shaft assembly (200) as stapling head assembly driver (240) is translated longitudinally relative to outer sheath (210). However, stapling head assembly driver (240) has sufficient column strength to transfer distal forces from drive bracket (250) to staple driver member (350). Details regarding the movement of drive bracket (250) will be described in greater detail below.

While not shown in FIG. 8, it should be understood that shaft assembly (200) may further include one or more spacer elements within outer sheath (210). Such spacer elements may be configured to support trocar actuation band assembly (230) and/or stapling head assembly driver (240) as trocar actuation band assembly (230) and/or stapling head assembly driver (240) translate through outer sheath (210). For instance, such spacer elements may prevent trocar actuation band assembly (230) and/or stapling head assembly driver (240) from buckling as trocar actuation band assembly (230) and/or stapling head assembly driver (240) translate through outer sheath (210). Various suitable forms that such spacer elements may take will be apparent to those of ordinary skill in the art in view of the teachings herein.

In addition to or in lieu of the foregoing, shaft assembly (200) may be further constructed and operable in accordance with at least some of the teachings of U.S. Pat. No. 5,205,459; 5,271,544; 5,275,322; 5,285,945; 5,292,053; 5,333,773; 5,350,104; 5,533,661; and/or U.S. Pat. No. 8,910,847, the disclosures of which are incorporated by reference herein. Still other suitable configurations will be apparent to one of ordinary skill in the art in view of the teachings herein.

D. Exemplary Actuator Handle Assembly

Figure 9:
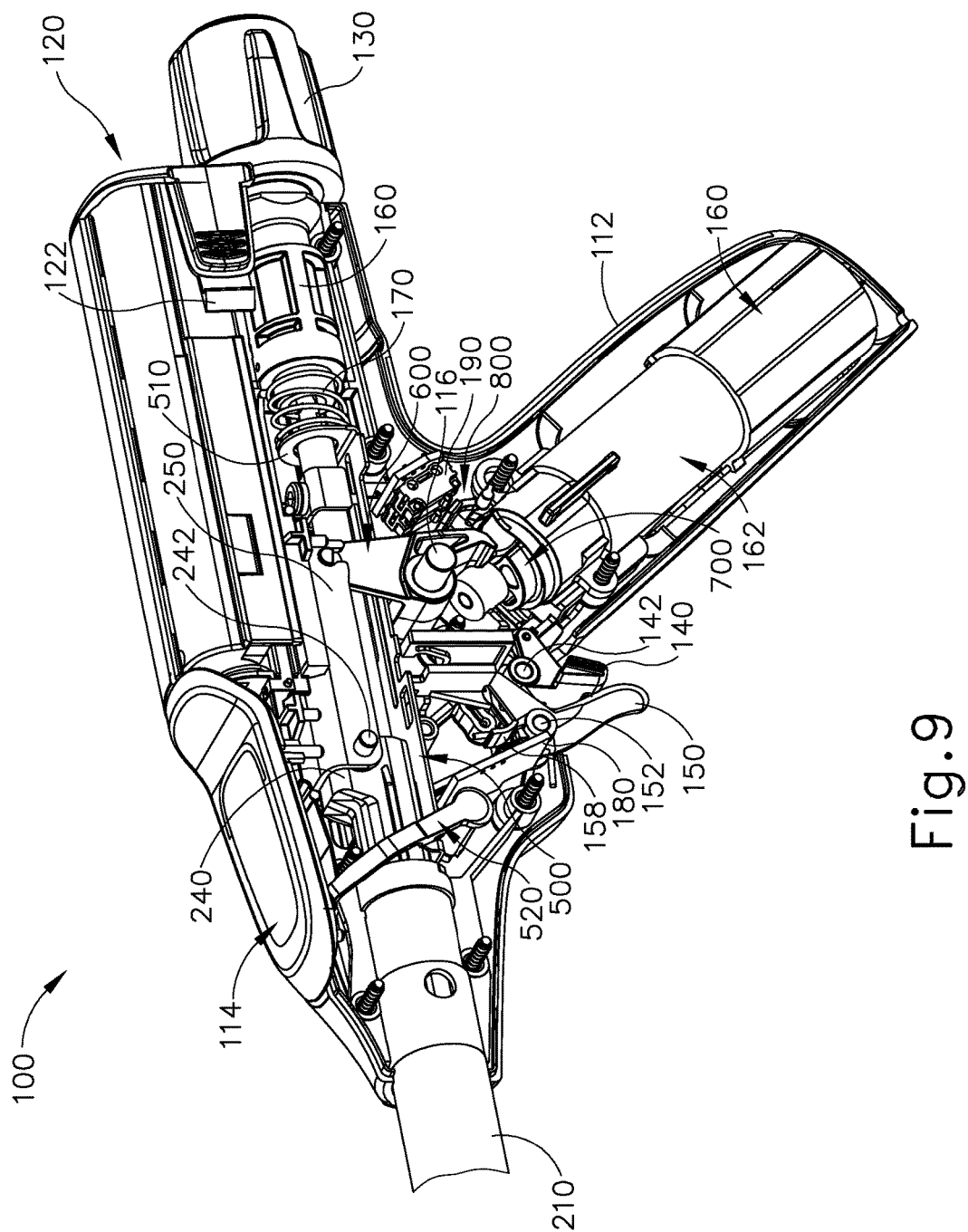
FIG. 9 depicts a perspective view of the handle assembly of the circular stapler of FIG. 1, with a housing half omitted to reveal internal components of the handle assembly.

As shown in FIG. 9, handle assembly (100) includes several components that are operable to actuate anvil (400) and stapling head assembly (300). Handle assembly (100) also includes components that are operable to selectively lock out triggers (140, 150) based on the position of anvil (400) relative to stapling head assembly (300). When triggers (140, 150) are locked out, firing trigger (150) is prevented from initiating actuation of stapling head assembly (300). Thus, trigger (150) is only operable to initiate actuation of stapling head assembly (300) when the position of anvil (400) relative to stapling head assembly (300) is within a predefined range. The components of handle assembly (100) that provide the foregoing operability will be described in greater detail below.

1 Exemplary Anvil Actuation Assembly

Knob (130) protrudes proximally from casing (110) of handle assembly and is rotatable relative to casing (110). As shown in FIG. 9, a nut (160) is secured to the distal end of knob (130). In the present example, nut (160) is fixedly secured to the distal end of knob (130) such that nut (160) will rotate unitarily with knob (130). Nut (160) and knob (130) are configured to cooperate with trocar actuation rod (220) to thereby translate trocar actuation rod (220) longitudinally relative to casing (110) in response to rotation of nut (160) and knob (130) relative to casing (110). As noted above, trocar (330) will translate longitudinally relative to outer sheath (210) in response to translation of trocar actuation rod (220) relative to outer sheath (210) and casing (110).

The proximal portion of trocar actuation rod (220) is positioned within handle assembly (100) to engage nut (160) and knob (130). In particular, trocar actuation rod (220) is positioned within handle assembly (100) such that coarse helical threading (224) will selectively engage a thread engagement feature (not shown) within the interior of nut (160); and such that fine helical threading (226) will selectively engage a thread engagement feature (not shown) within the interior of knob (130). In some versions, the thread engagement feature of nut (160) comprises an inwardly directed tab; while the thread engagement feature of knob (130) comprises a helical threading. Other suitable forms that such thread engagement features may take will be apparent to those of ordinary skill in the art in view of the teachings herein.

In the present example, when nut (160) and knob (130) are rotated relative to casing (110), trocar actuation rod (220) travels proximally through a first range of longitudinal motion where coarse helical threading (224) is engaged with nut (160) to provide a relatively rapid rate of translation. Fine helical threading (226) is not engaged with knob (130) during this range of motion. When nut (160) and knob (130) are further rotated relative to casing (110) after trocar actuation rod (220) completes the first range of motion, trocar actuation rod (220) will continue to travel proximally through a second range of longitudinal motion where fine helical threading (226) is engaged with knob (130) to provide a relatively slow rate of translation. Thus, trocar actuation rod (220) will translate proximally through a sequence of rapid translation followed by slow translation, based on engagement between coarse helical threading (224) and nut (160) followed by engagement between fine helical threading (226) and knob (130).

It should be understood that when anvil (400) is coupled with trocar (330), rotation of knob (130) will provide corresponding translation of anvil relative to stapling head assembly (300). It should also be understood that knob (130) may be rotated in a first angular direction (e.g., clockwise) to retract anvil (400) toward stapling head assembly (300); and in a second angular direction (e.g., counterclockwise) to advance anvil (400) away from stapling head assembly (300). Knob (130) may thus be used to adjust the gap distance (d) between opposing surfaces (412, 322) of anvil (400) and stapling head assembly (300) until a suitable gap distance (d) has been achieved as shown in FIG. 21C and as described in greater detail below.

2. Exemplary Trigger Lockout Assembly

As noted above, knob may be used to adjust the gap distance (d) between opposing surfaces (412, 322) of anvil (400) and stapling head assembly (300). Setting an appropriate gap distance (d) before actuating stapling head assembly (300) may be critical to the success of an anastomosis. For instance, if the gap distance (d) is too great, the staples that are deployed at the anastomosis site may not be sufficiently formed by staple forming pockets (414). This may result in leakage at the anastomosis site, and in some cases may ultimately lead to the separation of the anatomical lumen sections that are joined at the anastomosis site. If the gap distance (d) is too small, the internal structure of the tissue compressed between surfaces (412, 322) may be damaged to the point where the structural integrity of the tissue is compromised. This may prevent the tissue from adequately holding the formed staples, which again may result in leakage or other failure of the anastomosis. It may therefore be desirable to provide the operator with some form of feedback indicating whether the gap distance (d) is within an appropriate range. It may also be desirable to prevent the operator from actuating stapling head assembly (300) unless the gap distance (d) is within an appropriate range.

Figure 10:
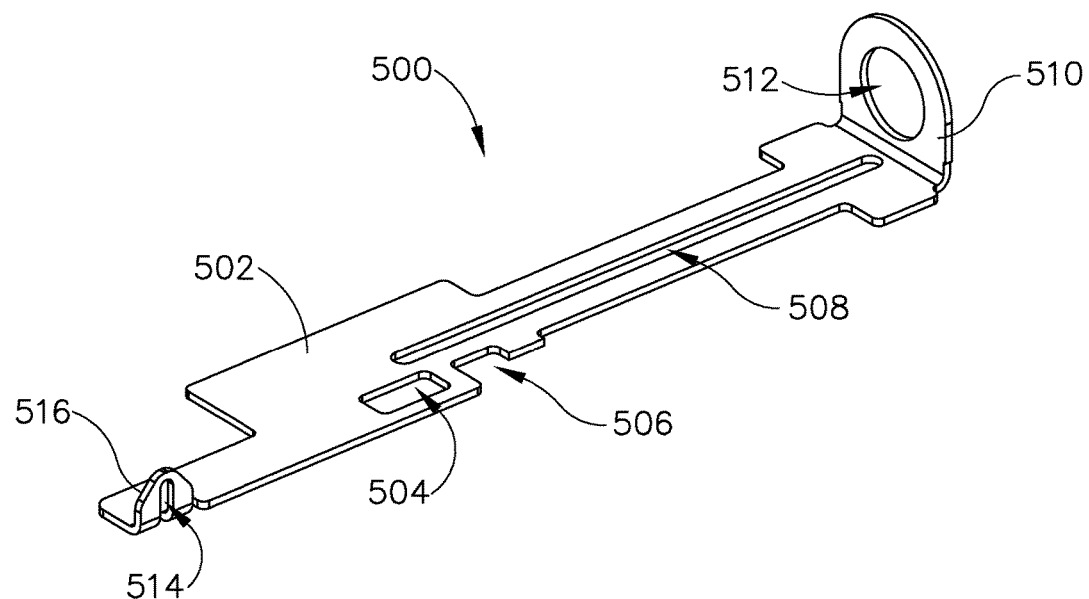
FIG. 10 depicts a perspective view of a bracket of the handle assembly of FIG. 9.

FIGS. 9-12E show components that provide feedback to the operator to indicate whether the gap distance (d) is within an appropriate range; and prevent the operator from actuating stapling head assembly (300) unless the gap distance (d) is within an appropriate range. As best seen in FIGS. 12B-12C, a bracket (500) is configured and positioned to move in response to movement of trocar actuation rod (220). As best seen in FIG. 10, bracket (500) includes a rigid body (502) that defines a first slot (504), a second slot (506), and a third slot (508). An upright feature (510) is positioned at the proximal end of body (502) and defines an opening (512). Trocar actuation rod (220) extends coaxially through opening (512). As shown in FIG. 9, a coil spring (170) is interposed between the proximal end of upright feature (510) and a rigid bulkhead feature that is defined by casing (110) and that forms a support journal for nut (160). The bulkhead is fixed within casing (110) and thereby provides a ground for the proximal end of coil spring (170), such that coil spring (170) resiliently imparts a distal bias to bracket (500) via upright feature (510). Bracket (500) further includes a laterally presented flange (516) at the distal end of body (502). Flange (516) defines a slot (514).

Figure 11:
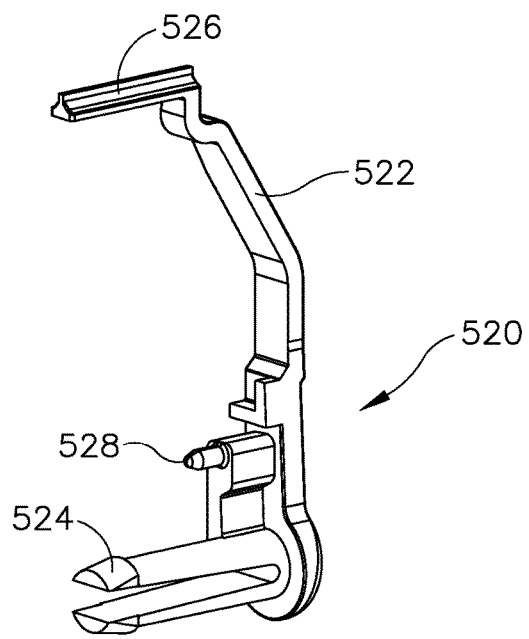
FIG. 11 depicts a perspective view of an indicator member of the handle assembly of FIG. 9.
Figure 12A:
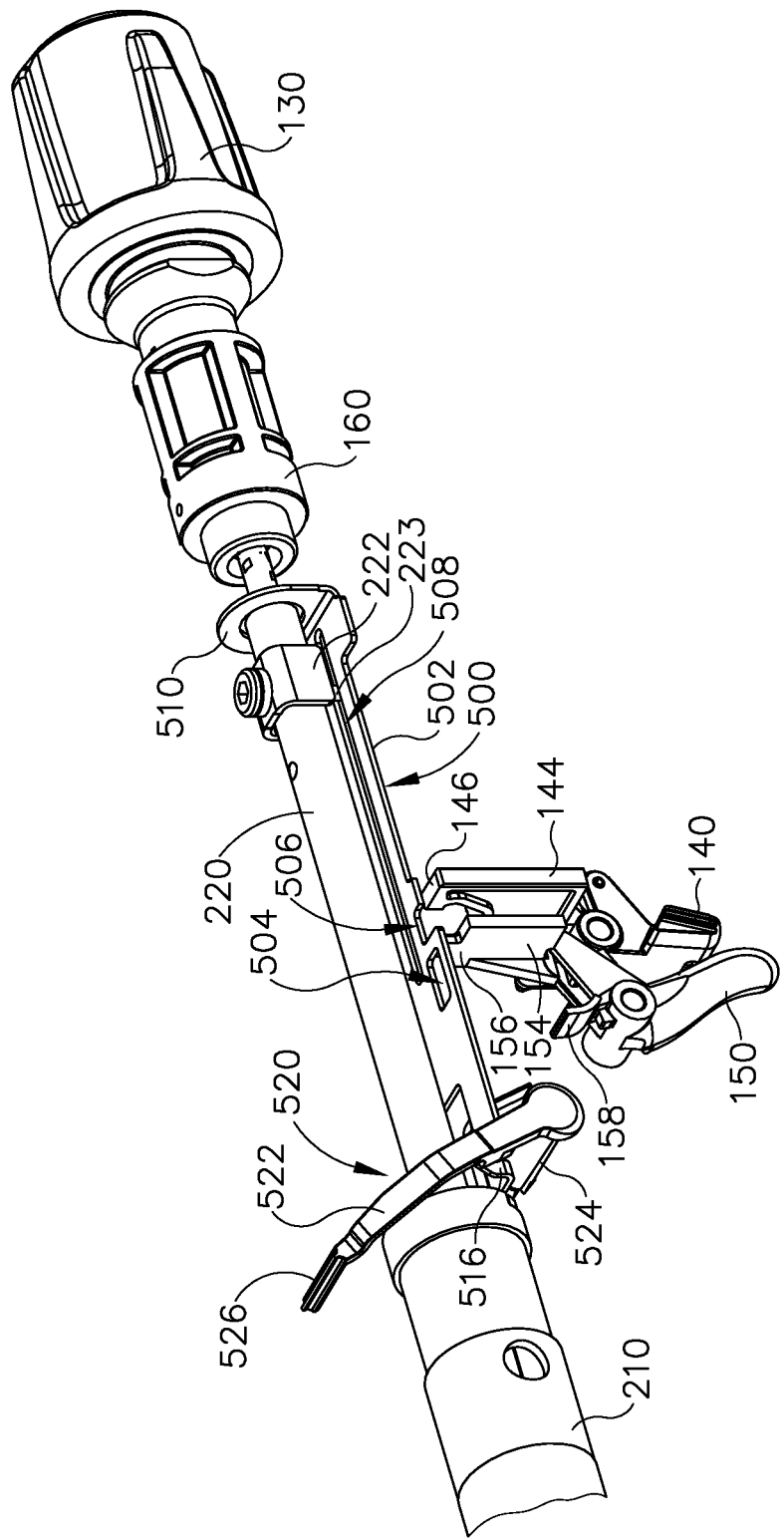
FIG. 12A depicts a perspective view of an anvil actuation assembly of the circular stapler of FIG. 1, an actuation rod in a first position.
Figure 12B:
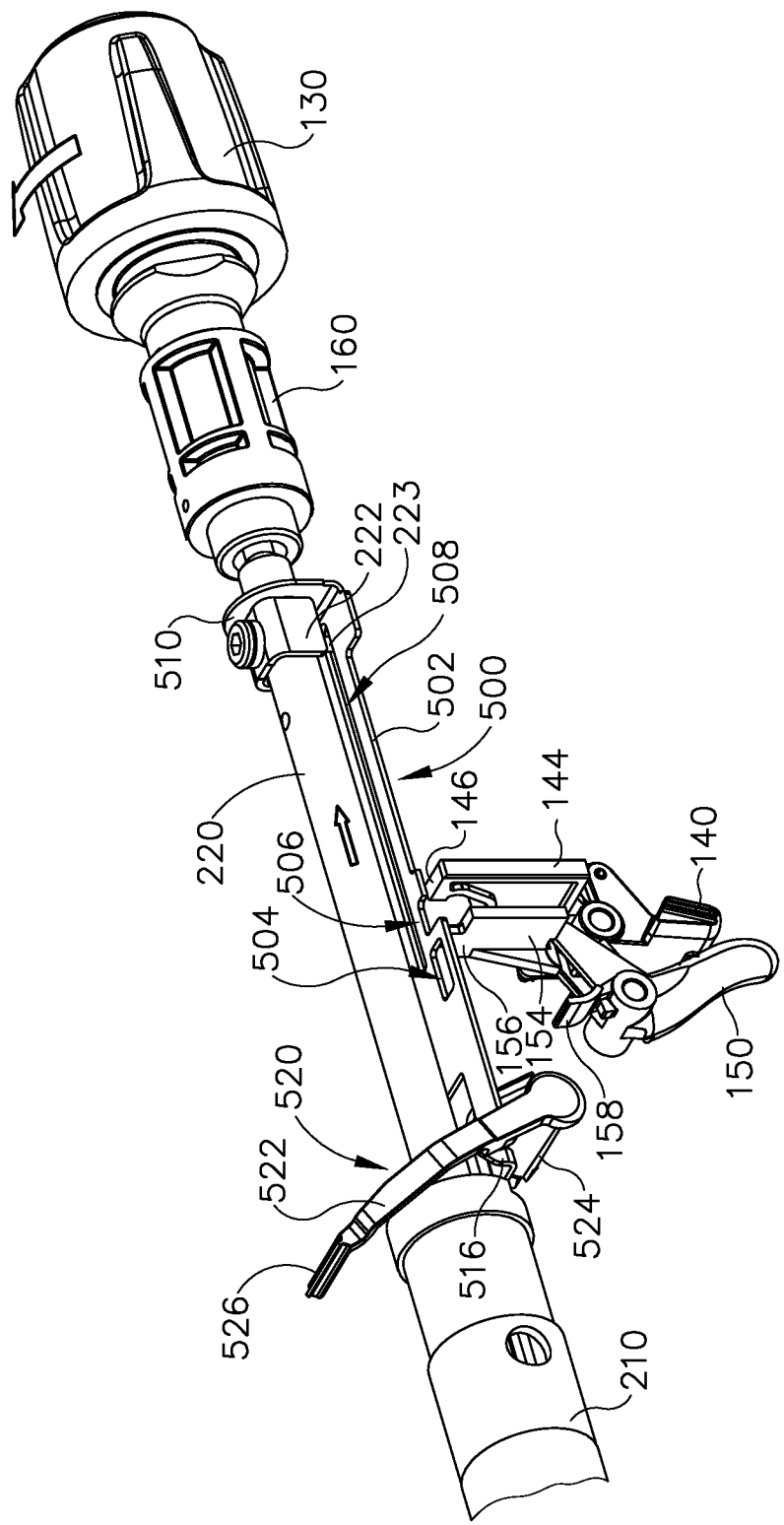
FIG. 12B depicts a perspective view of the anvil actuation assembly of FIG. 12A, with the actuation rod moved to a second position to engage the bracket of FIG. 10.
Figure 12C:
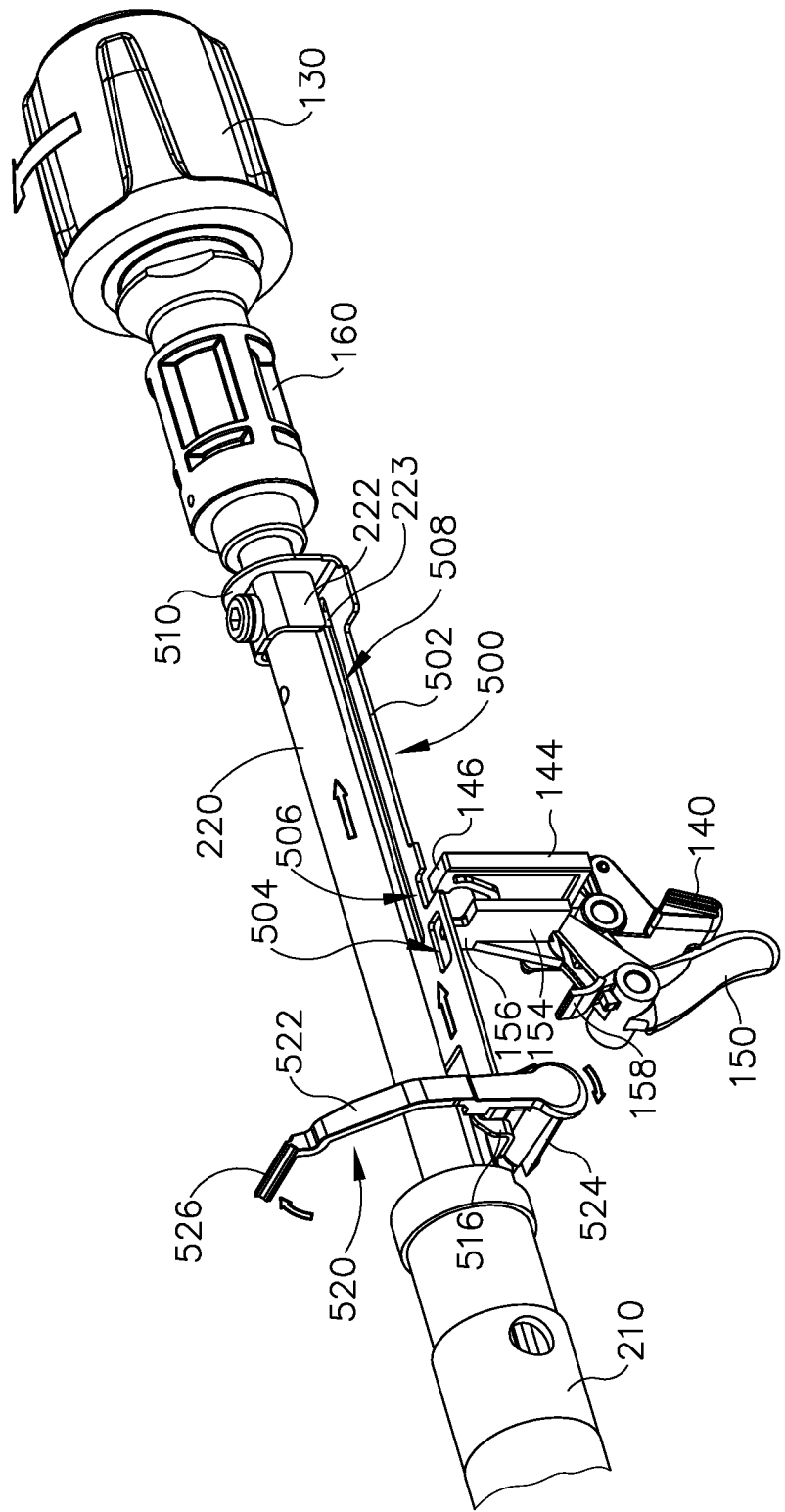
FIG. 12C depicts a perspective view of the anvil actuation assembly of FIG. 12A, with the actuation rod moved to a third position to retract the bracket of FIG. 10 proximally.

As best seen in FIGS. 12B-12C, an indicator member (520) is configured to pivot in response to translation of bracket (500). As best seen in FIG. 11, indicator member (520) comprises an upright arm (522), a snap pin (524) projecting laterally from a lower end of arm (522), an indicator needle (526) projecting laterally from an upper end of arm (522), and a coupling pin (528) projecting laterally from an intermediate region of arm (522). Snap pin (524) is configured to snap into a complementary recess provided by casing (110). Snap pin (524) thereby secures indicator member (520) to casing (110) yet permits indicator member (520) to pivot relative to casing (110) about the longitudinal axis of snap pin (524). Indicator needle (526) is positioned to be visible through window (114) of handle assembly (110) to thereby visually indicate the pivotal position of indicator member (520). Coupling pin (528) is slidably received in slot (514) of flange (516) of bracket (500). This engagement between indicator member (520), casing (110), and bracket (500) provides pivotal movement of indicator member (520) in response to translation of bracket (500).

Bracket (500) is configured to selectively prevent and permit actuation of triggers (140, 150). In particular, slots (504, 506) of bracket (500) are configured to selectively provide clearance for actuation of triggers (140, 150). As shown in FIGS. 12A-12E, safety trigger (140) is pivotably coupled with a first upright member (144). First upright member (144) is coupled with casing (110) such that first upright member (144) is configured to translate upwardly in response to pivoting of safety trigger (140) toward pistol grip (112). However, body (502) of bracket (500) is configured to prevent this movement of first upright member (144) and safety trigger (140) by engaging the upper end (146) of first upright member (144). Body (502) thus blocks movement of first upright member (144) and safety trigger (140) until bracket (500) is moved to a position where slot (506) is aligned with upper end (146) to thereby provide clearance for upward movement of first upright member (144). It should therefore be understood that safety trigger (140) cannot be pivoted toward pistol grip (112) until slot (506) is positioned over upper end (146).

Similarly, firing trigger (150) is pivotably coupled with a second upright member (154). Second upright member (154) is coupled with casing (110) such that second upright member (154) is configured to translate upwardly in response to pivoting of safety trigger (150) toward pistol grip (112). However, body (502) of bracket (500) is configured to prevent this movement of second upright member (154) and firing trigger (150) by engaging the upper end (156) of second upright member (154). Even if safety trigger (140) is pivoted out of the way to otherwise permit movement of firing trigger (150), body (502) blocks movement of second upright member (154) and firing trigger (150) until bracket (500) is moved to a position where slot (504) is aligned with upper end (156) to thereby provide clearance for upward movement of second upright member (154). It should therefore be understood that, even if safety trigger (140) is pivoted out of the way to otherwise permit movement of firing trigger (150), firing trigger (150) cannot be pivoted toward pistol grip (112) until slot (504) is positioned over upper end (156).

Third slot (508) is configured to receive a downwardly projecting boss (223) of clip (222), which is rigidly secured to trocar actuation rod (220). While casing (110) is configured to allow bracket (500) to translate longitudinally within casing (110), casing (110) includes rails, channels, and/or other features that prevent bracket (500) from rotating within casing (110). Thus, the positioning of boss (223) in slot (508) prevents clip (222) and trocar actuation rod (220) from rotating within casing (110). Boss (223) and slot (508) nevertheless allow bracket (500) to translate longitudinally within casing (110) as will be described in greater detail below.

FIGS. 12A-12E depict the above-described components at various stages of operation. In particular, in FIG. 12A, trocar actuation rod (220) is in a distal-most position, such that trocar (330) is in a distal-most position. At this stage, the operator may couple anvil (400) with trocar (330) by inserting trocar (330) into bore (422) until latch members (430) are secured to head (334) of trocar (330). The operator then rotates knob (130), which rotates nut (160). As knob (130)

and nut (160) rotate, engagement between coarse helical threading (224) of trocar actuation rod (220) and the complementary feature of nut (160) causes trocar actuation rod (220) to retract proximally at a relatively rapid rate, such that trocar actuation rod (220) reaches the position shown in FIG. 12B. This provides proximal retraction of trocar actuation rod (220) provides retraction of trocar (330) and anvil (400). As trocar actuation rod (220) moves from the position shown in FIG. 12A to the position shown in FIG. 12B, bracket (500) remains stationary. This is due to the fact that clip (222) is spaced apart from upright feature (510) at the stage shown in FIG. 12A and does not engage upright feature (510) until trocar actuation rod (220) reaches the position shown in FIG. 12B.

After reaching the stage shown in FIG. 12B, the operator may continue rotating knob (130) and nut (160), which causes further proximal retraction of trocar actuation rod (220) as shown in FIG. 12C. This of course causes further proximal retraction of trocar (330) and anvil (400). As trocar actuation rod (220) moves from the position shown in FIG. 12B to the position shown in FIG. 12C, clip (222) bears against bracket (500), driving bracket (500) proximally. This proximal movement of bracket (500) causes indicator member (520) to pivot from the position shown in FIG. 12B to the position shown in FIG. 12C due to the positioning of pin (528) in slot (514) of flange (516).

As indicator member (520) pivots from the position shown in FIG. 12B to the position shown in FIG. 12C, the operator may observe the position of indicator needle (526) through window (114) of handle assembly (110). As noted above, a series of hash marks, colored regions, and/or other fixed indicators may be positioned adjacent to window (114) in order to provide a visual context for indicator needle (526), thereby facilitating operator evaluation of the position of needle (526) within window (114). It should be understood that the position of needle (526) within window (114) will be indicative of the longitudinal position of trocar (330) and anvil (400). The position of needle (526) within window (114) will thus indicate the gap distance (d) between opposing surfaces (412, 322) of anvil (400) and stapling head assembly (300). While observing the position of needle (526) within window (114), the operator may rotate knob (130) clockwise or counterclockwise to further retract or advance trocar (330) and anvil (400), thereby providing fine adjustment of the gap distance (d) until a desired gap distance (d) is reached within an appropriate range.

In order to provide fine control of the gap distance (d) adjustment at the stage shown in FIG. 12C, trocar actuation rod (220) will be at a longitudinal position where fine helical threading (226) is engaged with a complementary feature of knob (130) and coarse helical threading (224) is disengaged from the complementary feature of nut (160). In some versions, coarse helical threading (224) disengages nut (160) and fine helical threading (226) begins to engage knob (130) once trocar actuation rod (220) reaches the longitudinal position shown in FIG. 12B (i.e., when clip (222) first engages upright member (510)). In some other versions, the transition from engagement by coarse helical threading (224) to fine helical threading (226) occurs sometime between the stage shown in FIG. 12B and the stage shown in FIG. 12C. Other suitable stages at which the coarse-to-fine transition may occur will be apparent to those of ordinary skill in the art in view of the teachings herein. It should also be understood that some alternative versions of trocar actuation rod (220) may have just a single threading section, with the pitch of the threading being consistent along the length of the threading. In other words, trocar actuation rod (220) does not necessarily need to have two different sections of threading (224, 226) with different pitches.

At the stage shown in FIG. 12C, slot (506) is aligned with upper end (146) to thereby provide clearance for upward movement of first upright member (144). Similarly, slot (504) is aligned with upper end (156) to thereby provide clearance for upward movement of second upright member (154). In the present example, slots (504, 506) are sized and positioned such that slots (504, 506) only provide clearance for upward movement of upright members (144, 154) when the gap distance (d) is within a clinically acceptable range. By way of example only, a "clinically acceptable range" for the gap distance (d) may be between approximately 0.110 inches and approximately 0.040 inches. As another merely illustrative example, a "clinically acceptable range" for the gap distance (d) may be between approximately 0.110 inches and approximately 0.020 inches. Even when slots (504, 506) are positioned to provide clearance for upward movement of upright members (144, 154) as shown in FIG. 12C, safety trigger (140) will still block pivotal movement of firing trigger (150) about a pin (152) (FIG. 9) when safety trigger (140) is in the non-actuated position shown in FIG. 12C. Thus, in order to enable movement of firing trigger (150), the operator will need to first actuate safety trigger (140) about a pin (142) (FIG. 9) from the position shown in FIG. 12C to the position shown in FIG. 12D.

Figure 12D:
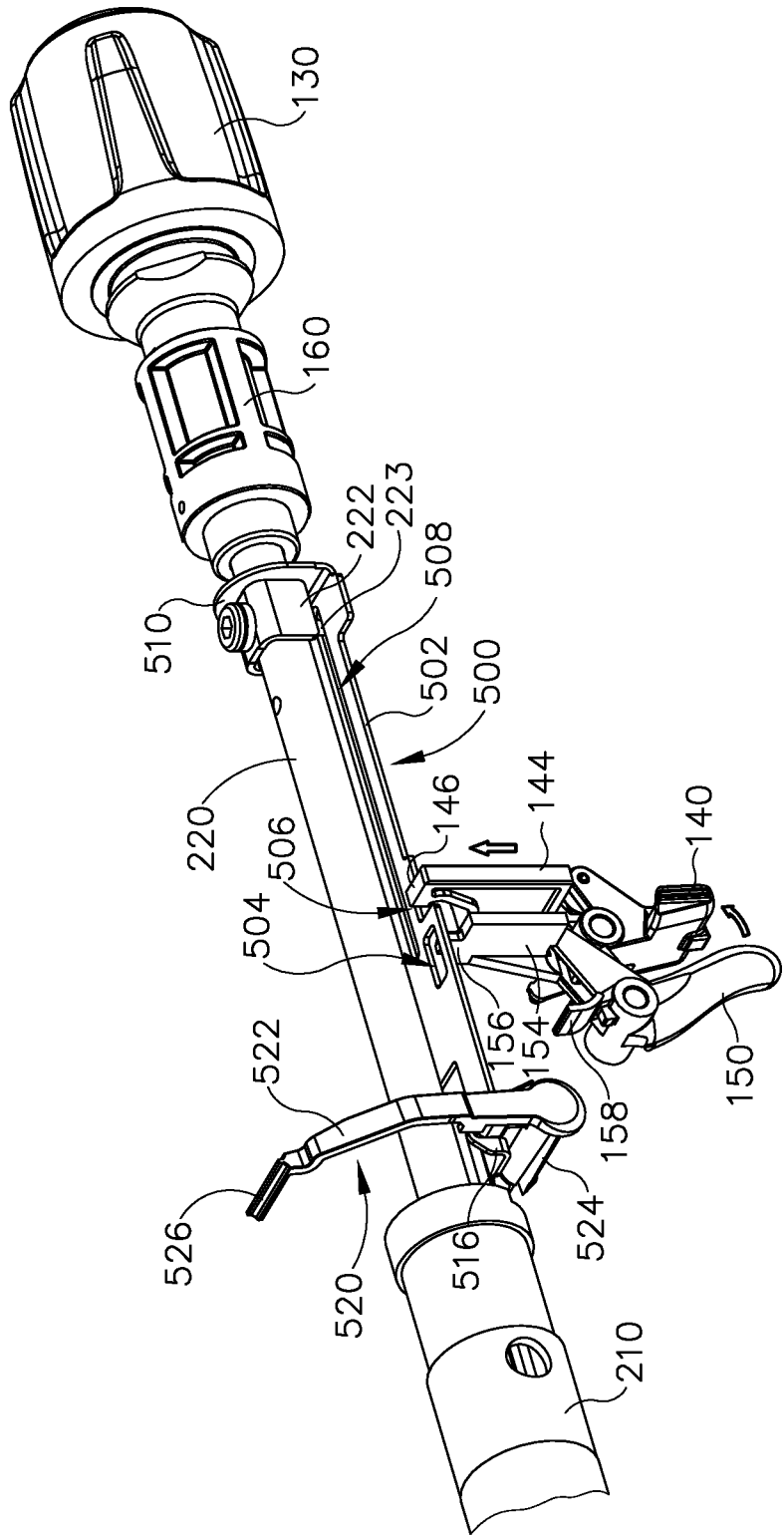
FIG. 12D depicts a perspective view of the anvil actuation assembly of FIG. 12A, with a safety trigger pivoted from a first position to a second position.

As shown in FIG. 12D, upper end (146) passes through slot (506) as safety trigger (140) is pivoted from the position shown in FIG. 12C to the position shown in FIG. 12D. It should be understood that this movement of upper end (146) would not be possible at the stages shown in FIGS. 12A-12B (when the gap distance (d) is too great) because body (502) would physically block upward movement of upright member (144), thereby physically blocking pivotal movement of safety trigger (140). In the present example, a cap (not shown) incorporated into knob (130) prevents knob (130) from rotating to a point where anvil (400) would be retracted too far proximally (such that the gap distance (d) is too small). In some other variations, even if knob (130) were to permit anvil (400) to be retracted too far proximally (such that the gap distance (d) is too small), body (502) would physically block upward movement of upright member (144), thereby physically blocking pivotal movement of safety trigger (140), in the event that the operator retracts trocar (330) and anvil (400) too far proximally (such that the gap distance (d) is too small). Regardless of whether body (502), knob (130), or some other feature prevents actuation when the gap distance (d) would be too small, it should be understood that instrument (10) permits actuation of safety trigger (140) only when the gap distance (d) is within the clinically acceptable range.

Figure 12E:
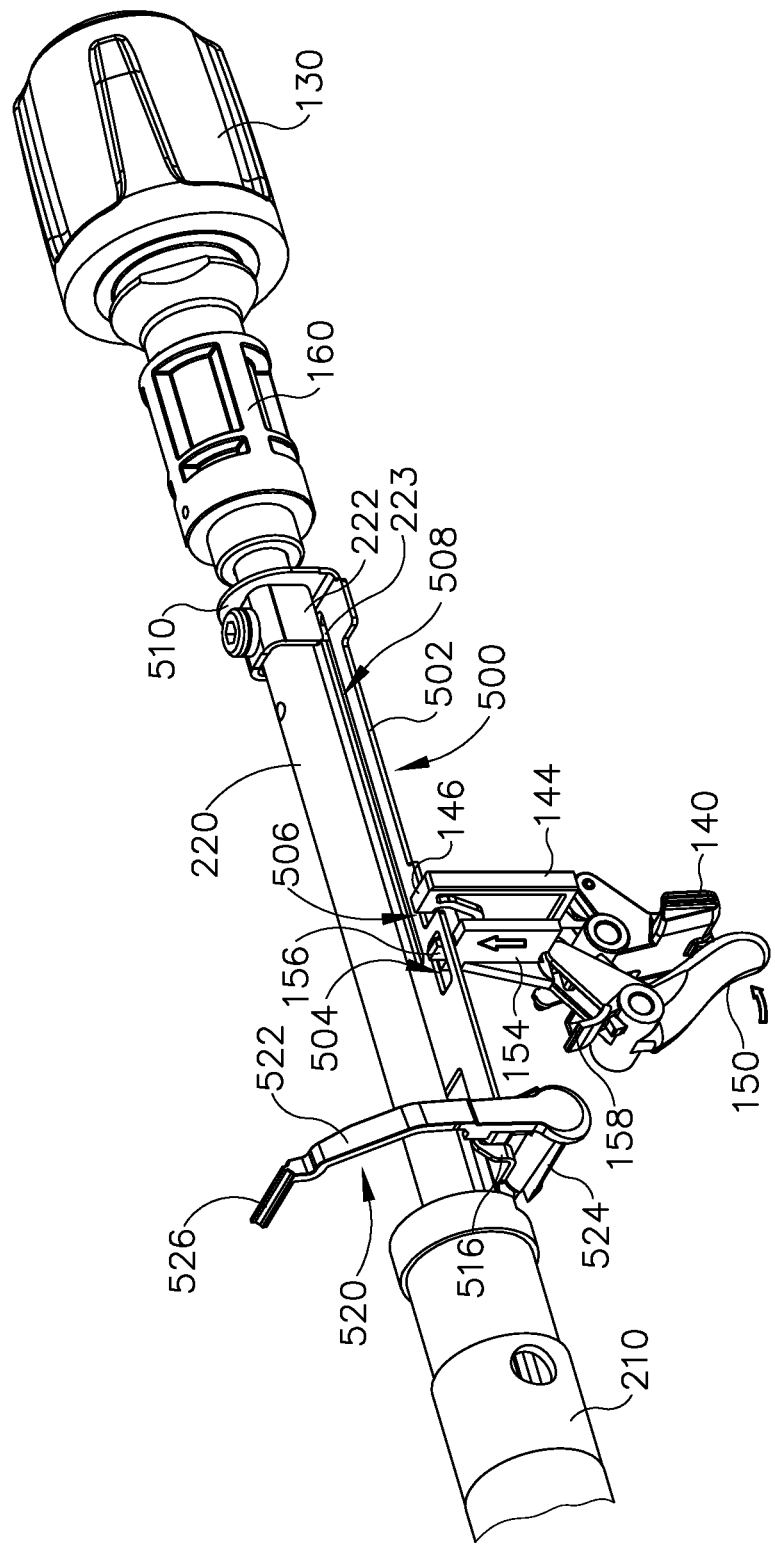
FIG. 12E depicts a perspective view of the anvil actuation assembly of FIG. 12A, with a firing trigger pivoted from a first position to a second position.
Figure 13:
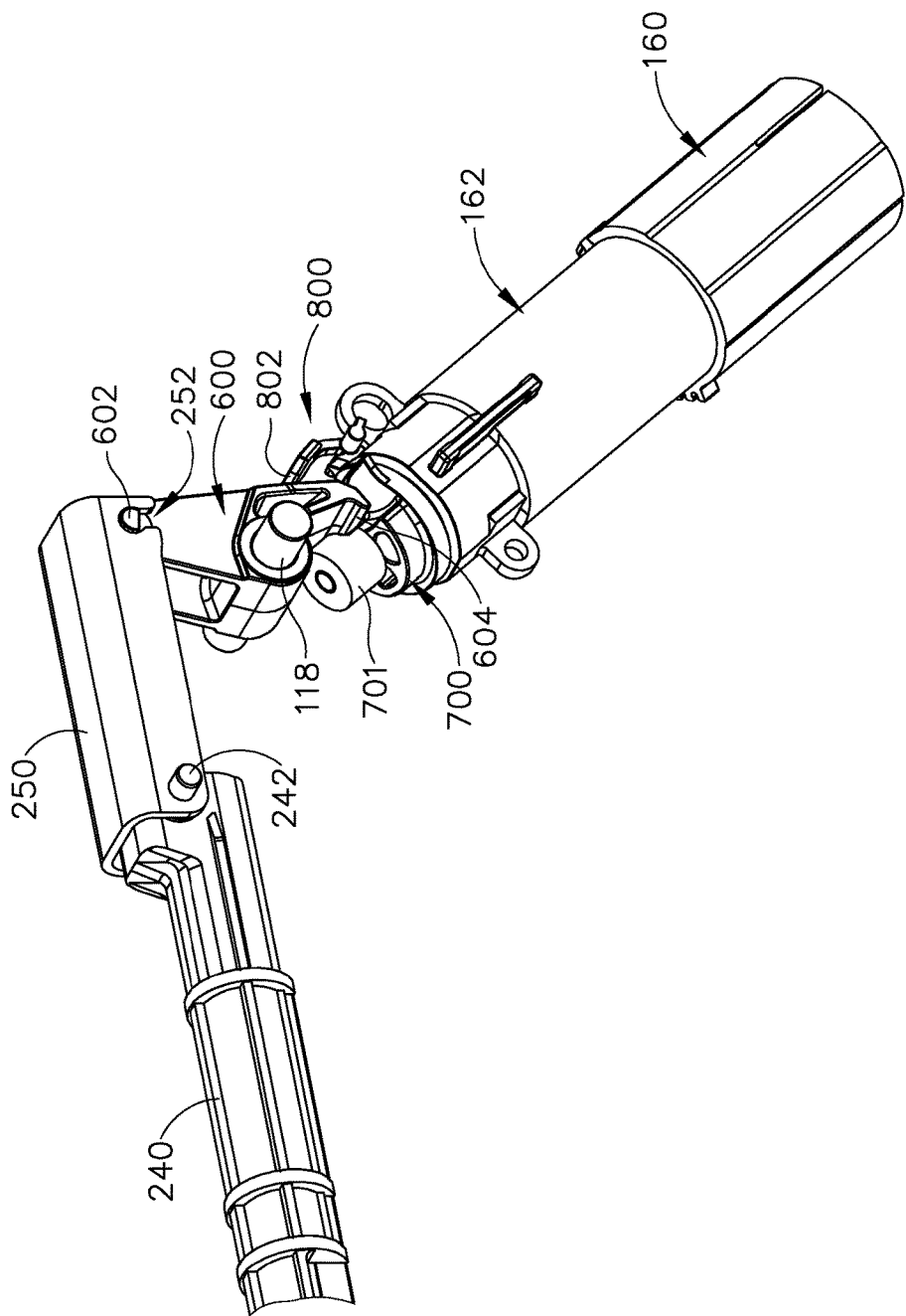
FIG. 13 depicts a perspective view of a stapling head actuation assembly of the circular stapler of FIG. 1.

As noted above, safety trigger (140) is configured to prevent actuation of firing trigger (150) until safety trigger (140) has been actuated. Once safety trigger (140) has been actuated, the operator may actuate firing trigger (150) from the position shown in FIG. 12D to the position shown in FIG. 12E. As shown in FIG. 12E, upper end (156) passes through slot (504) as firing trigger (150) is pivoted from the position shown in FIG. 12D to the position shown in FIG. 12E. It should be understood that, even in the complete absence of safety trigger (140), this movement of upper end (156) would not be possible at the stages shown in FIGS. 12A-12B (when the gap distance (d) is too great) because body (502) would physically block upward movement of upright member (154), thereby physically blocking pivotal movement of firing trigger (150). It should also be understood that body (502) would also physically block upward movement of upright member (154), thereby physically blocking pivotal movement of firing trigger (150), in the event that the operator retracts trocar (330) and anvil (400) too far proximally (such that the gap distance (d) is too small). Thus, even in the complete absence of safety trigger (140), firing trigger (150) may only be actuated when the gap distance (d) is within the clinically acceptable range.

Firing trigger (150) of the present example includes an integral actuation paddle (158). Paddle (158) pivots forwardly as firing trigger (150) pivots from the position shown in FIG. 12D to the position shown in FIG. 12E. Paddle (158) is configured to actuate a switch of a motor activation module (180), which is shown in FIG. 9, when firing trigger (150) pivots from the position shown in FIG. 12D to the position shown in FIG. 12E. Motor activation module (180) is in communication with battery pack (120) and motor (160), such that motor activation module (180) is configured to provide activation of motor (160) with electrical power from battery pack (120) in response to paddle (158) actuating the switch of motor activation module (180). Thus, motor (160) will be activated when firing trigger (150) is pivoted from the position shown in FIG. 12D to the position shown in FIG. 12E. This activation of motor (160) will actuate stapling head assembly (300) as described in greater detail below.

3. Exemplary Stapling Head Actuation Assembly

FIGS. 13-20D show various components that are operable to actuate stapling head assembly (300). These components include motor (160), a gearbox (162), a rotary cam member (700), a cam follower (600), drive bracket (250) and stapling head assembly driver (240). Gearbox (162) is coupled with a drive shaft of motor (160) and is further coupled with cam member (700). Activation of motor (160) thus causes rotation of cam member (700) via gearbox (162). Various suitable configurations that may be used for gearbox (162) will be apparent to those of ordinary skill in the art in view of the teachings herein. Cam member (700) is configured to interact with cam follower (160) to pivot cam follower (160) in two angular directions about a pin (118) as will be described in greater detail below. Pin (118) is coupled with casing (110). A bushing (701) provides rotary support to cam member (700) relative to casing (110).

Figure 14:
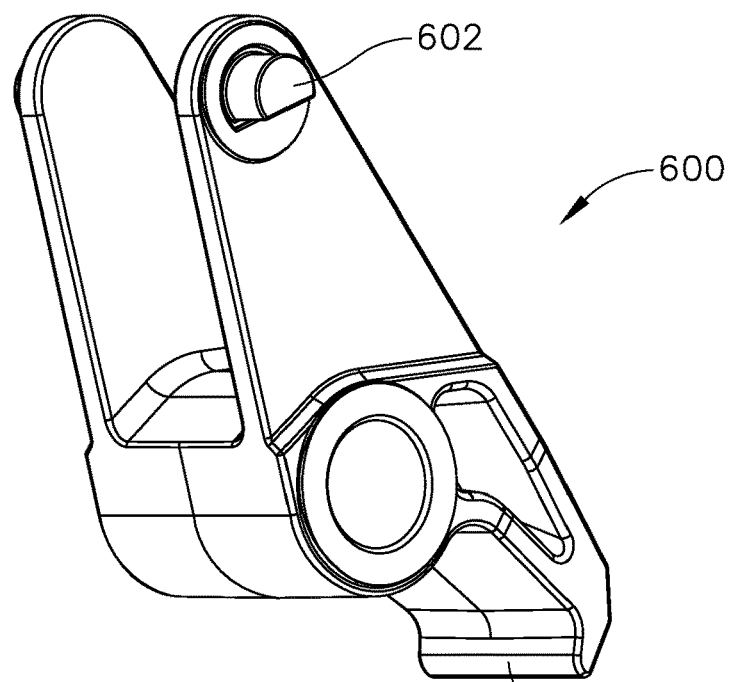
FIG. 14 depicts a perspective view of a cam follower of the stapling head actuation assembly of FIG. 13.
Figure 15:
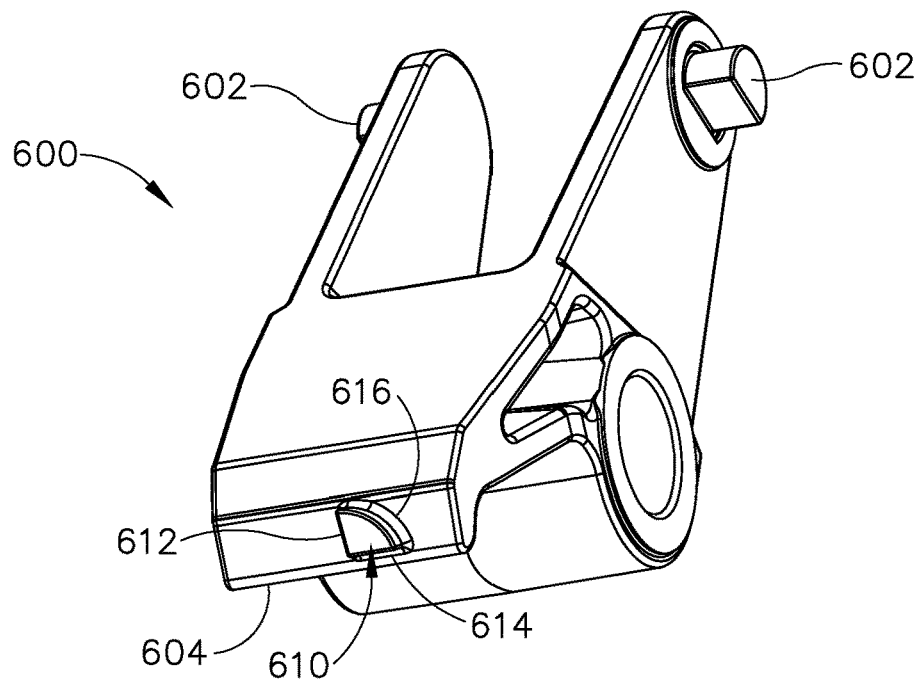
FIG. 15 depicts another perspective view of the cam follower of FIG. 14.

Cam follower (600) is pivotably coupled with drive bracket (250) via a pair of integral pins (602), which are received in complementary notches (252) of drive bracket (250). As shown in FIGS. 14-15, cam follower (600) includes a first bearing feature (604) and a second bearing feature (610). First bearing feature (604) consists of a rounded, horizontally extending surface. Second bearing feature (610) is shaped like a quarter-pie defined by a straight vertical surface (612), a horizontally extending surface (614), and a curved surface (616). Second bearing feature (610) projects proximally relative to first bearing feature (504).

Figure 16:
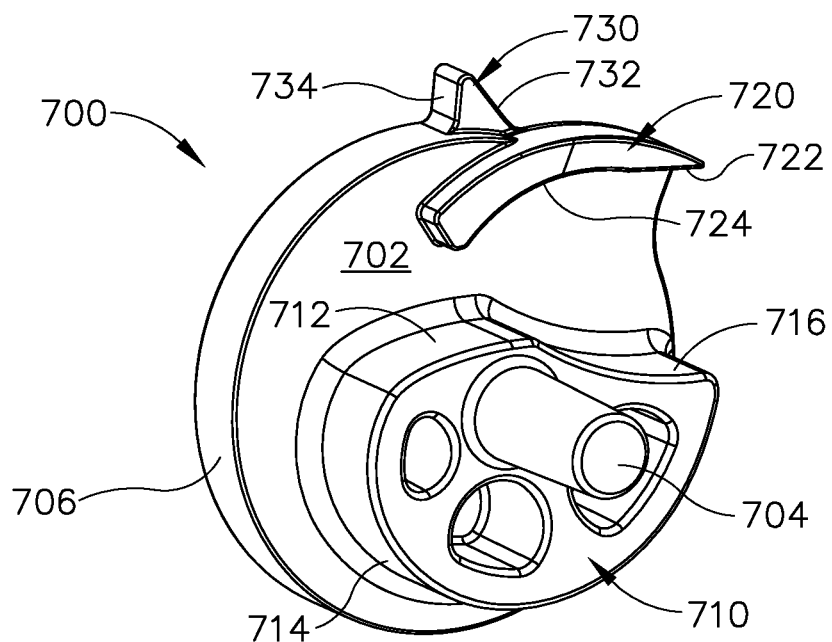
FIG. 16 depicts a perspective view of a rotary cam of the stapling head actuation assembly of FIG. 13.
Figure 17:
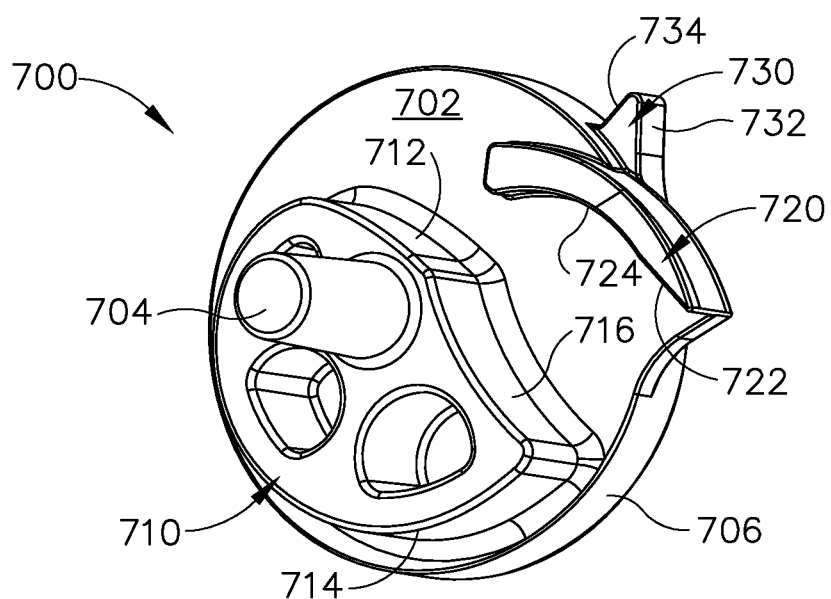
FIG. 17 depicts another perspective view of the rotary cam of FIG. 16.

FIGS. 16-17 show cam member (700) in greater detail. Cam member (700) comprises a distal face (702), a distally projecting post (704), and an outer circumferential surface (706). A first cam feature (710) and a second cam feature (720) project distally from distal face (702). Post (704) engages bushing (701). First cam feature (710) comprises a first surface region (712), a second surface region (714), and a third surface region (716). First surface region (712) is convexly defined by a relatively large radius of curvature, such that first surface region (712) is nearly flat. Second surface region (714) is convexly defined by a progressively increasing radius of curvature. Third surface region (716) is concavely defined by a relatively large radius of curvature. In addition to projecting distally from distal face (702), second cam feature (720) projects outwardly from outer circumferential surface (706). Second cam feature (720) includes a first surface region (722) and a second surface region (724). First surface region (722) is substantially flat while second surface region (724) is concavely curved. The origin of the radius of curvature for each curved surface region (712, 714, 716, 724) is offset from the center of post (704).

Figure 18A:
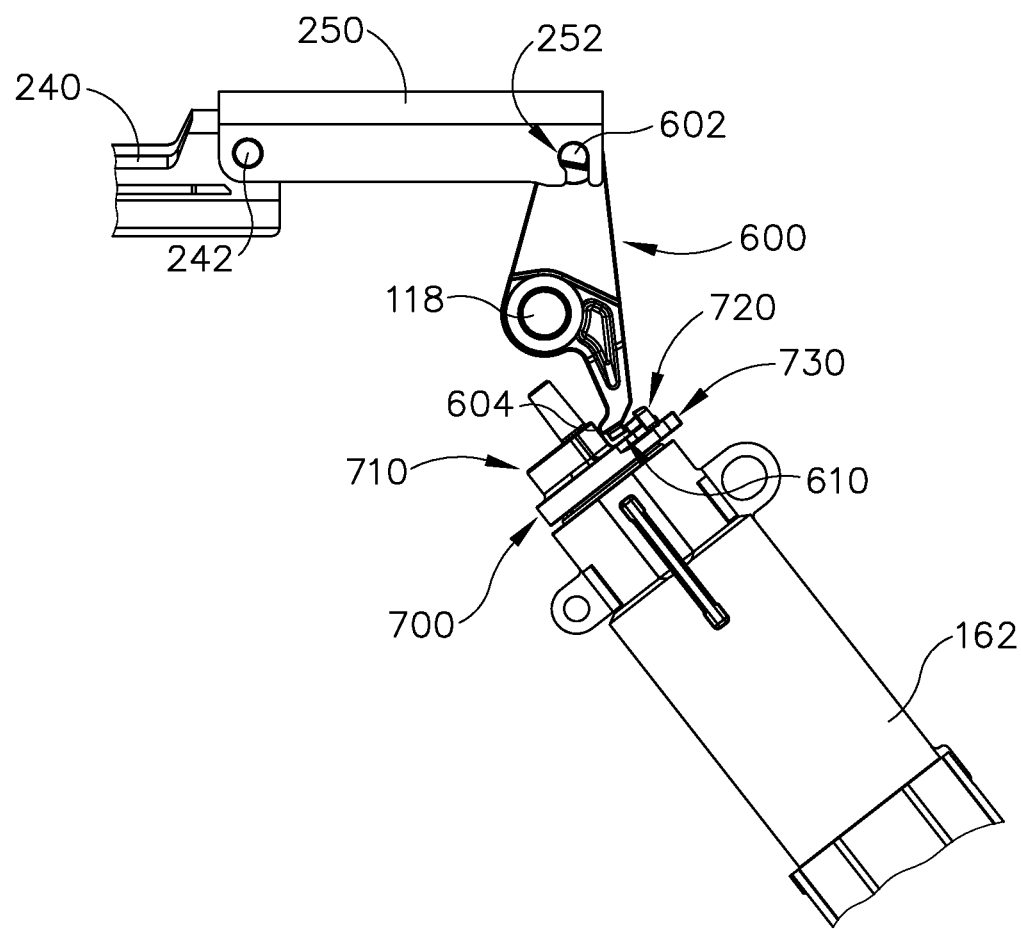
FIG. 18A depicts a side elevational view of the stapling head actuation assembly of FIG. 13, with the rotary cam in a first angular position and the cam follower in a first pivotal position.
Figure 18B:
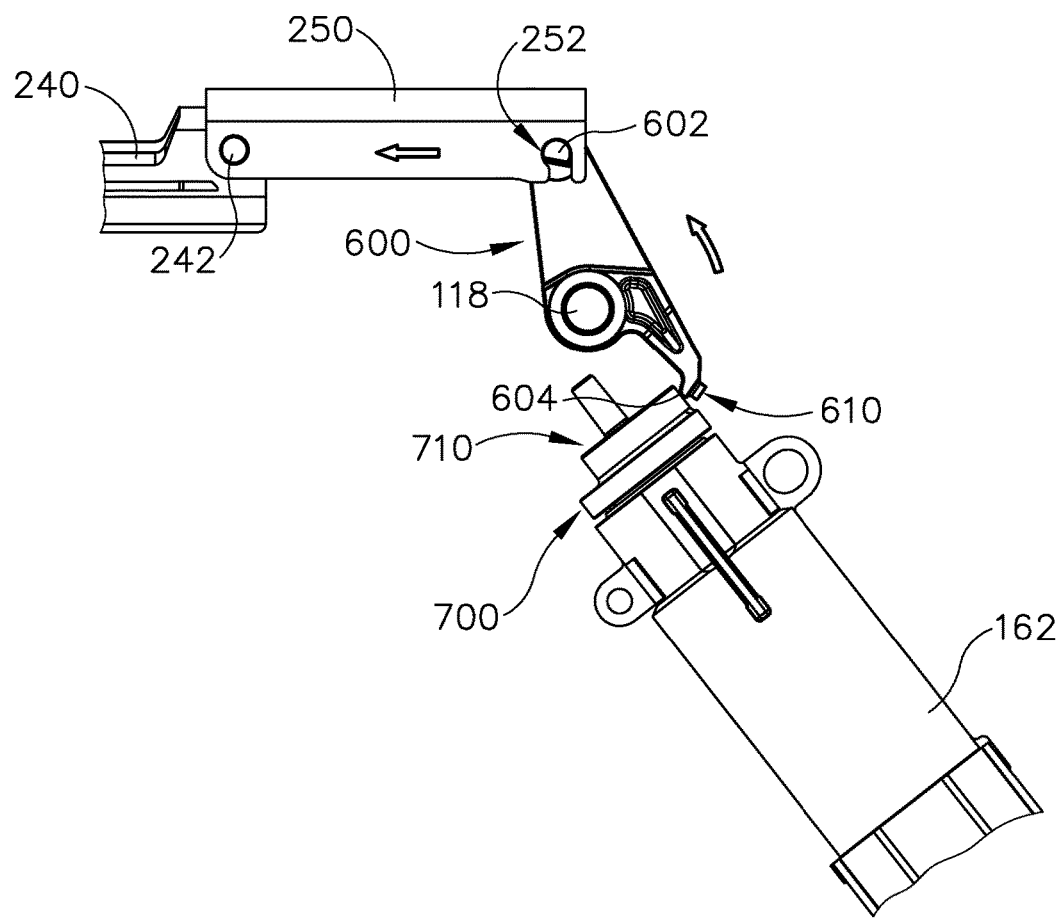
FIG. 18B depicts a side elevational view of the stapling head actuation assembly of FIG. 13, with the rotary cam in a second angular position and the cam follower in a second pivotal position.

FIGS. 18A-18B show the general interaction between cam follower (600) and first and second cam features (710, 720), though this interaction will be described in greater detail below with reference to FIGS. 20A-20D. As cam member (700) is rotated from the position shown in FIG. 18A to the position shown in FIG. 18B, first cam feature (710) bears against first bearing feature (604) of cam follower (600), causing cam follower to pivot about pin (118). In the view shown in FIGS. 18A-18B, cam follower (600) pivots counterclockwise as cam member (700) is rotated from the position shown in FIG. 18A to the position shown in FIG. 18B. As can be seen in the transition from FIG. 18A to FIG. 18B, this counterclockwise pivoting of cam follower (600) drives drive bracket (250) and stapling head assembly driver (240) distally, thereby actuating stapling head assembly (300). As cam member (700) continues to rotate in the same direction back toward the position shown in FIG. 18A, second cam feature (720) engages and bears against second bearing feature (610) of cam follower (600), causing cam follower (600) to pivot clockwise about pin (118). This clockwise pivoting of cam follower (600) about pin (118) retracts drive bracket (250) and stapling head assembly driver (240) proximally back toward the position shown in FIG. 18A.

Figure 19A:
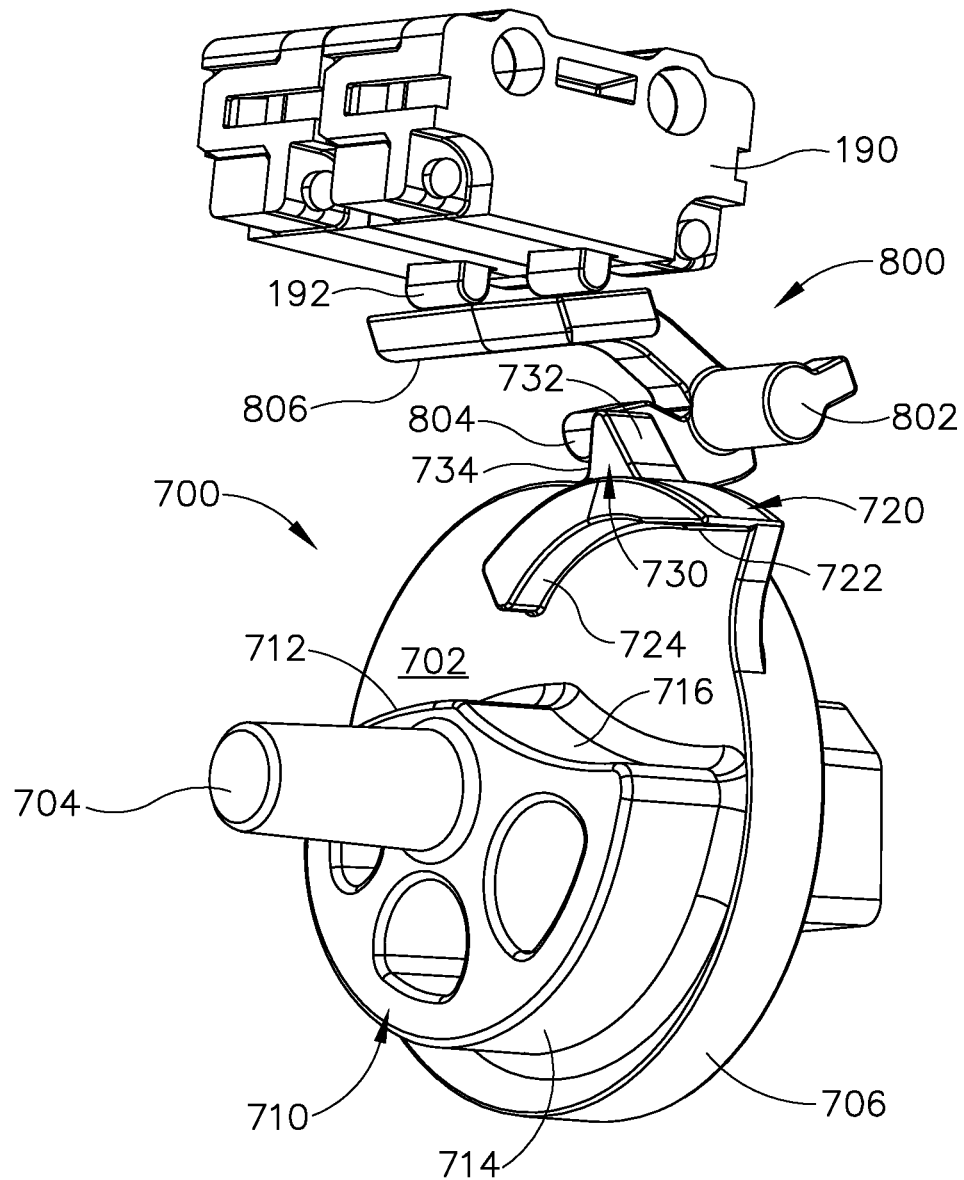
FIG. 19A depicts a perspective view of the rotary cam of FIG. 16, a rocker member, and a stop switch, with the rotary cam in a first angular position and the rocker member in a first pivotal position.
Figure 19B:
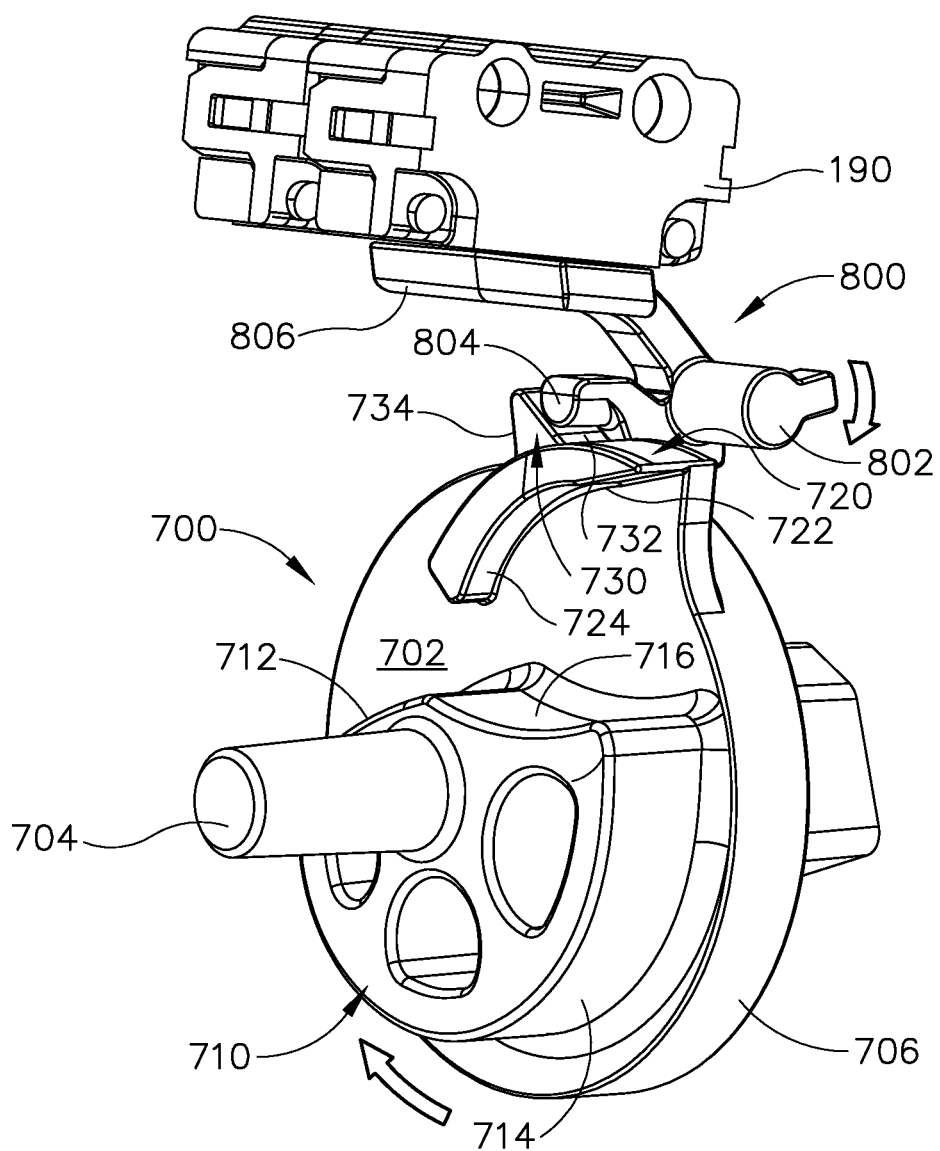
FIG. 19B depicts a perspective view of the rotary cam of FIG. 16, the rocker member of FIG. 19A, and the stop switch of FIG. 19A, with the rotary cam in a fourth angular position and the rocker member in a second pivotal position.

Referring back to FIGS. 16-17, a third cam feature (730) projects outwardly from outer circumferential surface (706). Third cam feature (730) comprises a first surface region (732) and a second surface region (734). First surface region (732) is flat and is oriented generally tangentially relative to outer circumferential surface (706). Second surface region (732) is also flat and is oriented radially outwardly relative to outer circumferential surface (706). Third cam feature (730) is configured to interact with a rocker member (800) as shown in FIGS. 19A-19B. Rocker member (800) comprises an integral pin (802), a bearing member (804), and a paddle (806). Pin (802) is pivotably coupled with casing (110), such that rocker member (800) is pivotable within casing (110) about the longitudinal axis defined by pin (802). Bearing member (804) is configured to interact with third cam feature (730) as will be described in greater detail below. Paddle (806) is configured to actuate a switch button (192) of a short circuit module (190) as will also be described in greater detail below.

FIG. 19A shows cam member (700) in the same position as shown in FIG. 18A. At this stage, second surface region (734) of third cam feature (730) is adjacent to bearing member (804) of rocker member (800). FIG. 19B shows cam member (700) in a position where cam member (700) has been rotated past the position shown in FIG. 18B and back toward the position shown in FIG. 18A. However, cam member (700) has not completed a full revolution. At the stage shown in FIG. 19B, first surface region (732) has engaged and borne against bearing member (804), thereby pivoting rocker member (800) about the longitudinal axis defined by pin (802). This has caused paddle (806) to actuate switch button (192) of short circuit module (190). Short circuit module (190) is configured to prevent motor (160) from further activation when switch button (192) has been actuated. In some versions, short circuit module (190) couples battery pack (120) with a power sink, in addition to short circuiting motor (160), when switch button (192) is actuated. This may result in discharge of battery pack (120) in addition to stopping activation of motor (160) once an actuation stroke of stapling head assembly (300) has been completed. By way of example only, short circuit module (190) may be configured and operable in accordance with at least some of the teachings of U.S. Pub. No. 2015/0083774, issued as U.S. Pat. No. 9,907,552 on Mar. 6, 2018, the disclosure of which is incorporated by reference herein. Other suitable configurations will be apparent to those of ordinary skill in the art in view of the teachings herein.

Figure 20A:
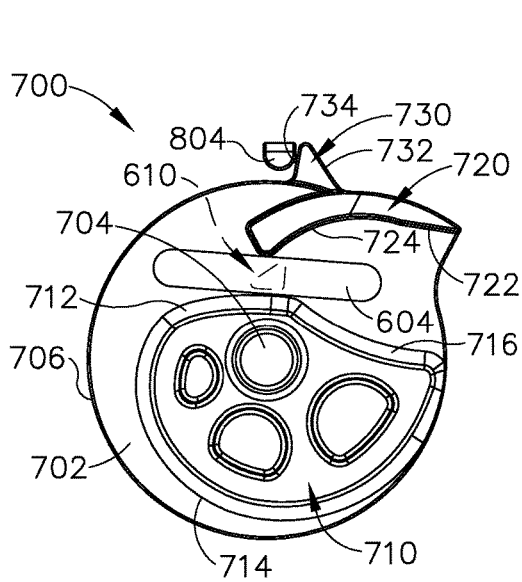
FIG. 20A depicts a schematic end view of the rotary cam of FIG. 16, the cam follower of FIG. 14, and the rocker member of FIG. 19A, with the rotary cam in the first angular position, the cam follower in the first pivotal position, and the rocker member in the first pivotal position.
Figure 20B:
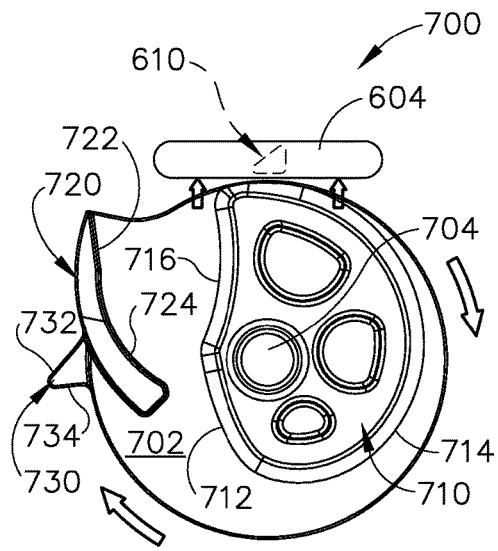
FIG. 20B depicts a schematic end view of the rotary cam of FIG. 16 and the cam follower of FIG. 14, with the rotary cam in the second angular position, the cam follower in the second pivotal position, and the rocker member of FIG. 19A in the first pivotal position.

FIGS. 20A-20D schematically depict the interaction between cam member (700), features of cam follower (600), and features of rocker member (800) as cam member (700) rotates. It should be understood that the rotation of cam member (700) throughout the stages shown in FIGS. 20A-20D is driven by motor (160) and gearbox (162). FIG. 20A shows cam member (700) in the same position as shown in FIGS. 18A and 19A. At this stage, first bearing feature (604) of cam follower (600) is positioned on first surface region (712) and bearing member (804) or rocker member (800) is adjacent to second surface region (734) of third cam feature (730). Also at this stage, knife member (340) and staple driver member (350) are in proximal positions, such that stapling head assembly (300) is in a non-actuated state. As cam member (700) is rotated to the position shown in FIG. 20B, second surface region (714) bears against bearing member (804), thereby driving bearing member (804) upwardly. This causes cam follower (600) to pivot about pin (118) to the position shown in FIG. 18B. Cam follower (600) thus drives knife member (340) and staple driver member (350) distally via drive bracket (250) and stapling head assembly driver (240). Stapling head assembly (300) is thus in an actuated state at the stage shown in FIG. 20B. In some versions, cam member (700) rotates through an angular range of approximately 270° in order to transition stapling head assembly (300) from the non-actuated state to the actuated state.

Figure 20C:
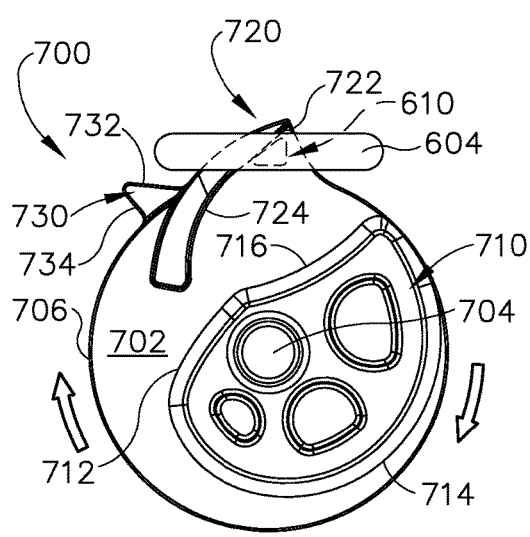
FIG. 20C depicts a schematic end view of the rotary cam of FIG. 16 and the cam follower of FIG. 14, with the rotary cam in a third angular position, the cam follower in the second pivotal position, and the rocker member of FIG. 19A in the first pivotal position.
Figure 20D:
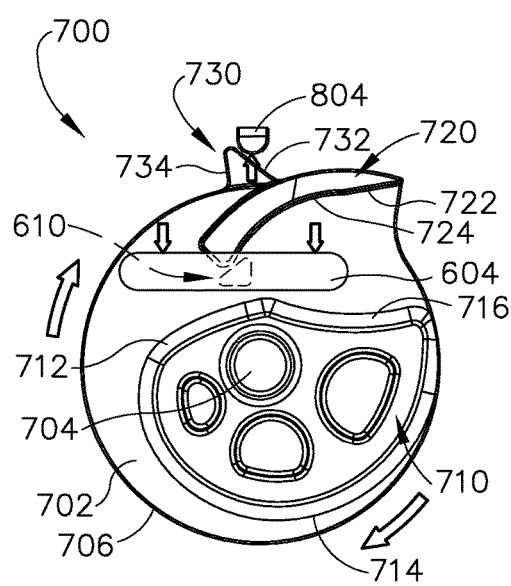
FIG. 20D depicts a schematic end view of the rotary cam of FIG. 16, the cam follower of FIG. 14, and the rocker member of FIG. 19A, with the rotary cam in a fourth angular position, the cam follower in a third pivotal position, and the rocker member in a second pivotal position.

After stapling head assembly (300) has been actuated, cam member (700) continues to rotate to the position shown in FIG. 20C. At this stage, first surface region (722) of second cam member (720) begins to engage curved surface (616) of second bearing feature (610) of cam follower (600). As cam member (700) continues to rotate to the position shown in FIG. 20D, second surface region (724) engages curved surface (616) of second bearing feature (610), driving second bearing feature (610) downwardly. This causes cam follower (600) to pivot about pin (118) back from the position shown in FIG. 18B toward the position shown in FIG. 18A. Cam follower (600) thus drives knife member (340) and staple driver member (350) proximally via drive bracket (250) and stapling head assembly driver (240). In addition, first surface region (732) has engaged and borne against bearing member (804), thereby pivoting rocker member (800) about the longitudinal axis defined by pin (802) at the stage shown in FIG. 20D. Rocker member (800) is thus in the same state in FIG. 20D as shown in FIG. 19B. Short circuit module (190) has thus been actuated at the stage shown in FIG. 20D.

It should be understood from the foregoing that cam member (700) is operable to drive knife member (340) and staple driver member (350) distally, then drive knife member (340) and staple driver member (350) proximally and actuate short circuit module (190) by rotating in a single angular direction through the range of motion shown in FIGS. 20A-20D. Other suitable ways in which knife member (340), staple driver member (350), and short circuit module (190) may be actuated will be apparent to those of ordinary skill in the art in view of the teachings herein.

E. Exemplary Anastomosis Procedure

Figure 21A:
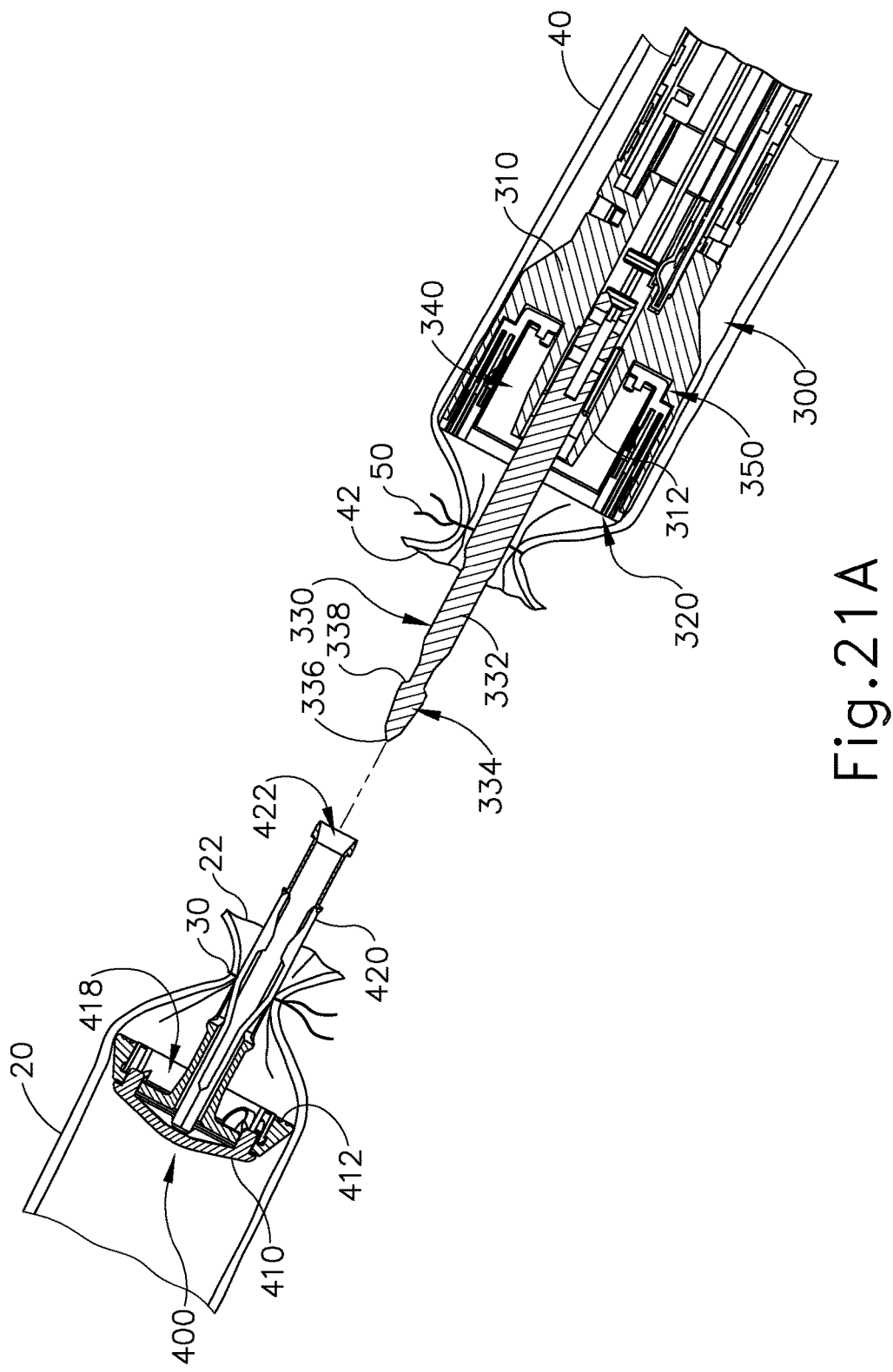
FIG. 21A depicts a cross-sectional side view of the anvil of FIG. 3 positioned within a first section of a digestive tract and the stapling head assembly of FIG. 6 positioned in a second section of the digestive tract, with the anvil separated from the stapling head assembly.
Figure 21C:
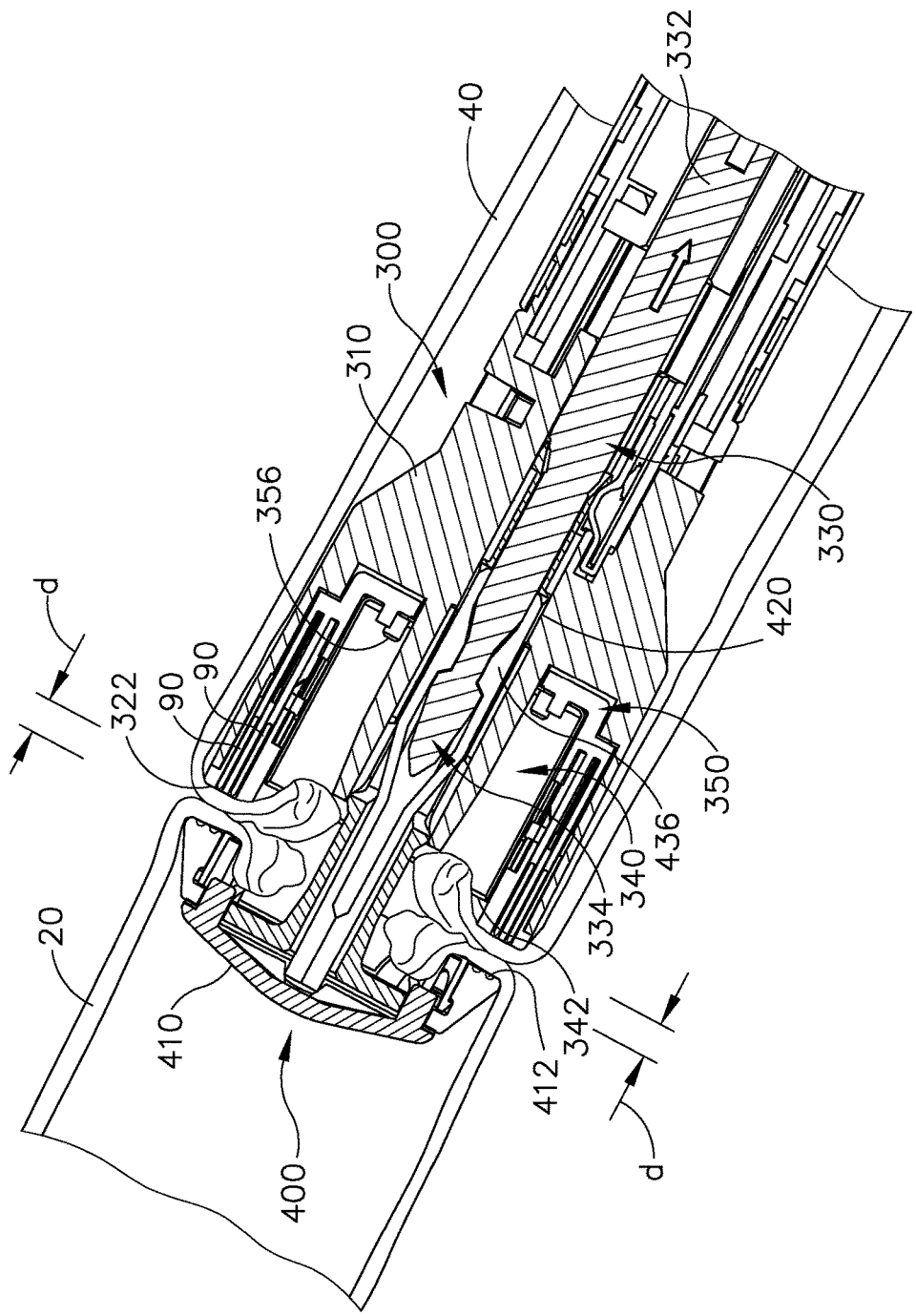
FIG. 21C depicts a cross-sectional side view of the anvil of FIG. 3 positioned within the first section of the digestive tract and the stapling head assembly of FIG. 6 positioned in the second section of the digestive tract, with the anvil retracted toward the stapling head assembly to thereby clamp tissue between the anvil and the stapling head assembly.

FIGS. 21A-21E show instrument (10) being used to form an anastomosis (70) between two tubular anatomical structures (20, 40). By way of example only, the tubular anatomical structures (20, 40) may comprise sections of a patient's esophagus, sections of a patient's colon, other sections of the patient's digestive tract, or any other tubular anatomical structures. As shown in FIG. 21A, anvil (400) is positioned in one tubular anatomical structure (20) and stapling head assembly (300) is positioned in another tubular anatomical structure (40). In versions where tubular anatomical structures (20, 40) comprise sections of a patient's colon, stapling head assembly (300) may be inserted via the patient's rectum. It should also be understood that the procedure depicted in FIGS. 21A-21E is an open surgical procedure, though the procedure may instead be performed laparoscopically. Various suitable ways in which instrument (10) may be used to form an anastomosis (70) in a laparoscopic procedure will be apparent to those of ordinary skill in the art in view of the teachings herein.

As shown in FIG. 21A, anvil (400) is positioned in tubular anatomical structure (20) such that shank (420) protrudes from the open severed end (22) of tubular anatomical structure (20). A purse-string suture (30) is provided about a mid-region of shank (420) to generally secure the position of anvil (400) in tubular anatomical structure (20). Similarly, stapling head assembly (300) is positioned in tubular anatomical structure (40) such that trocar (330) protrudes from the open severed end (42) of tubular anatomical structure (20). A purse-string suture (50) is provided about a mid-region of shaft (332) to generally secure the position of stapling head assembly (300) in tubular anatomical structure (40).

Next, anvil (400) is secured to trocar (330) by inserting trocar (330) into bore (422) as shown in FIG. 21B. Latch members (430) engage head (334) of trocar (330), thereby providing a secure fit between anvil (400) and trocar (330). The operator then rotates knob (130) while holding casing (110) stationary via pistol grip (112). This rotation of knob (130) causes trocar (330) and anvil (400) to retract proximally (as described above with reference to FIGS. 12A-12C). As shown in FIG. 21C, this proximal retraction of trocar (330) and anvil (400) compresses the tissue of tubular anatomical structures (20, 40) between surfaces (412, 322) of anvil (400) and stapling head assembly (300). The operator observes the position of needle (526) within window (114) to determine whether the gap distance (d) between opposing surfaces (412, 322) of anvil (400) and stapling head assembly (300) is appropriate; and makes any necessary adjustments via knob (130).

Once the operator has appropriately set the gap distance (d) via knob (130), the operator actuates safety trigger (140) (as shown in FIG. 12D) to enable actuation of firing trigger (150). The operator then actuates firing trigger (150) (as shown in FIG. 12D). This causes paddle (158) to actuate the switch of a motor activation module (180), thereby activating motor to rotate cam member (700) (as shown in FIGS. 20A-20D). This rotation of cam member (700) actuates stapling head assembly (300) by driving knife member (340) and staple driver member (350) distally as shown in FIG.

21D. As knife member (340) translates distally, cutting edge (342) of knife member (340) cooperates with inner edge (416) of anvil (400), thereby shearing excess tissue that is positioned within annular recess (418) of anvil (400) and the interior of knife member (340).

As shown in FIG. 4, anvil (400) of the present example includes a breakable washer (417) within annular recess (418). This washer (417) is broken by knife member (340) when the knife member (340) completes a full distal range of motion from the position shown in FIG. 21C to the position shown in FIG. 21D. The progressively increasing radius of curvature of second surface region may provide an increasing mechanical advantage as knife member (340) reaches the end of its distal movement, thereby providing greater force by which to break the washer (417). Of course, the breakable washer (417) may be omitted entirely in some versions. In versions where washer (417) is included, it should be understood that washer (417) may also serve as a cutting board for knife member (340) to assist in cutting of tissue. Such a cutting technique may be employed in addition to or in lieu of the above-noted shearing action between inner edge (416) and knife member (340).

Figure 21D:
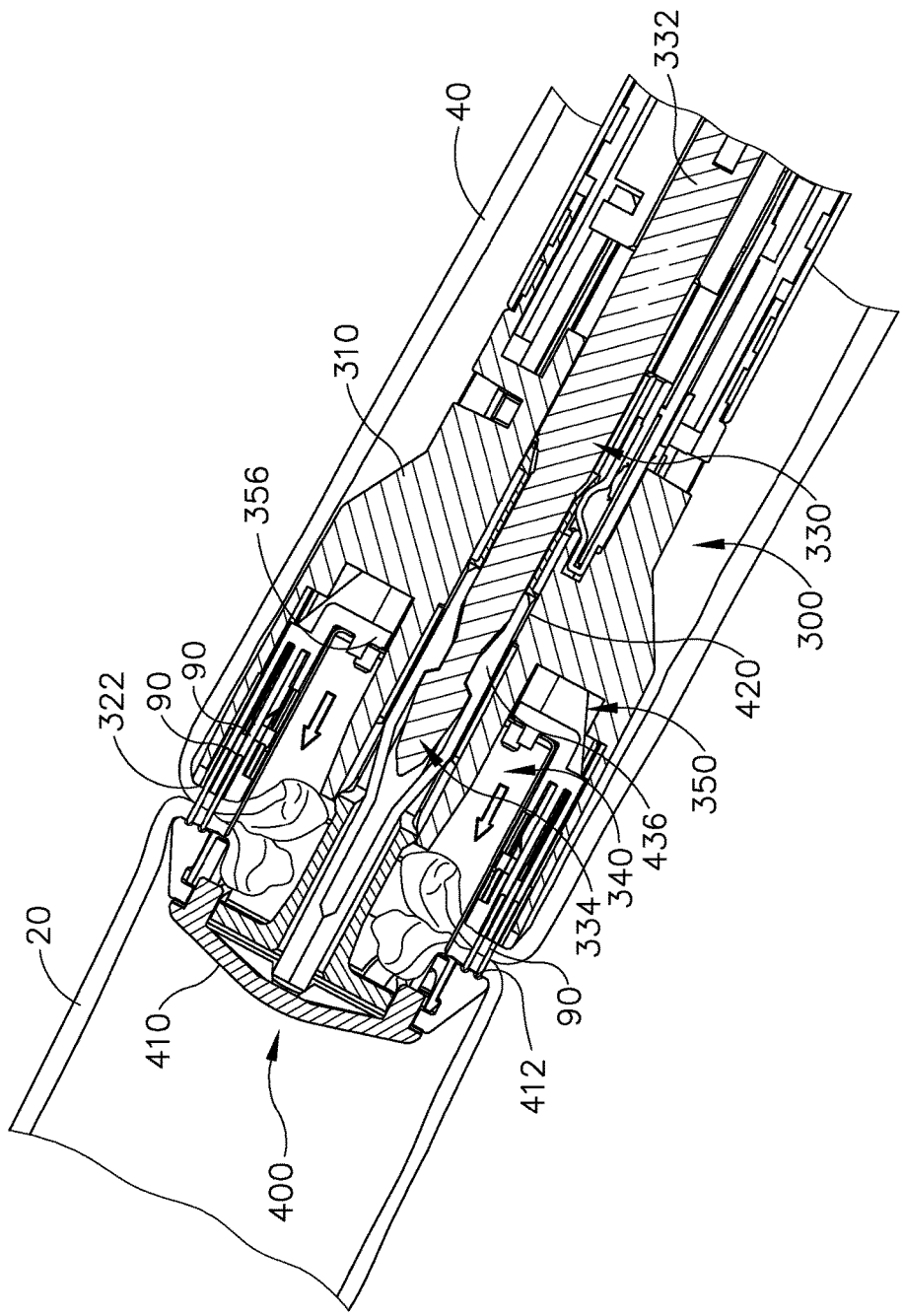
FIG. 21D depicts a cross-sectional side view of the anvil of FIG. 3 positioned within the first section of the digestive tract and the stapling head assembly of FIG. 6 positioned in the second section of the digestive tract, with the stapling head assembly actuated to sever and staple the clamped tissue.

As staple driver member (350) translates distally from the position shown in FIG. 21C to the position shown in FIG. 21D, staple driver member (350) drives staples (90) through the tissue of tubular anatomical structures (20, 40) and into staple forming pockets (414) of anvil (400). Staple forming pockets (414) deform the driven staples (90) into a "B" shape as is known in the art. The formed staples (90) thus secure the ends of tissue together.

Figure 21E:
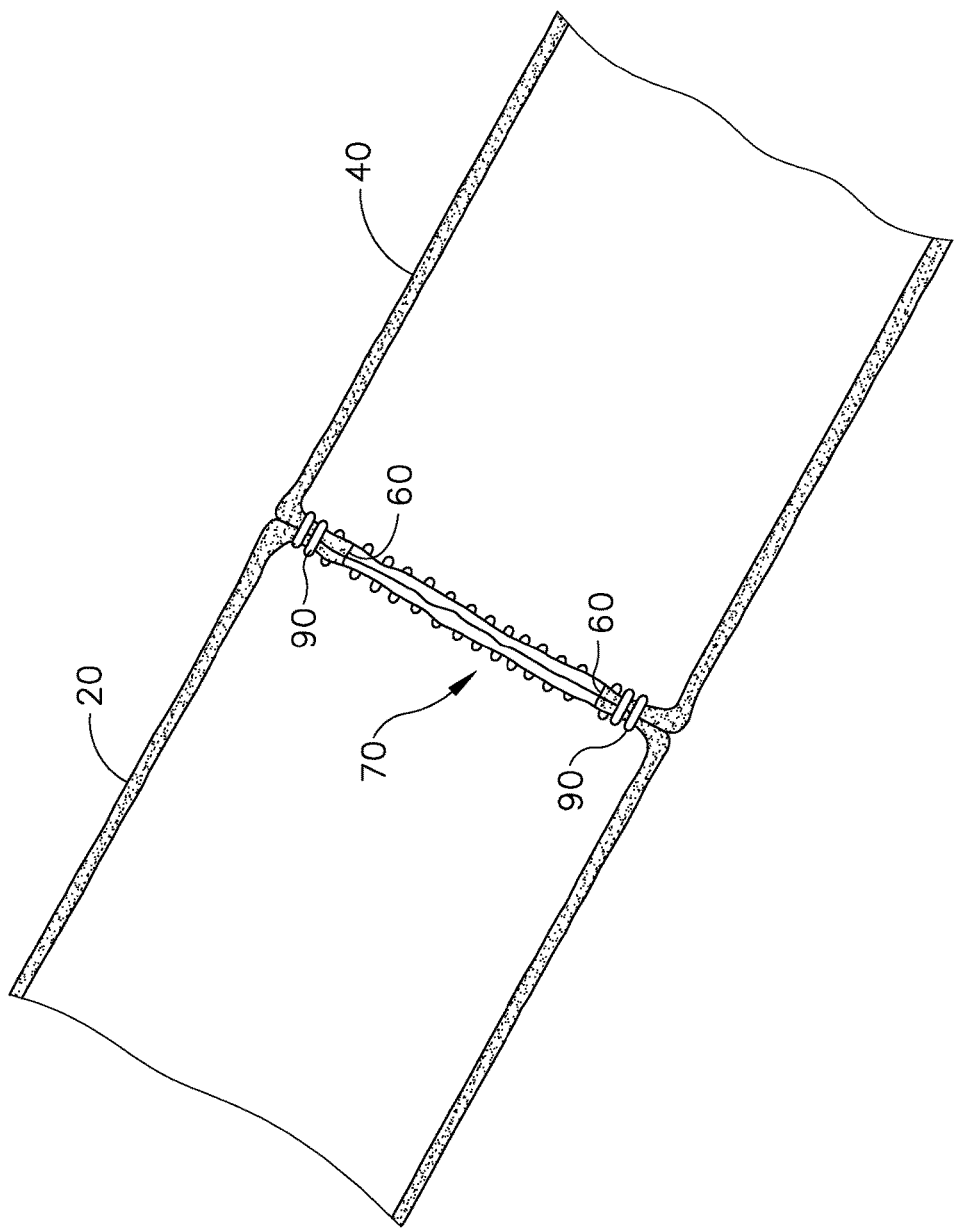
FIG. 21E depicts a cross-sectional side view of the first and second sections of the digestive tract of FIG. 21A joined together at an end-to-end anastomosis.

After the operator has actuated stapling head assembly (300) as shown in FIG. 21D, the operator rotates knob (130) to drive anvil (400) distally away from stapling head assembly (300), increasing the gap distance (d) to facilitate release of the tissue between surfaces (412, 322). The operator then removes instrument (10) from the patient, with anvil (400) still secured to trocar (330). Referring back to the example where the tubular anatomical structures (20, 40) comprise sections of a patient's colon, instrument (10) may be removed via the patient's rectum. With instrument (10) is removed, the tubular anatomical structures (20, 40) are left secured together by two annular arrays of staples (90) at an anastomosis (70) as shown in FIG. 21E. The inner diameter of the anastomosis (70) is defined by the severed edge (60) left by knife member (340).

II. Exemplary Alternative Instruments with Bailout Features

Although anvil (400) of instrument (10) is described above as being adjustable and/or movable in response to rotation of knob (130), it may be desirable in some instances to provide additional control over movement of anvil (400). In particular, it may be desirable to provide a bailout feature that is operable to quickly release anvil (400) from a retracted position to thereby quickly decompress tissue that is disposed between opposing surfaces (412, 322) of anvil (400) and stapling head assembly (300). The bailout features described herein may be desirable because an operator may encounter circumstances creating the need or desire to immediately abort an anastomosis procedure, once such a procedure has begun. While various alternative instruments are described below, other examples will be apparent to those of ordinary skill in the art in view of the teachings herein. It should be further understood that various features and/or structures of the instruments described below may be readily incorporated with other instruments described herein.

A. Exemplary Instrument with Threaded Bailout Mechanism

Figure 22:
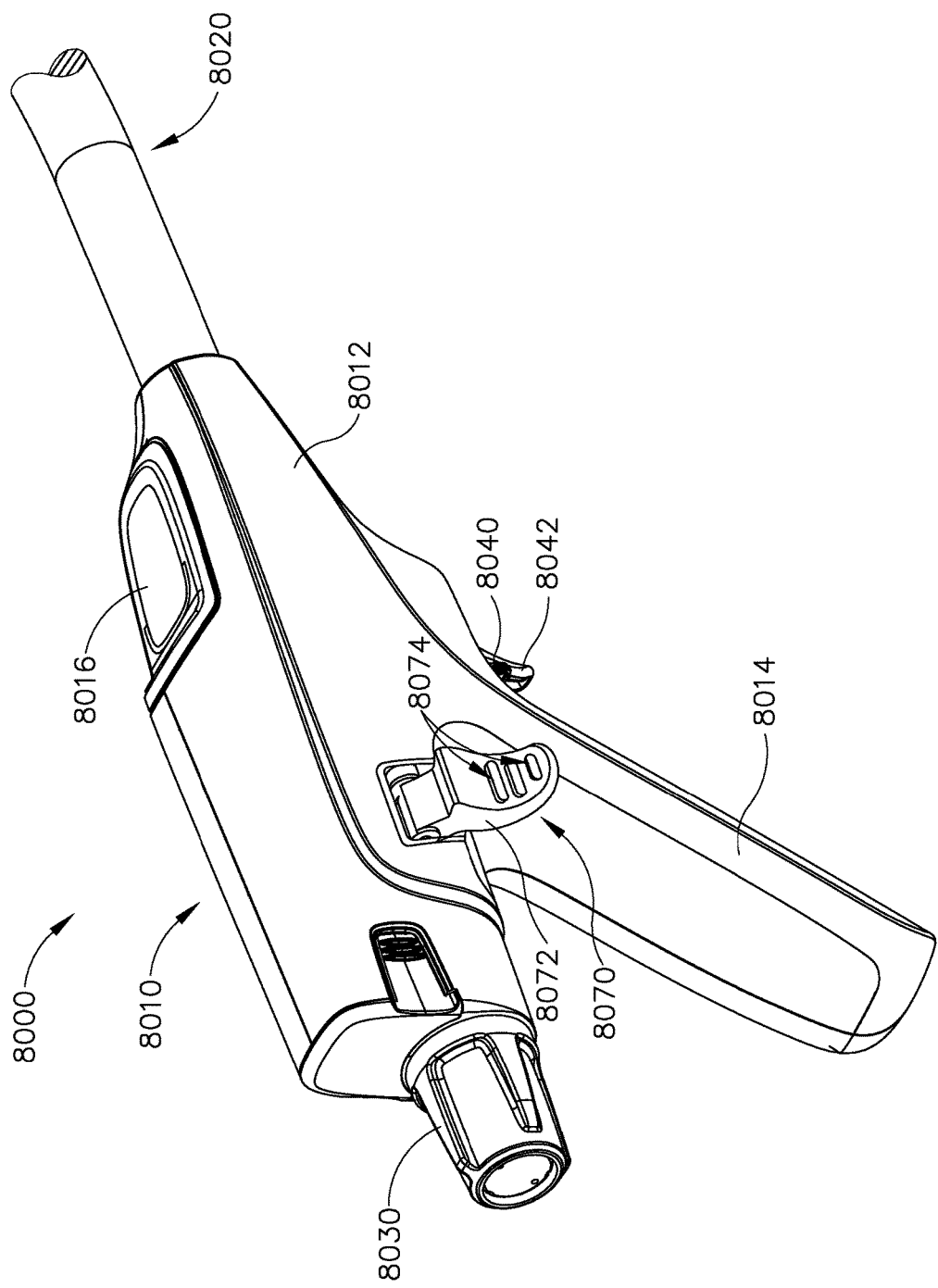
FIG. 22 depicts a partial perspective view of a handle assembly of exemplary alternative circular stapler.

FIG. 22 shows an exemplary alternative surgical circular stapling instrument (8000) that may be used to provide an end-to-end anastomosis between two sections of an anatomical lumen such as a portion of a patient's digestive tract. It should be understood that instrument (8000) of the present example is substantially the same as instrument (10) described above unless otherwise noted herein. For instance, like with instrument (10), instrument (8000) comprises a handle assembly (8010), a shaft assembly (8020), a stapling head assembly (not shown), and an anvil (not shown). Handle assembly (8010) is substantially the same has handle assembly (110) described above and comprises a casing (8012) defining an obliquely oriented pistol grip (8014). Handle assembly (8010) further includes a window (8016) that permits viewing of a movable indicator needle (not shown) as similarly described above.

Like with instrument (10) described above, instrument (8000) is controlled by an operator via knob (8030) and triggers (8040, 8042). Knob (8030), like with knob (130) described above, is operatively connected to shaft assembly (8020) to actuate the anvil. In particular, knob (8030) is rotatable to engage threads (not shown) of shaft assembly (8020) to translate a trocar actuation rod (8022), which ultimately actuates the anvil as similarly described above with respect to shaft assembly (200) of instrument (10).

Triggers (8040, 8042) function similarly as triggers (140, 150) described above. For instance, a safety trigger (8040) may be first actuated by an operator to permit activation of the stapling head assembly. Instrument (8000) further includes a firing trigger (8042), which is similar to firing trigger (150) described above. In particular, once safety trigger (8040) has been activated, firing trigger (8042) is operable to initiate actuation of the stapling head assembly. Firing trigger (8042) includes a paddle (not shown), which is configured to engage a motor activation module (not shown) when firing trigger (8042) is advanced by an operator. Like with motor activation module (180) described above, the motor activation module of the present example initiates the stapling sequence by activating a motor (not shown). The motor then drives a cam member (not shown), which in turn drives a cam follower (8054). The cam member and cam follower (8054) are substantially the same as cam member (700) and cam follower (600) described above, such that the cam member and cam follower (8054) operate cooperatively to drive the stapling head assembly through a stapling sequence.

Figure 23:
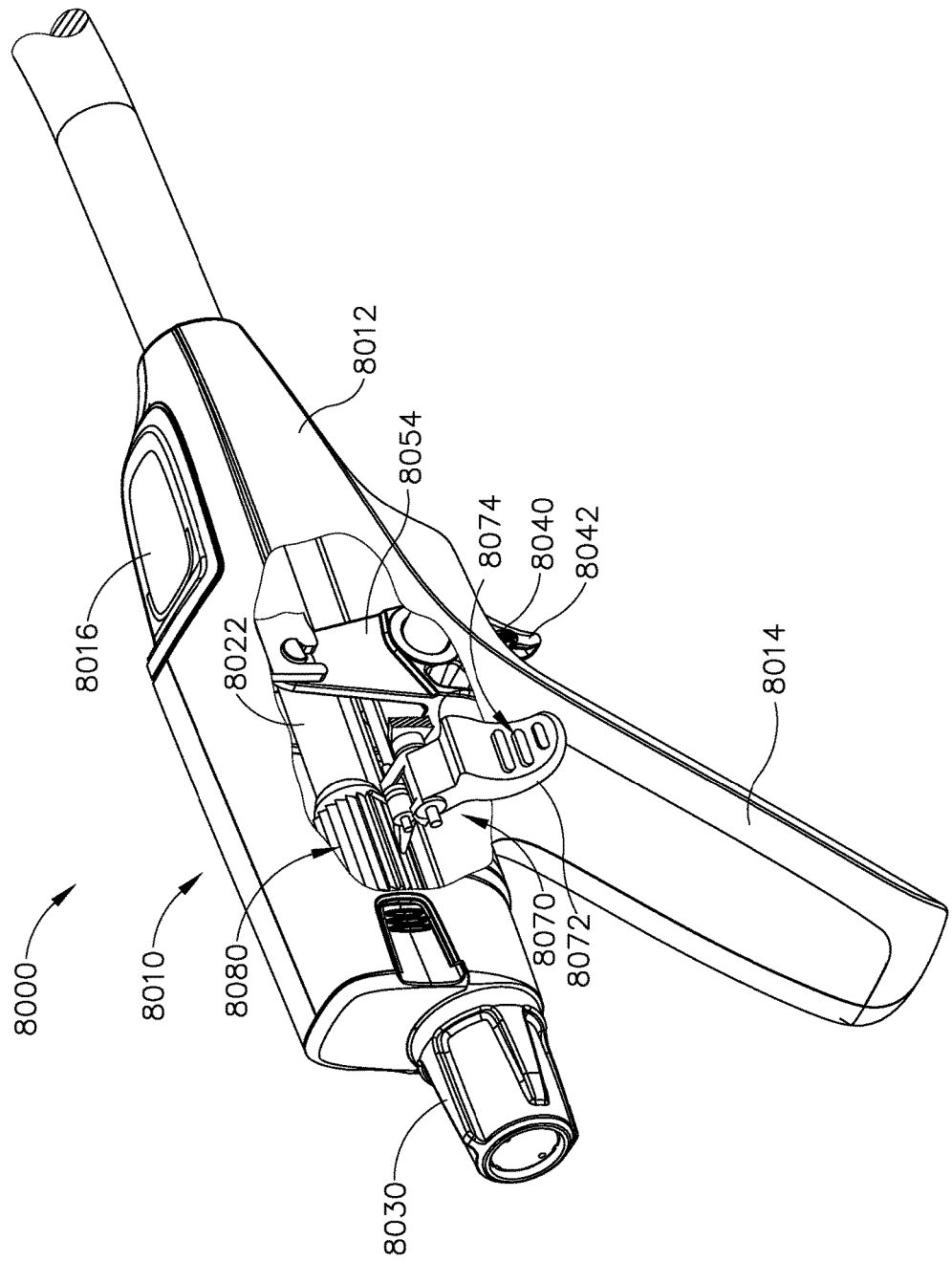
FIG. 23 depicts a perspective cut-away view of the circular stapler of FIG. 22, with an anvil bailout assembly in a neutral position visible.

Unlike instrument (10) described above, instrument (8000) of the present example comprises an anvil bailout assembly (8070). Anvil bailout assembly (8070) is generally configured to permit the trocar and anvil to be quickly disengaged by releasing tension in trocar actuation rod (8022) after the trocar and anvil have been adjusted via knob (8030). Such a feature may be desirable because an operator may desire to quickly release any compressive force supplied by the anvil during an anastomosis procedure. As can be seen in FIG. 23, anvil bailout assembly (8070) comprises a release member (8072), a pawl member (8076), and a coupling member (8080). Release member (8072) extends through casing (8012) of handle assembly (8010) and is configured for grasping by an operator. In particular, release member (8072) includes a plurality of gripping features (8074), which are configured to permit grasping by an operator to pivot release member (8072) relative to handle assembly (8010). As will be described in greater detail below, release member (8072) is generally pivotable relative to handle assembly (8010) to drive anvil bailout assembly (8070) to release tension in trocar actuation rod (8022), thereby releasing the trocar and anvil.

Figure 24:
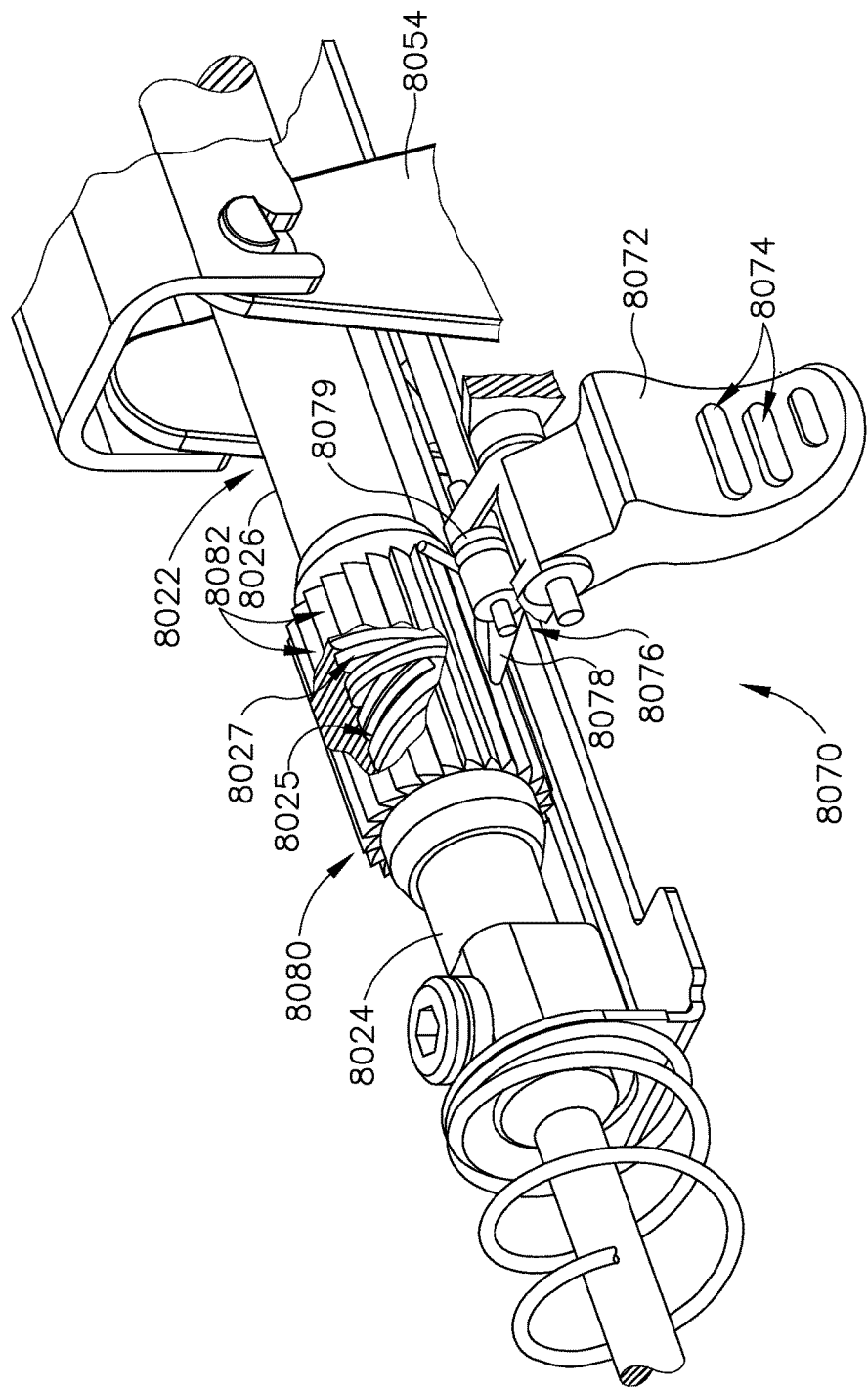
FIG. 24 depicts a detailed perspective view of the anvil bailout assembly of FIG. 23.

Pawl member (8076) is in communication with release member (8070). As is best seen in FIG. 24, pawl member (8076) includes an engagement portion (8078) that is generally configured to drive anvil bailout assembly (8070) via pivotable movement of release member (8072). In particular, pawl member (8076) is coupled to release member (8072) such that pivoting of release member (8072) in a counter clockwise direction results in corresponding pivoting of pawl member (8076) in a counter clockwise direction. Pivoting of pawl member (8076) in a counter clockwise direction results in engagement portion (8078) applying a driving force to coupling member (8080), as will be described in greater detail below.

Pawl member (8076) further includes a resilient member (8079). In the present example resilient member (8079) is a coil spring that is configured to resiliently bias pawl member (8076) toward the position shown in FIG. 24. As will be described in greater detail below, resilient member (8079) is configured to maintain engagement between engagement portion (8078) of pawl member (8076) and at least a portion of coupling member (8080).

Figure 25:
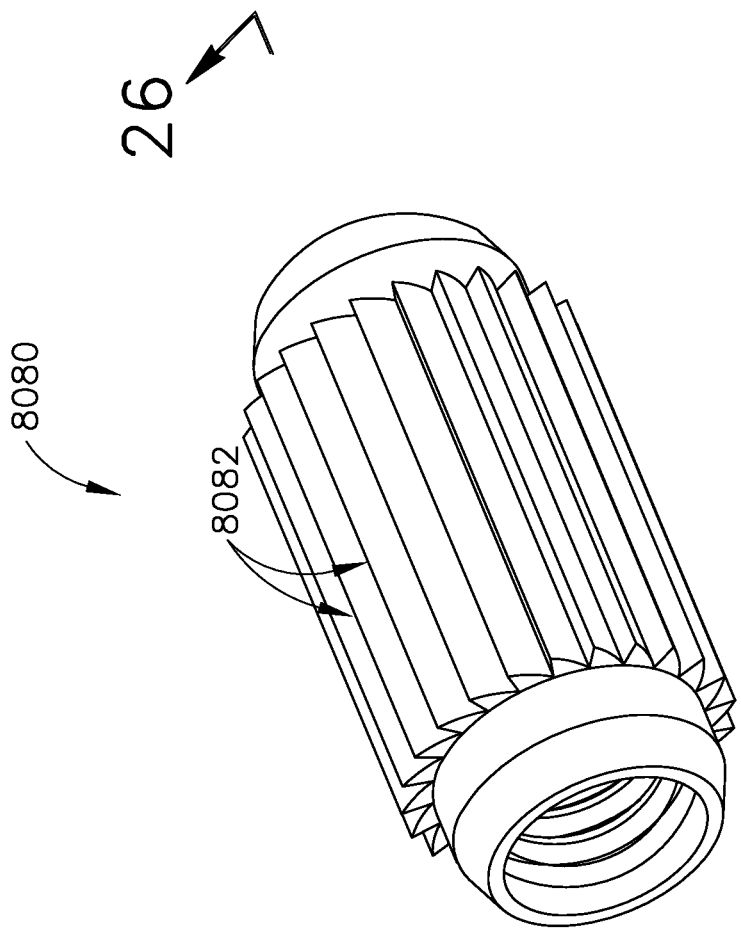
FIG. 25 depicts a detailed perspective view of a coupling member of the anvil bailout assembly of FIG. 23.
Figure 26:
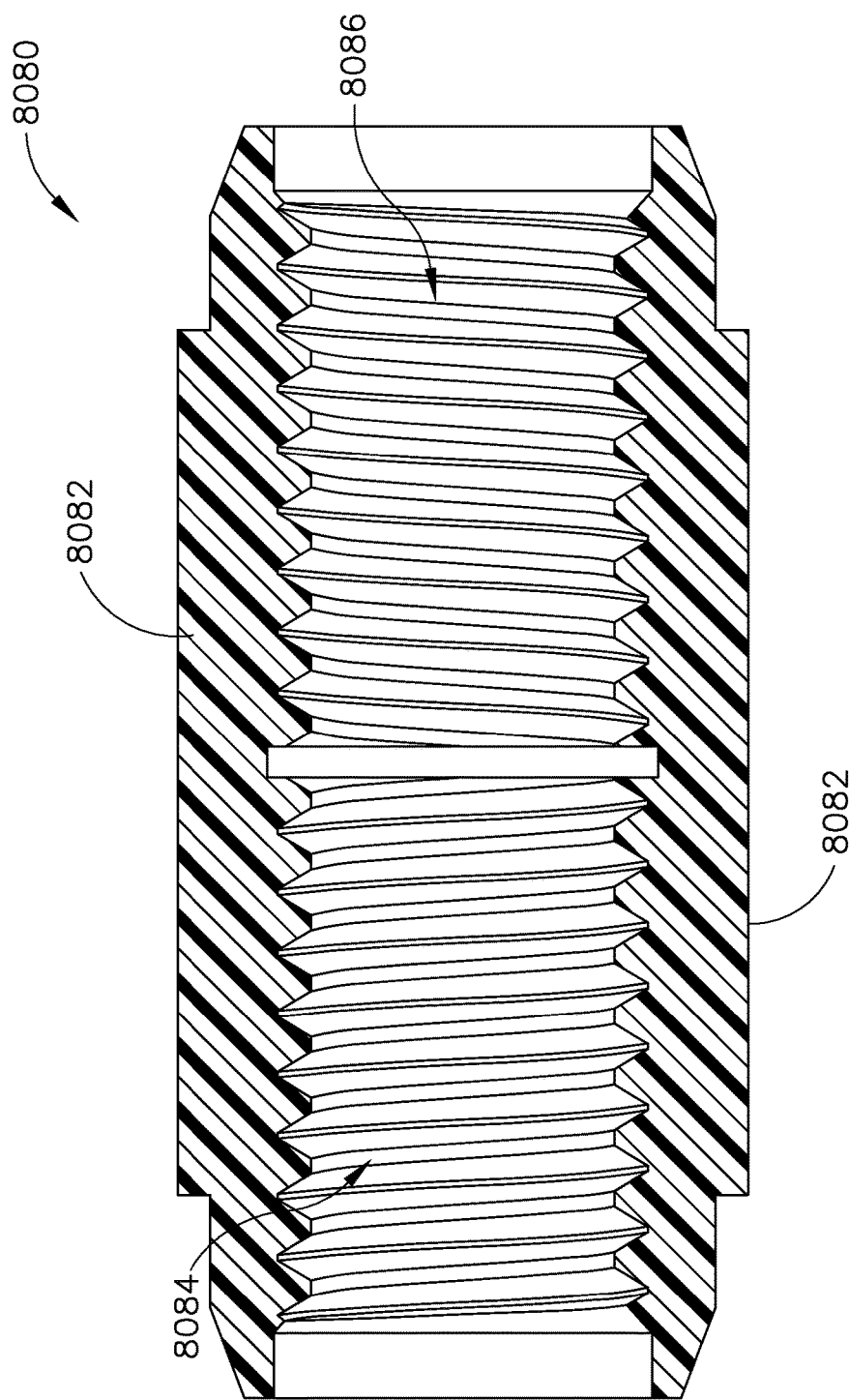
FIG. 26 depicts side cross-sectional view of the coupling member of FIG. 25, with the cross-section taken along line 26-26 of FIG. 25.

Coupling member (8080) is shown in FIGS. 25 and 26. As can be seen, coupling member (8080) comprises a generally cylindrical sheath. As will be described in greater detail below, coupling member (8080) is generally configured to be rotatably driven by pawl member (8076) relative to trocar actuation rod (8022) to expand the effective length of trocar actuation rod (8022). The outer diameter of coupling member (8080) comprises a plurality of tangentially oriented, longitudinally extending ratchet teeth (8082). Ratchet teeth (8082) of the present example are generally triangular and are configured to engage with pawl member (8076) to create a pawl and ratchet mechanism. Accordingly, each ratchet tooth (8082) is oriented in a particular tangential direction to sucessively engage pawl member (8076) as pawl member (8076) is used to advance coupling member (8080).

The interior of coupling member (8080) is shown in FIG. 26. As can be seen, the inner diameter of coupling member (8080) includes two sets of threads (8084, 8086) disposed therein. Each set of threads (8084, 8086) are generally the same, except threads (8084) have a pitch orientation that is opposite to the pitch orientation of threads (8086). As will be described in greater detail below, the opposing nature of threads (8084, 8086) is configured to engage with corresponding threads (8025, 8027) of trocar actuation rod (8022) to couple trocar actuation rod (8022) and lengthen or shorten the effective length of trocar actuation rod (8022).

Figure 27:
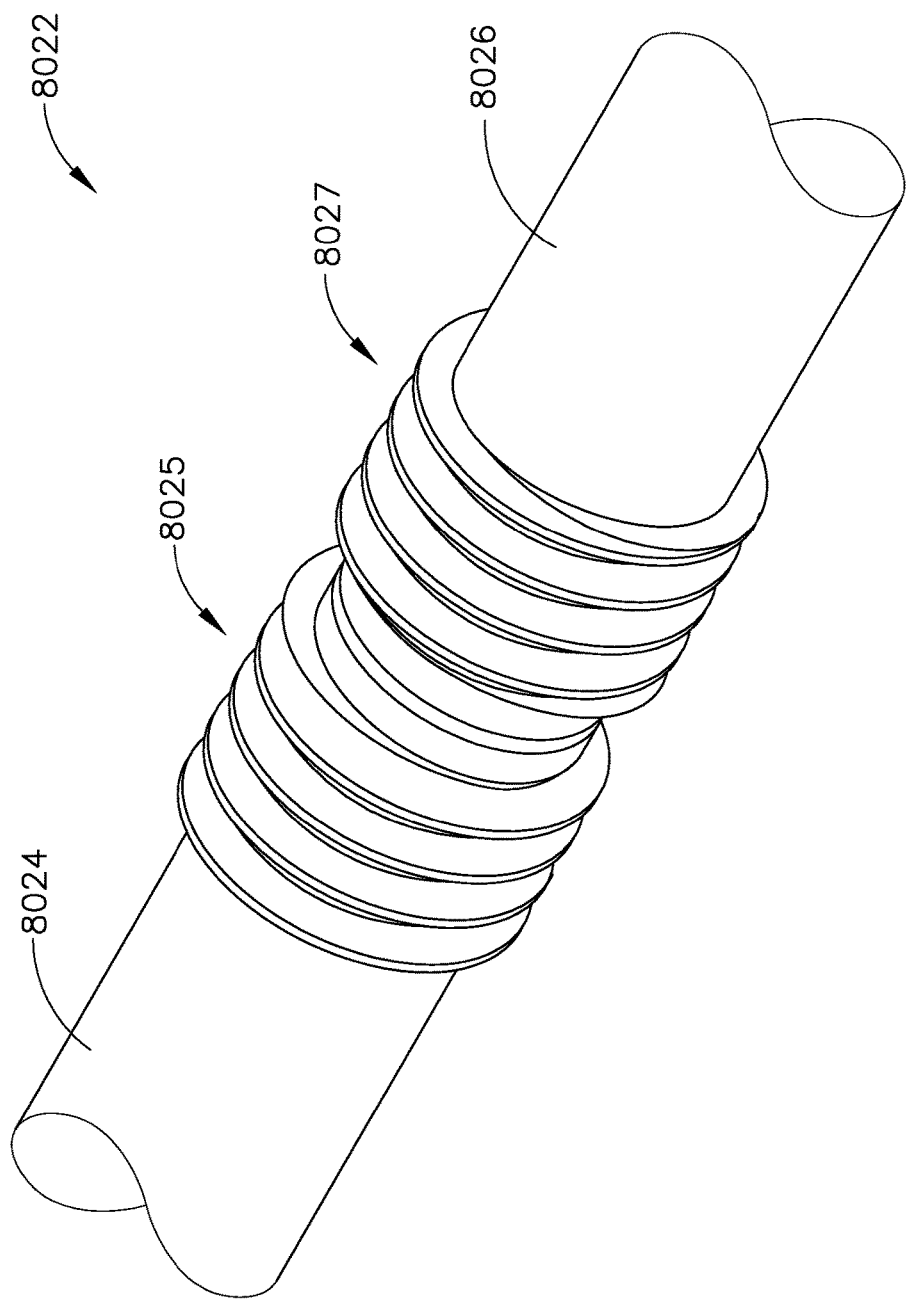
FIG. 27 depicts a detailed perspective view of a trocar actuation rod of the circular stapler of FIG. 22.

As can be seen in FIG. 27, trocar actuation rod (8022) comprises a proximal part (8024) and a distal part (8026). Each part (8024, 8026) is a discrete shaft that forms a single whole. Trocar actuation rod (8022) is thus formed by coupled parts (8024, 8026) via coupling member (8080). The distal end of proximal part (8024) includes a threaded portion (8025) and is configured to abut the proximal end of distal part (8026). Similarly, the proximal end of distal part (8026) includes a threaded portion (8027) and is configured to abut the distal end of proximal part (8024).

Each threaded portion (8025, 8027) is configured to engage with corresponding threads (8084, 8086) of coupling member (8080). Thus, threaded portions (8025, 8027) are likewise configured with opposing pitch orientations. Because of this, it should be understood that rotation of coupling member (8080) relative to parts (8024, 8026) will generally result in opposing longitudinal translation of each part (8024, 8026) of trocar actuation rod (8022). By way of example only, threaded portions (8025, 8027) and threads (8084, 8086) of the present example are configured such that clockwise rotation of coupling member (8080) results in each part (8024, 8026) of trocar actuation rod (8022) moving away from the other. Similarly, counter clockwise rotation of coupling member (8080) will result in each part (8024, 8026) of trocar actuation rod (8022) moving closer to the other. Although threaded portions (8025, 8027) and threads (8084, 8086) of the present example are described herein as having a particular relationship with rotation of coupling member (8080), it should be understood that no such limitation is intended and in other examples coupling member may be configured to have any suitable relationship as will be apparent to those of ordinary skill in the art in view of the teachings herein.

Figure 28:
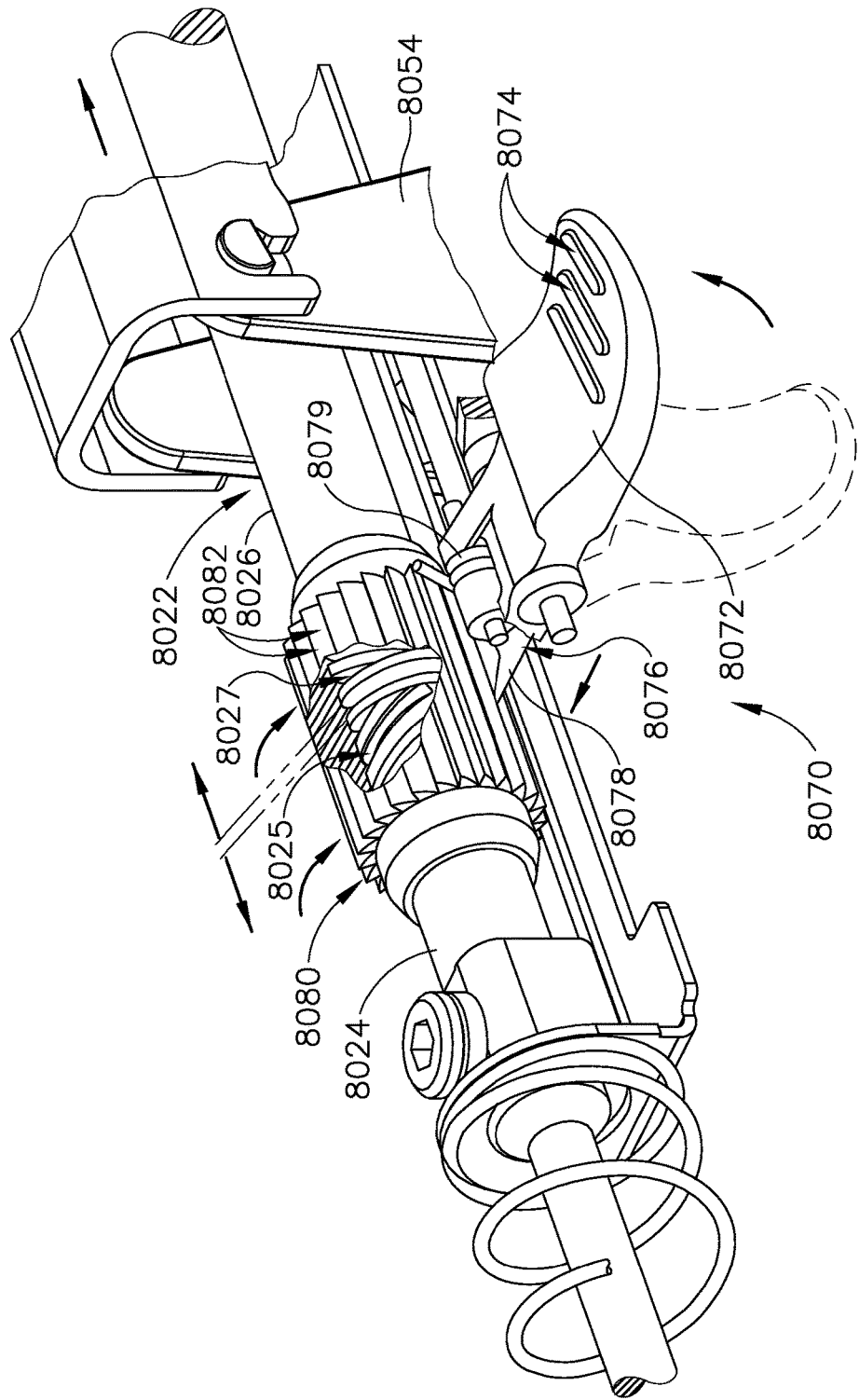
FIG. 28 depicts a detailed perspective view of the anvil bailout assembly of FIG. 23, with the anvil bailout assembly in a released position.

An exemplary mode of operation of anvil bailout assembly (8070) can be seen by comparing FIGS. 24 and 28. As can best be seen in FIG. 24, anvil bailout assembly (8070) is initially in a neutral state. It should be understood that in the neutral state anvil bailout assembly (8060) generally has no impact on the functioning of instrument (8000). In particular, coupling member (8080) is positioned via anvil bailout assembly (8070) such that proximal part (8024) of trocar actuation rod (8022) abuts distal part (8026) of trocar actuation rod (8022) such that trocar actuation rod (8022) comprises a length that is substantially the same as trocar actuation rod (220) described above. Correspondingly, release member (8072) is disposed in a position that is generally downwardly oriented to position pawl member (8076) away from coupling member (8080). In other words, pawl member (8076) does not contact teeth (8082) or any other portion of coupling member (8080) during rotation of knob (8030) to adjust the longitudinal position of the trocar and anvil relative to the stapling head assembly via trocar actuation rod (8022).

In some instances, an operator may desire to quickly bail out of an anastomosis procedure. This may require quickly releasing the trocar and anvil to unload the compression on tissue that is clamped between the anvil and the stapling head assembly. To quickly release the trocar and anvil, the operator may generally grasp release member (8072) and pull release member (8072) upwardly, as shown in FIG. 28. Movement of release member (8072) upwardly drives pawl member (8076) into engagement with a tooth (8082) of coupling member (8080), such that pawl member (8076) causes coupling member (8080) to rotate about the longitudinal axis of trocar actuation rod (8022). In the present example, coupling member (8080) is driven in a clockwise direction. Trocar actuation rod (8022) remains rotationally stationary while this occurs.

As described above, threads (8084, 8086) of coupling member (8080) are configured to engage threaded portions (8025, 8027) of trocar actuation rod (8022). Due to the opposing pitch orientations of threads (8025, 8027, 8084, 8086), the above-described rotation of coupling member (8080) relative to trocar actuation rod (8022) urges parts (8024, 8026) longitudinally away from each other. As proximal and distal parts (8024, 8026) are driven apart, this increases the effective length of trocar actuation rod (8022), relieving some of the compression being applied to the tissue by the anvil against the stapling head assembly.

The operator may push release member (8072) downwardly back to the position shown in FIG. 24, causing pawl member (8078) to ratchet along the tooth (8082) without causing corresponding rotation of coupling member (8080).

The operator may then again pull release member (8072) upwardly to the position shown in FIG. 28, causing pawl member (8076) to engage the next tooth (8082) and thereby rotate coupling member (8080) yet again relative to trocar actuation rod (8022), thereby driving parts (8024, 8026) longitudinally away from each other by another increment. The operator may repeat this process as many times as desired to incrementally increase the effective length of trocar actuation rod (8022), thereby incrementally decreasing the compression being applied to the tissue by the anvil against the stapling head assembly. With the tension on the anvil by trocar actuation rod (8022) being relieved, the operator may more easily extract instrument (8000) from the patient without causing damage to surrounding tissue.

It should be understood that rotating member (8080) has sufficient length such that pawl member (8076) may engage teeth (8082) while rotating member (8080) and trocar actuation rod (8022) are at various different longitudinal positions. In other words, anvil bailout assembly (8070) may be effectively operated before the anvil significantly compresses tissue against the stapling head assembly. It should also be understood that in some examples anvil bailout assembly (8070) may include gears, levers, or other features to create a mechanical advantage between the movement of release member (8072) and the movement of pawl member (8076). Other suitable variations will be apparent to those of ordinary skill in the art in view of the teachings herein.

B. Exemplary Instrument with Pin Release Bailout Features

Figure 29:
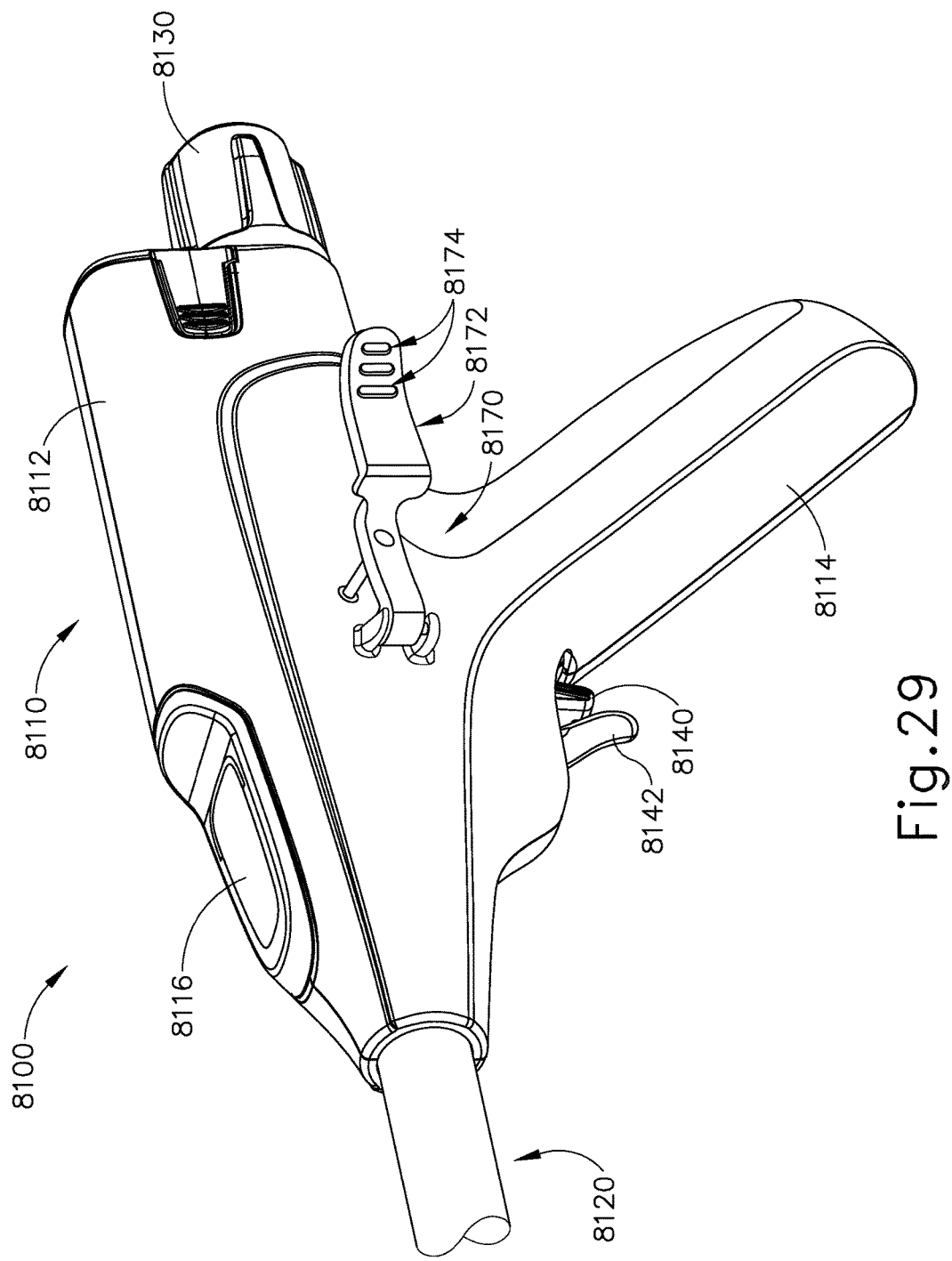
FIG. 29 depicts a detailed perspective view of a handle assembly of another exemplary alternative circular stapler.
Figure 30:
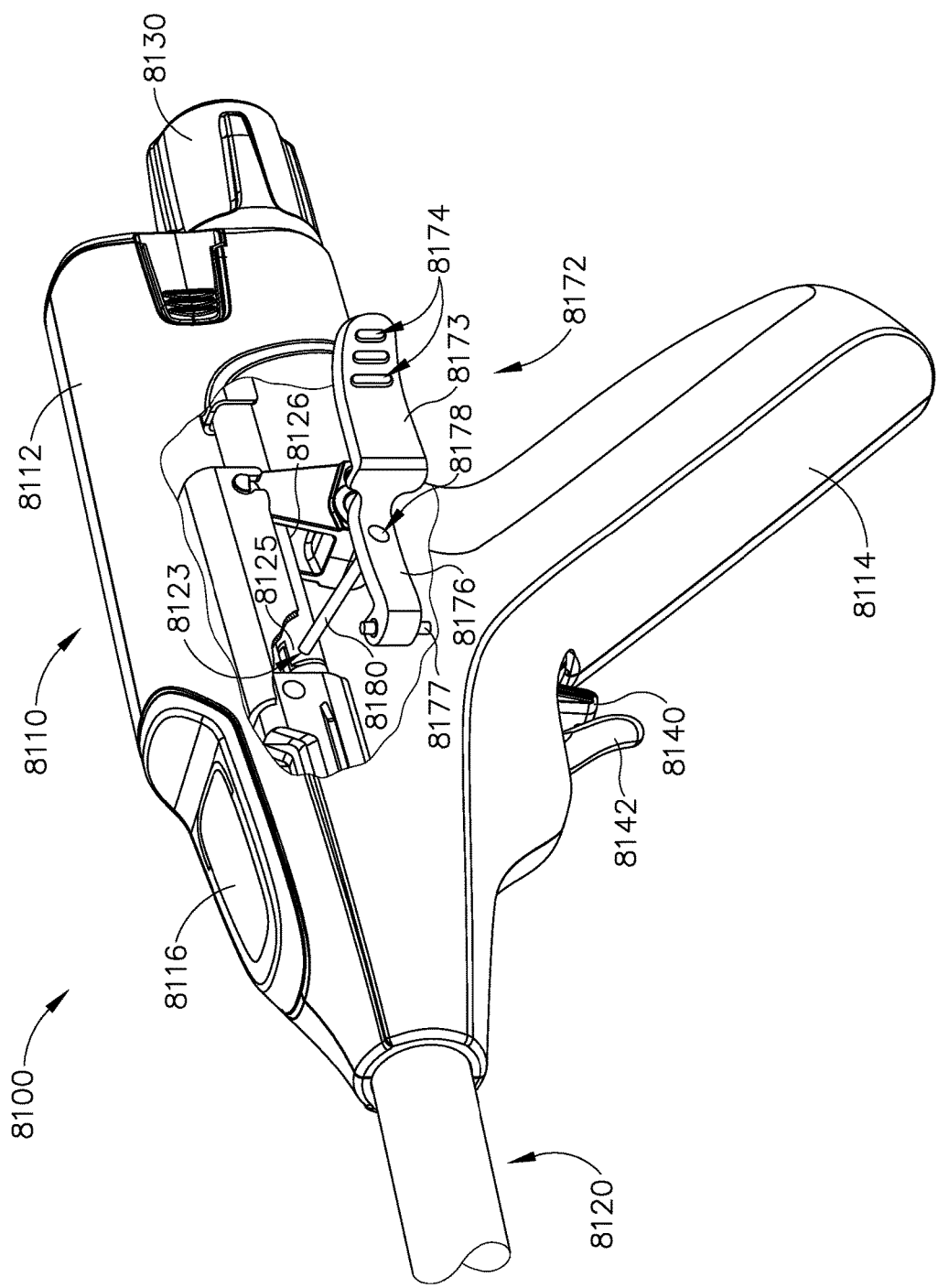
FIG. 30 depicts a perspective cut-away view of the circular stapler of FIG. 29, with an anvil bailout assembly in a neutral position visible.

FIGS. 29-30 show an exemplary alternative surgical circular stapling instrument (8100) that may be used to provide an end-to-end anastomosis between two sections of an anatomical lumen such as a portion of a patient's digestive tract. It should be understood that instrument (8100) of the present example is substantially the same as instrument (10) described above unless otherwise noted herein. For instance, like with instrument (10), instrument (8100) comprises a handle assembly (8110), a shaft assembly (8120), a stapling head assembly (not shown), and an anvil (not shown). Handle assembly (8110) is substantially the same has handle assembly (110) described above and comprises a casing (8112) defining an obliquely oriented pistol grip (8114). Handle assembly (8110) further includes a window (8116) that permits viewing of a movable indicator needle (not shown) as similarly described above.

Like with instrument (10) described above, instrument (8100) is controlled by an operator via knob (8130) and triggers (8140, 8142). Knob (8130), like with knob (130) described above, is operatively connected to shaft assembly (8120) to actuate the anvil. In particular, knob (8130) is rotatable to engage threads (not shown) of shaft assembly (8120) to translate a trocar actuation rod (8122), which ultimately actuates the anvil as similarly described above with respect to shaft assembly (200) of instrument (10).

Triggers (8140, 8142) function similarly as triggers (140, 150) described above. For instance, a safety trigger (8140) may be first actuated by an operator to permit activation of the stapling head assembly. Instrument (8100) further includes a firing trigger (8142), which is similar to firing trigger (150) described above. In particular, once safety trigger (8140) has been activated, firing trigger (8142) is operable to initiate actuation of the stapling head assembly. Firing trigger (8142) includes a paddle (not shown), which is configured to engage a motor activation module (not shown) when firing trigger (8142) is advanced by an operator. Like with motor activation module (180) described above, the motor activation module of the present example initiates the stapling sequence by activating a motor (not shown). The motor then drives a cam member (not shown), which in turn drives a cam follower (8154). The cam member and cam follower (8154) are substantially the same as cam member (700) and cam follower (600) described above, such that the cam member and cam follower (8154) operate cooperatively to drive the stapling head assembly through a stapling sequence.

Figure 31:
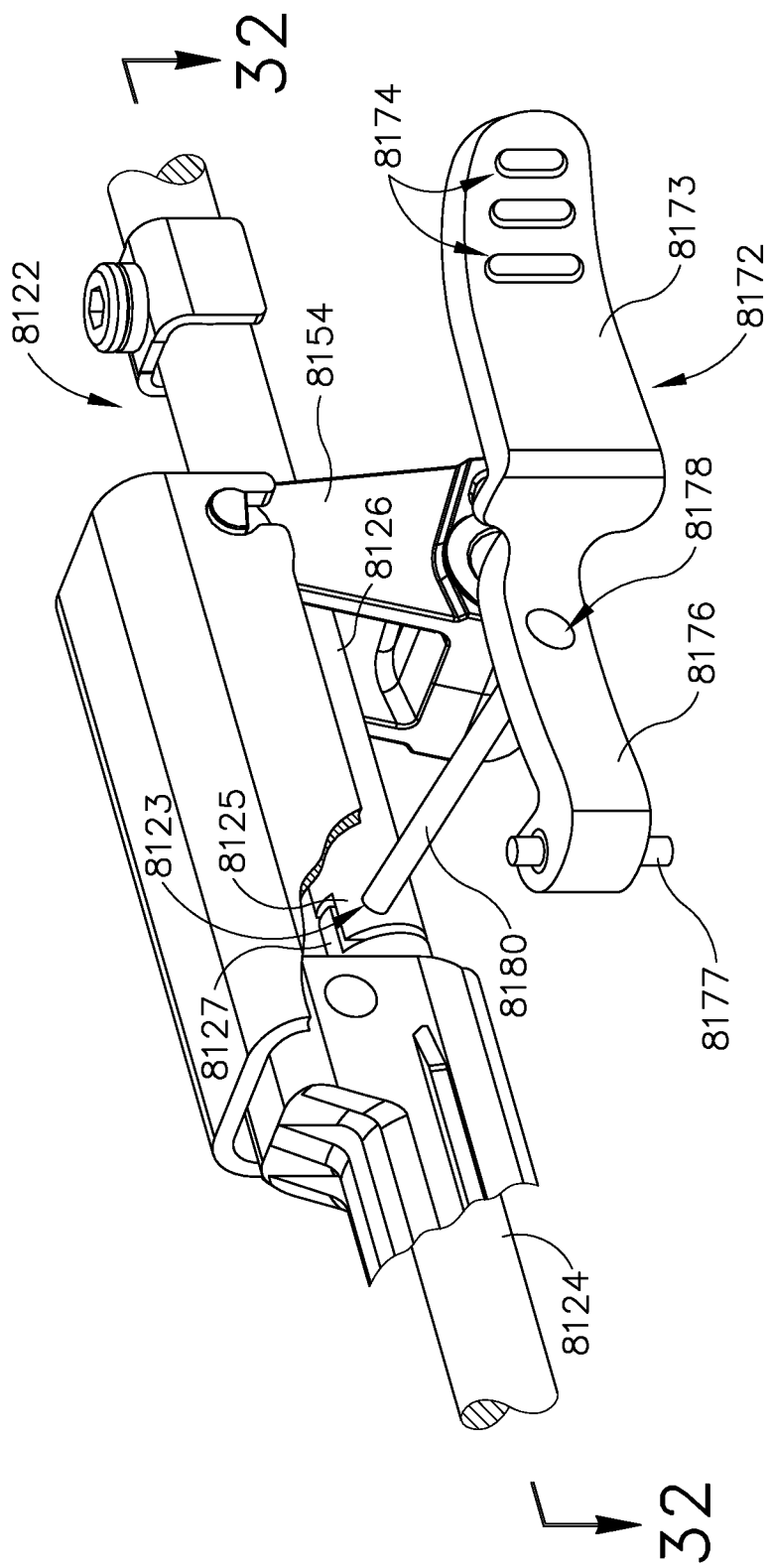
FIG. 31 depicts a detailed perspective view of the anvil bailout assembly of FIG. 30, with the anvil bailout assembly in the neutral position.

Unlike instrument (10) described above, instrument (8100) of the present example comprises an anvil bailout assembly (8170). Anvil bailout assembly (8170) is generally configured to permit the trocar and anvil to be quickly disengaged by releasing tension in trocar actuation rod (8122) after the trocar and anvil have been adjusted via knob (8130). Such a feature may be desirable because an operator may desire to quickly release any compressive force supplied by the anvil during an anastomosis procedure. As can be seen in FIG. 31, anvil bailout assembly (8170) comprises a release member (8172) and a coupling member (8180). Release member (8172) is disposed on the exterior of casing (8112) of handle assembly (8110) and is configured for grasping by an operator. In particular, release member (8172) comprises a gripping portion (8173) and a lever portion (8176). Gripping portion (8173) is configured to be grasped by an operator and includes a plurality of gripping features (8174) to improve the general grippability of gripping portion (8173).

Lever portion (8176) extends distally from gripping portion (8173) and is generally configured to permit release member (8072) to pivot relative to handle assembly (8110). The distal end of lever portion (8176) is pivotably secured to casing (8112) of handle assembly (8110) by a pin (8177) or other suitable pivotable coupling. Lever portion (8176) further includes a bore (8178) disposed distally of the proximal end of lever portion (8176). As will be described in greater detail below, bore (8178) is generally configured to secure coupling member (8180) to lever portion (8176). As will also be described in greater detail below, release member (8172) is generally pivotable relative to handle assembly (8110) to drive anvil bailout assembly (8170) to release tension in trocar actuation rod (8122), thereby releasing the trocar and anvil.

Figure 32:
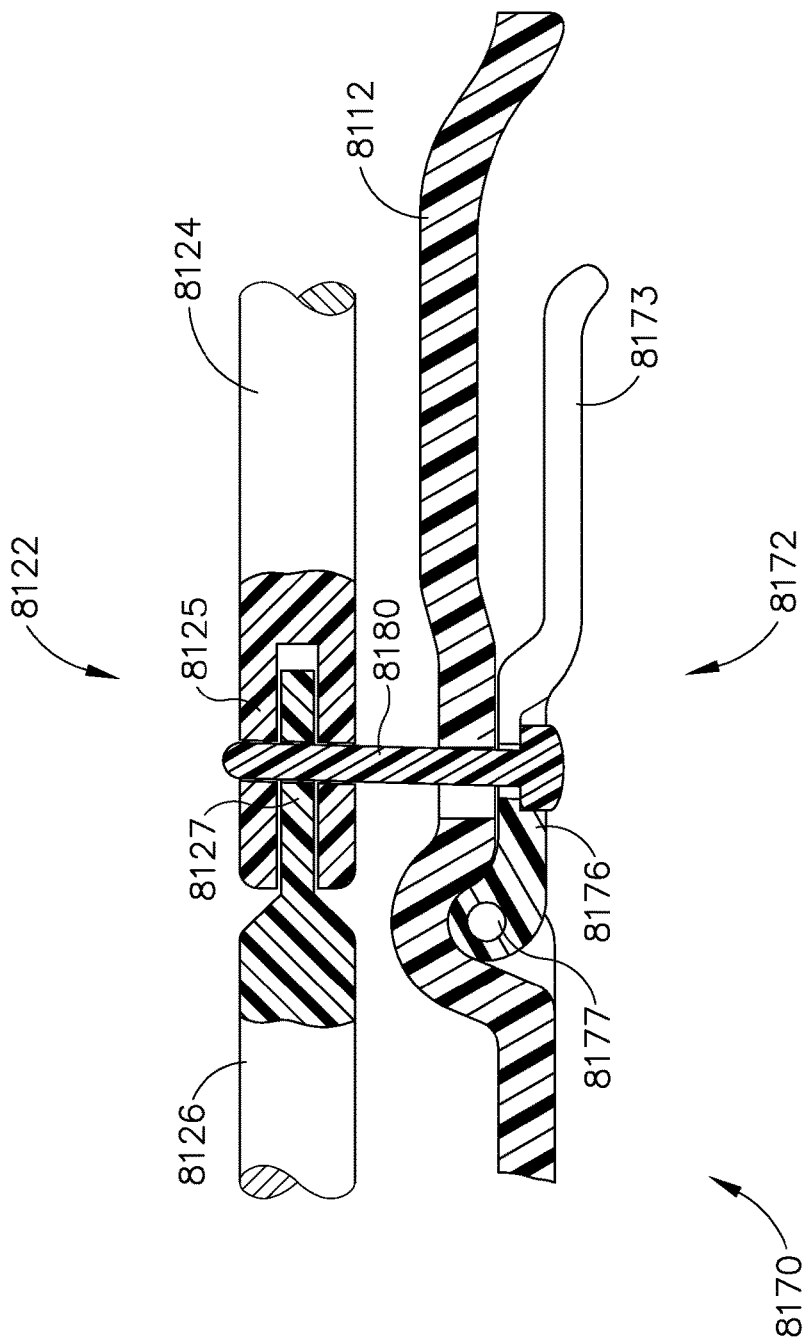
FIG. 32 depicts a detailed top cross-sectional view of the anvil bailout assembly of FIG. 30, with the cross-section taken along line 32-32 of FIG. 31 and the anvil bailout assembly in the neutral position.
Figure 33:
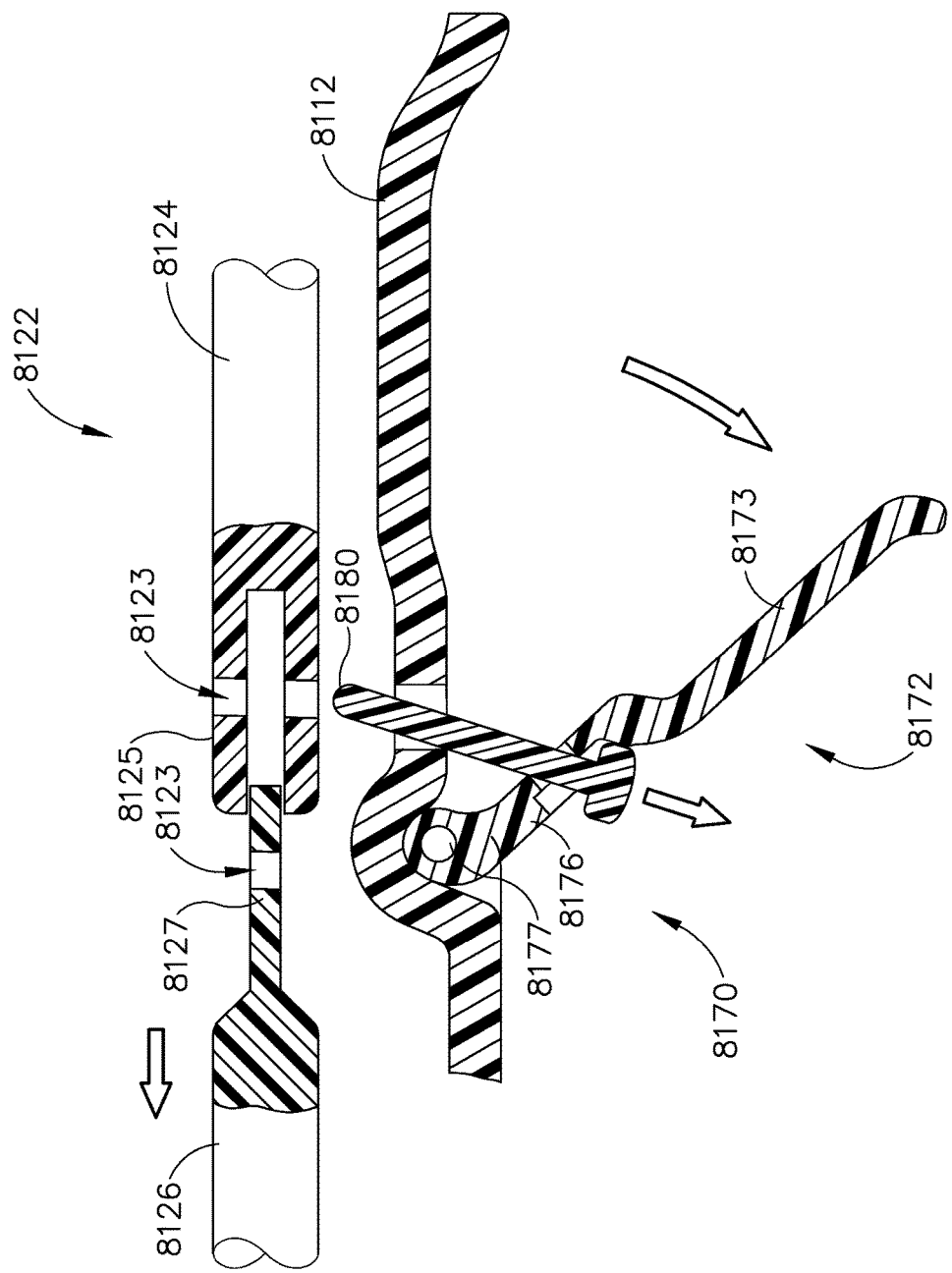
FIG. 33 depicts another detailed top cross-sectional view of the anvil bailout assembly of FIG. 30, with the cross-section taken along line 32-32 of FIG. 31 and the anvil bailout assembly in a released position.

Coupling member (8180) is shown in FIGS. 31-33. As can be seen, coupling member (8180) comprises a generally cylindrical pin. Coupling member (8180) extends laterally from lever portion (8176) of release member (8072). In particular, coupling member (8180) is disposed in bore (8178) of lever portion (8176). In the present example, coupling member (8180) is held in bore (8178) by an interference or friction fit. Additionally, adhesives, other bonding agents, and/or other features may be used to secure coupling member (8180) to lever portion (8176). Although coupling member (8180) is described herein as being a separate component from release member (8172), it should be understood that in some examples coupling member (8180) may be integral with release member (8172).

As will be described in greater detail below, coupling member (8180) is generally configured to be moved by release member (8172) relative to trocar actuation rod (8122) to decouple two parts (8124, 8126) of trocar actuation rod (8122). As is best seen in FIG. 32, coupling member (8180) extends laterally from lever portion (8176) of release member (8172) through an opening (8123) in trocar actuation rod (8122).

Similarly to trocar actuation rod (8022) described above, trocar actuation rod (8122) of the present example comprises a proximal part (8124) and a distal part (8126). However, unlike proximal part (8024) described above, proximal part (8124) of the present example comprises a slotted female end (8125), while distal part (8126) comprises an elongate male end (8127). As will be described in greater detail below, male end (8127) of distal part (8126) is configured to be inserted into female end (8125) of proximal part (8124) such that parts (8124, 8126) of trocar actuation rod (8122) may be releasably coupled by coupling member (8180). Trocar actuation rod (8122) translates longitudinally in response to rotation of knob (8130) to adjust the longitudinal position of the anvil and the trocar relative to the stapling head assembly. Since coupling member (8180) is disposed in both parts (8124, 8126) of trocar actuation rod (8122), coupling member (8180) will translate longitudinally with trocar actuation rod (8122). Casing (8112) may include a slot and/or any other suitable features to accommodate such translation of coupling member (8180) relative to casing (8112) as trocar actuation rod (8122) translates relative to casing (8112). In addition, casing (8112) may include a slot and/or any other suitable features to accommodate translation of release member (8172) that may occur relative to casing (8112) as coupling member (8180) and trocar actuation rod (8122) translate relative to casing. Thus, while bailout assembly (8170) is in a neutral position, bailout assembly (8170) holds parts (8124, 8126) together and allows trocar actuation rod (8122) to translate as the operator adjusts the position of the anvil and trocar.

FIGS. 32 and 33 show an exemplary mode of operation of anvil bailout assembly (8170). As can be seen in FIG. 32, anvil bailout assembly (8170) initially begins in a neutral position. In the initial position, anvil bailout assembly (8170) is positioned such that operation of instrument (8100) is not substantially impacted by anvil bailout assembly (8170). In particular, release member (8172) is disposed relatively flush with handle assembly (8110). With release member (8172) in such a position, coupling member (8180) is disposed in opening (8183) of trocar actuation rod (8122), thereby coupling proximal and distal ends (8124, 8126) of trocar actuation rod (8122) together. Although trocar actuation rod (8122) is coupled via coupling member (8180), it should be understood that trocar actuation rod (8122) remains relatively free to translate as the operator rotates knob (8130).

In some instances, an operator may desire to quickly bail out of an anastomosis procedure. This may require quickly releasing the trocar and anvil to unload the compression on tissue that is clamped between the anvil and the stapling head assembly. To release the trocar and anvil, the operator may transition anvil bailout assembly (8170) to a released position as shown in FIG. 33. As can be seen, to transition anvil bailout assembly (8170) to the released position, an operator may grasp gripping portion (8173) of release member (8172) and pull release member (8172) outwardly away from handle assembly (8110). Pulling release member (8172) outwardly causes release member (8172) to pivot about pin (8177). Such pivoting motion of release member (8172) correspondingly pulls coupling member (8180) out of opening (8123) in trocar actuation rod (8122). With coupling member (8180) pulled from opening (8123), distal part (8126) of trocar actuation rod (8122) is permitted to decouple from proximal part (8124) of trocar actuation rod (8122), thereby relieving compression being applied to the tissue by the anvil against the stapling head assembly.

In some instances it may be desirable for instrument (8100) to also include features to quickly release a cylindraceous knife member (8150), similar to cylindraceous knife member (340) described above. For instance, as described above with respect to knife member (340), knife member (8150) may be driven separately from the anvil. Thus, in such examples it may be desirable to include a knife bailout assembly (8190) to quickly release knife member (8150) in addition to or in lieu of anvil bailout assembly (8170).

Figure 34:
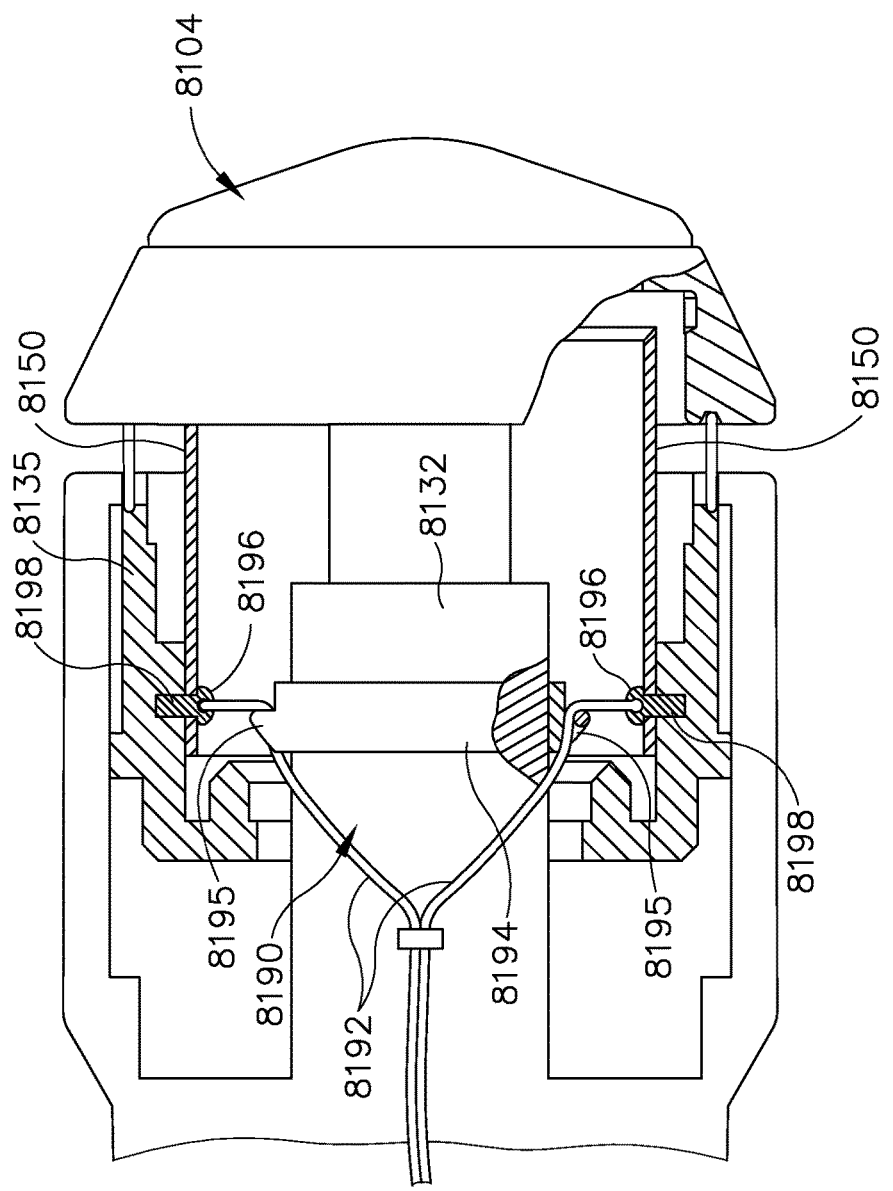
FIG. 34 depicts a detailed side cross-sectional view of a stapling head assembly of the circular stapler of FIG. 29, the stapling head assembly equipped with a knife bailout assembly.

FIG. 34 shows instrument (8100) of the present example equipped with knife bailout assembly (8190). Knife bailout assembly (8190) comprises a pair of cables (8192), a force director (8194), and a pair of pins (8196). Cables (8192) extend proximally from the distal end of shaft assembly (8120) to the handle assembly (8110). Although not shown, it should be understood that in the present example, the proximal end of cables (8192) are attachable to release member (8172) of anvil bailout assembly (8170) such that actuation of anvil bailout assembly (8170) also results in actuation of knife bailout assembly (8190). In examples where knife bailout assembly (8190) is included in lieu of anvil bailout assembly (8170), it should be understood that handle assembly (8110) may include features such as levers, triggers, or etc. that permit actuation of knife bailout assembly (8190) from handle assembly (8110). It should also be understood that, in examples where both anvil bailout assembly (8170) and knife bailout assembly (8190) are included, assemblies (8170, 8190) may be actuated by separate, independently operable release members.

The distal ends of cables (8192) are threaded through force director (8194). In particular, force director (8194) is secured to stationary inner core member (8132), which is similar to inner core member (312). Force director (8194) includes a pair of redirecting features (8195) that redirect each cable (8192) approximately 90° from a longitudinal travel direction to a transverse travel direction. As will be described in greater detail below, such a redirection permits cables (8192) to actuate pins (8196). Although not shown, it should be understood that redirecting features (8195) may comprise friction management features such as wheels, pulleys, ball bearings, etc. to permit cables (8192) to move smoothly with low friction over redirecting features (8195).

Each pin (8196) is attached to the distal end of a corresponding cable (8192). An outwardly extending portion (8198) of each pin (8196) extends laterally though an opening (8151) in knife member (8150) and into a staple driver member (8135), which is similar to staple driver member (350). Pins (8196) thus releasably couple knife member (8150) to staple driver member (8135). As will be described in greater detail below, pins (8196) generally function to permit knife member (8150) to function as similarly described above with respect to knife member (340) until knife bailout assembly (8190) is actuated by an operator. Knife member (8150) and staple driver member (8135) will operate just like knife member (340) and staple driver member (350) as described above when knife member (8150) is secured to staple driver member (8135) via pins (8196).

FIGS. 35-36 show an exemplary mode of operation of knife bailout assembly (8190). As can be seen in FIG. 35, knife bailout assembly (8190) is initially in a neutral state where knife bailout assembly (8190) does not generally impact the operation of instrument (8100). As can be seen, in the neutral state, each pin (8196) is positioned through knife member (8150) and into staple driver member (8135). This positioning permits the normal operation of knife member (8150) by permitting a feature of shaft assembly (8120) similar to stapling head assembly driver (240) to actuate knife member (8150) and staple driver member (8135) together. Each cable (8192) is correspondingly relatively free from tension to permit each pin (8196) to move along with knife member (8150). In other words, cables (8192) provide enough slack to freely accommodate distal travel of knife member (8150) and staple driver member (8135) as knife member (8150) and staple driver member (8135) are actuated during normal operation.

If an operator desires to release knife member (8150) to abort or otherwise bail out of an anastomosis procedure, an operator may actuate knife bailout assembly (8190) to the position shown in FIG. 36. FIG. 36 shows knife bailout assembly (8190) is in a released state. In the released state, each pin (8196) is pulled from opening (8151) of knife member (8150) such that knife member (8150) is no longer held in position by each pin (8196). To pull each pin (8196) from opening (8151) of knife member (8150), the operator may apply tension to each cable (8192) by pulling proximally on cables (8192). In examples where knife bailout assembly (8190) is included in addition to anvil bailout assembly (8170), cables (8192) may be pulled by actuating release member (8172) of anvil bailout assembly (8170) or by actuating a separate feature that is independent of anvil bailout assembly (8170). In examples where knife bailout assembly (8190) is included in lieu of anvil bailout assembly (8170), the tensioning of cables (8192) may comprise actuating a lever arm, wheel, or other feature. Alternatively, cables (8192) may merely extend from handle assembly (8110) and an operator may simply pull directly on cables (8192) themselves.

When knife bailout assembly (8190) is in a released state, tissue that has not yet been cut by knife member (8150) may drive knife member (8150) proximally to or toward the position shown in FIG. 36. In some versions where an anvil bailout assembly (8170) is included in addition to a knife bailout assembly (8190), the operator may wish to actuate knife bailout assembly (8190) first and then actuate anvil bailout assembly (8170). This may facilitate removal of anvil (8104) from the patient, particularly when non-severed tissue might otherwise be stuck between knife member (8150) and anvil (8104).

III. Exemplary Alternative Bailout Features

A. Exemplary Bailout Door

Figure 37:
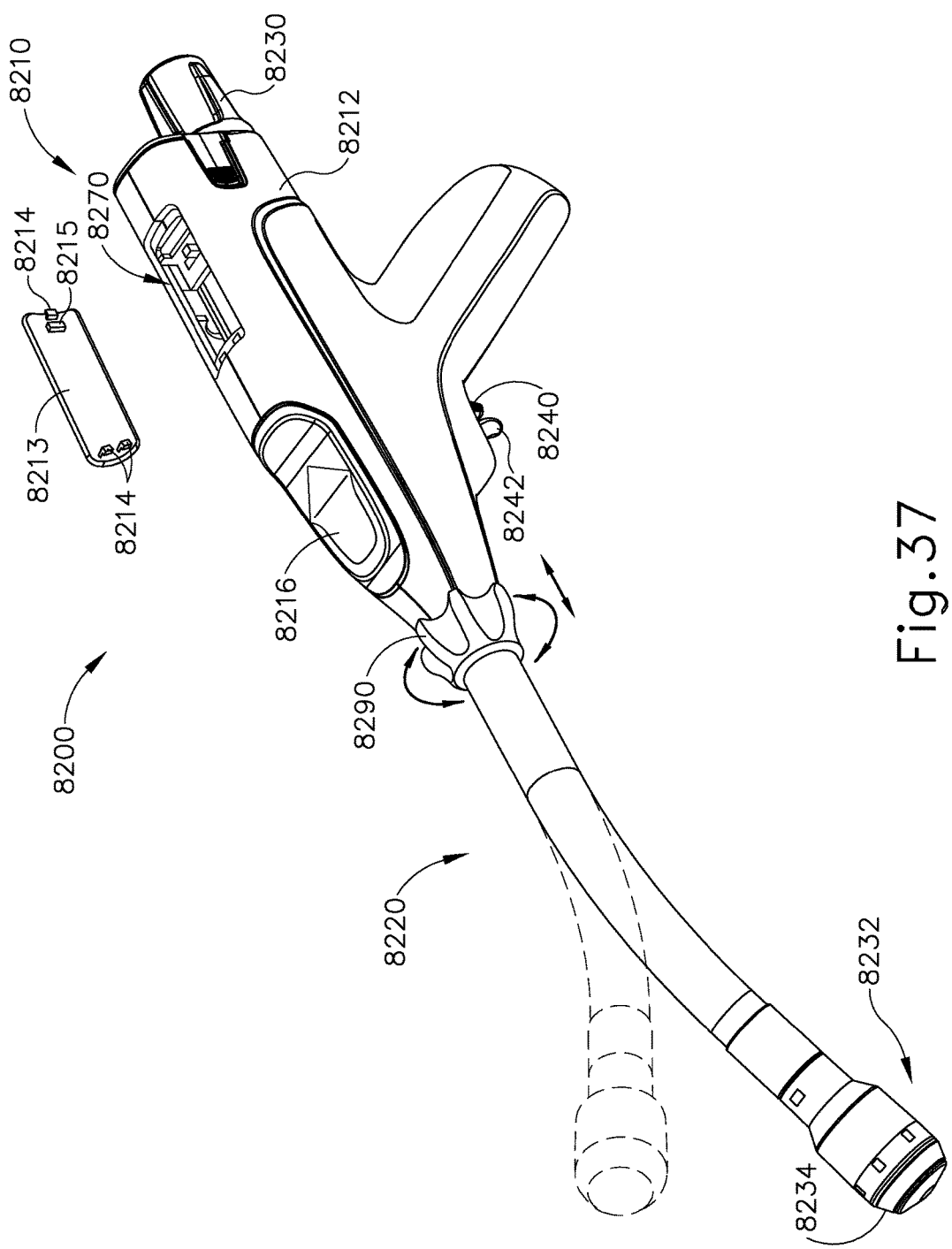
FIG. 37 depicts a perspective view of still another exemplary alternative circular stapler, with a bailout door removed.

FIG. 37 shows still another exemplary alternative instrument (8200) that may be used to provide an end-to-end anastomosis between two sections of an anatomical lumen such as a portion of a patient's digestive tract. It should be understood that instrument (8200) of the present example is substantially the same as instrument (10) described above unless otherwise noted herein. For instance, like with instrument (10), instrument (8200) comprises a handle assembly (8210), a shaft assembly (8220), and a stapling head assembly (8232). Handle assembly (8210) comprises a casing (8212) and is substantially the same has handle assembly (110) described above such that further details will not be described herein.

Like with instrument (10) described above, instrument (8200) is controlled by an operator via knob (8230) and triggers (8240, 8242). Knob (8230), like with knob (130) described above, is operatively connected to shaft assembly (8220) to actuate an anvil (8234) of stapling head assembly (8232). In particular, knob (8230) is rotatable to engage threads (not shown) of the shaft assembly to translate a trocar actuation rod (not shown), which ultimately actuates anvil (8234) as similarly described above with respect to shaft assembly (200) of instrument (10).

Triggers (8240, 8242) function similarly as triggers (140, 150) described above. For instance, a safety trigger (8240) may be first actuated by an operator to permit activation of stapling head assembly (8232). Instrument (1200) further includes a firing trigger (8242), which is similar to firing trigger (150) described above. In particular, once safety trigger (8240) has been activated, firing trigger (8242) is operable to initiate actuation of stapling head assembly (8232). Firing trigger (8242) is configured to engage a motor activation module (not shown) when firing trigger (8242) is advanced by an operator. Like with motor activation module (180) described above, the motor activation module of the present example initiates the stapling sequence by activating a motor (not shown). The motor then drives a cam member (not shown), which in turn drives a cam follower (not shown). The cam member and the cam follower are substantially the same as cam member (700) and cam follower (600) described above, such that the cam member and the cam follower operate cooperatively to drive stapling head assembly (8232) through a stapling sequence.

Unlike instrument (10) described above, instrument (8200) of the present example comprises a shaft rotation knob (8290). Shaft rotation knob (8290) is disposed distally of handle assembly (8210) and is configured to rotate shaft assembly (8220). In particular, shaft rotation knob (8290) permits an operator to rotate shaft assembly (8220) 360° in either a clockwise or counter clockwise direction (as shown in phantom in FIG. 37) about a longitudinal axis extending distally from handle assembly (8210). Although not shown, it should be understood that in some examples all or some of the internal components of shaft assembly (8220) may be rotatable to facilitate rotation of shaft assembly (8220). Of course, shaft rotation knob (8290) is merely optional and may be omitted in some examples. The rotatability of shaft assembly (8220) is not at all required for any of the other teachings herein to apply.

Figure 38:
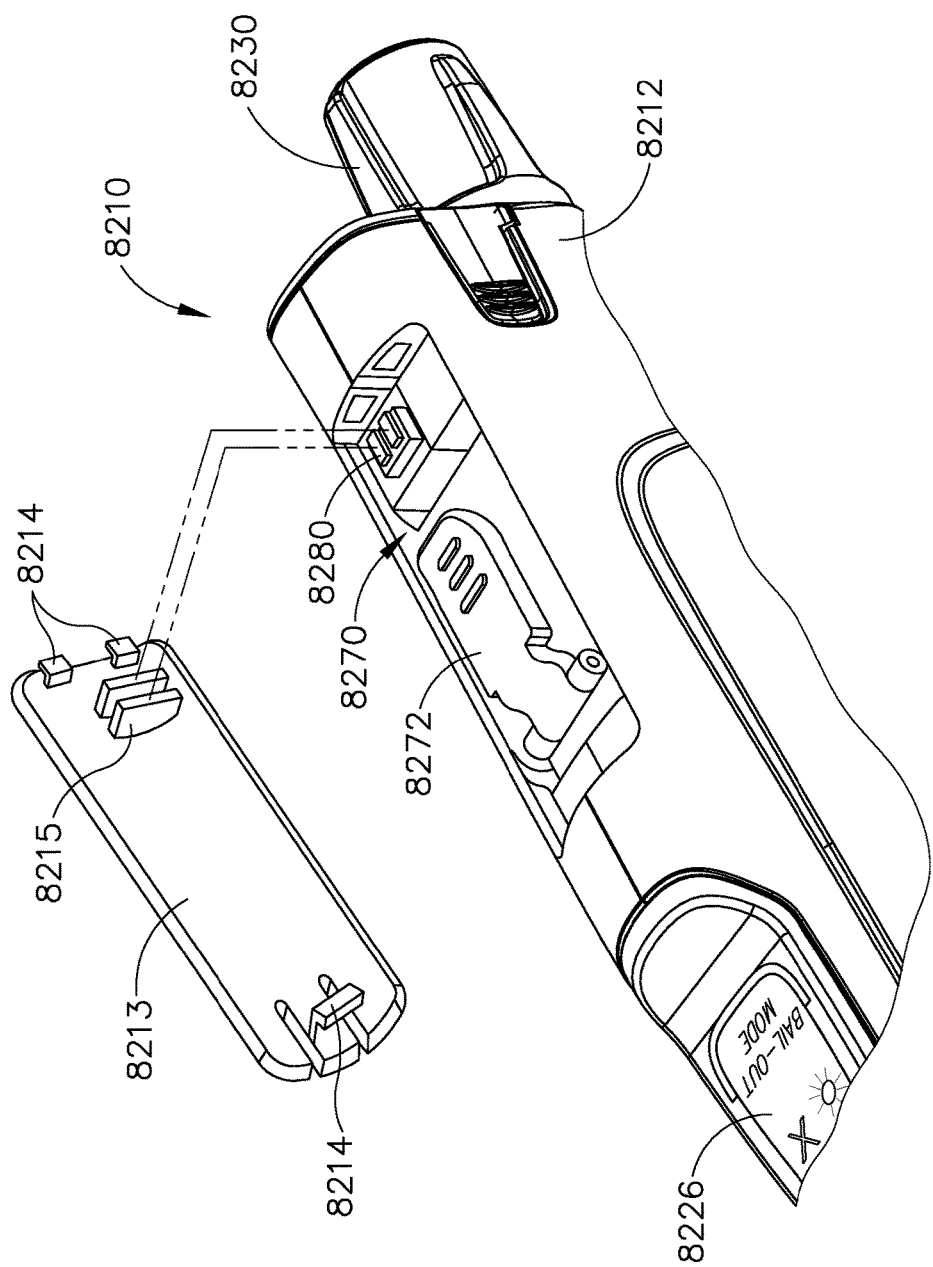
FIG. 38 depicts a detailed perspective view of a proximal portion of the circular stapler of FIG. 37, with the bailout door removed and various bailout features visible.

Also unlike instrument (10) described above, instrument (8200) of the present example comprises a bailout door (8213). Bailout door (8213) comprises a removable portion of casing (8212) and is generally configured to selectively cover certain bailout features (8270) as will be described in greater detail below. As is best seen in FIG. 38, bailout door (8213) comprises a plurality of latch features (8214) and an actuation member (8215). Latch features (8214) are configured to selectively secure bailout door (8213) to handle assembly (8210) through a snap fit. In some examples, latch features (8214) may be resiliently biased or otherwise configured to act as a latch, button, or lever to permit release of bailout door (8213) from handle assembly (8210).

Actuation member (8215) protrudes laterally from bailout door (8213). Actuation member (8215) is generally configured to engage features that are covered by bailout door (8213). In particular, and as will be described in greater detail below, actuation member (8215) is configured to engage a switch (8280) that is disposed inside casing (8212) to signal to instrument (8200) when bailout door (8213) is removed.

As described above, bailout door (8213) is configured to cover bailout features (8270) of instrument (8200). Bailout features (8270) of the present example comprise a release member (8272) and a switch (8280). Release member (8272) is similar to release members (8072, 8172) described above with respect to instruments (8000, 8100). Although not shown, it should be understood that release member (8272) of the present example is in communication with certain bailout mechanisms (not shown). The bailout mechanisms may comprise mechanisms similar to those described above with respect to anvil bailout assembly (8070), anvil bailout assembly (8170), and/or knife bailout assembly (8190) of instruments (8000, 8100) described above. Of course, any other suitable bailout mechanisms may be used as will be apparent to those of ordinary skill in the art in view of the teachings herein.

Switch (8280) is in communication with internal circuitry of instrument (8200). As described above, switch (8280) is configured to be actuated by actuation member (8215) of bailout door (8213). This relationship between switch (8280) and actuation member (8215) permits switch (8280) to communicate to the internal circuitry of instrument (8200) whether bailout door (8213) is attached or removed from handle assembly (8210). Although not shown, it should be understood that the internal circuitry of instrument (8200) may be configured to deactivate motors or other actuators of instrument (8200) upon receiving a signal from switch (8280) that bailout door (8213) has been removed. Thus, switch (8280) is configured to operate as a bailout feature by powering instrument (8200) off when bailout door (8213) is removed. Alternatively, in some examples switch (8280) may activate a reversing sequence that causes instrument (8200) to return to an unactuated state (e.g., the state prior to initiation of a surgical procedure). Of course, some other versions may provide no impact at all on any drive components when switch (8280) is actuated or non-actuated.

Instrument (8200) of the present example further includes an indicator (8216). Indicator (8216) is generally configured to display the status of instrument (8200), including communicating to an operator whether bailout door (8213) has been removed. Indicator (8216) of the present example may be included in addition or in lieu of a window (not shown) similar to window (114) of instrument (10) described above. Indicator (8216) of the present example comprises a liquid crystal display (LCD) screen, although any other suitable mechanism may be used such as light emitting diodes or mechanically driven needle indicators. Indicator (8216) is in communication with switch (828) such that indicator (8216) is configured to provide a visual indication that bailout door (8213) has been removed. In addition or in the alternative, indicator (8216) may provide a visual indication that release member (8272) has been actuated. Various suitable ways in which indicator (8216) may provide one or more indications, and various ways in which indicator (8216) may be triggered to provide such indications, will be apparent to those of ordinary skill in the art in view of the teachings herein.

B. Exemplary Manual Stapling Head Assembly Bailout Feature

Figure 39:
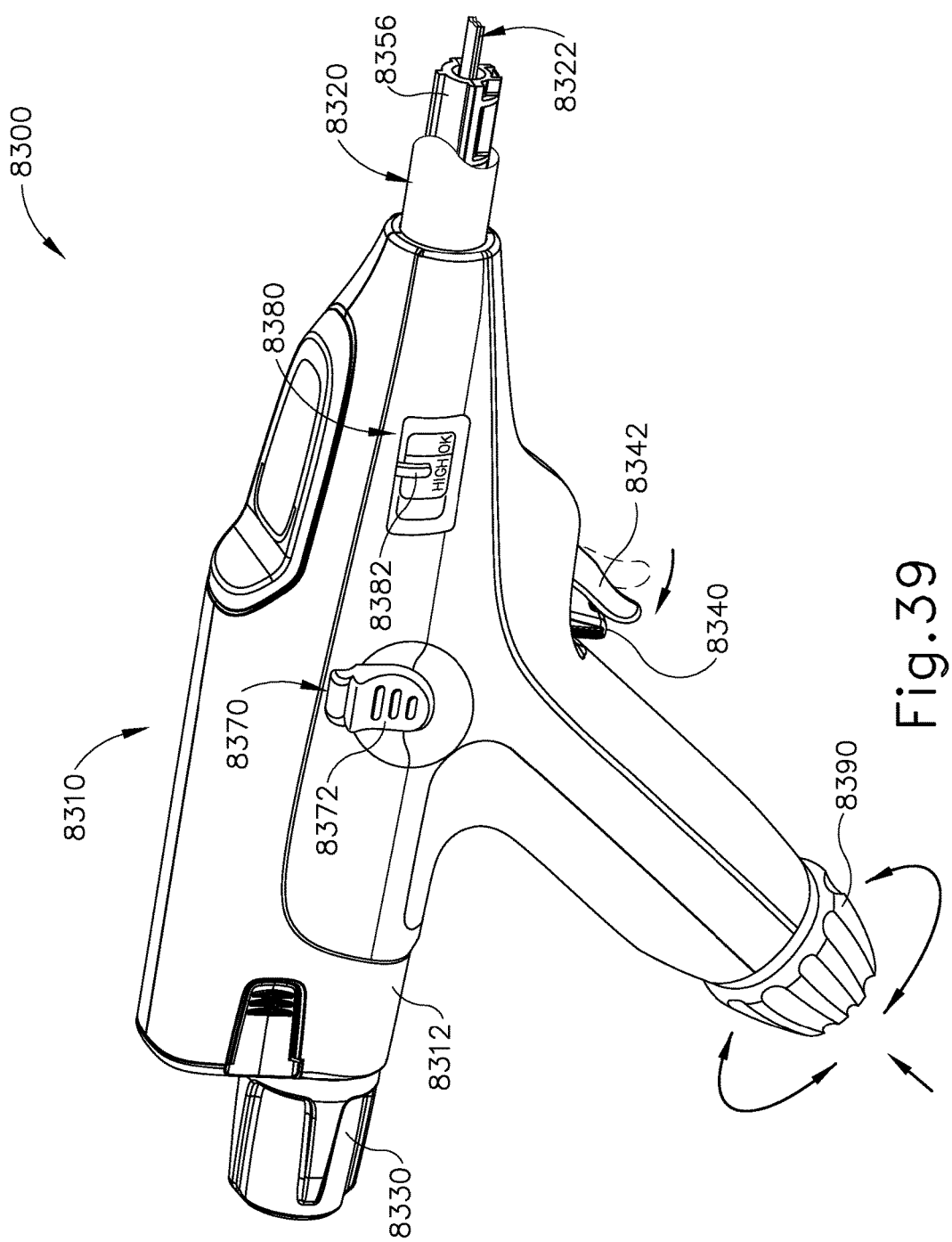
FIG. 39 depicts a detailed perspective view of a handle assembly of yet another exemplary alternative surgical stapler.
Figure 40:
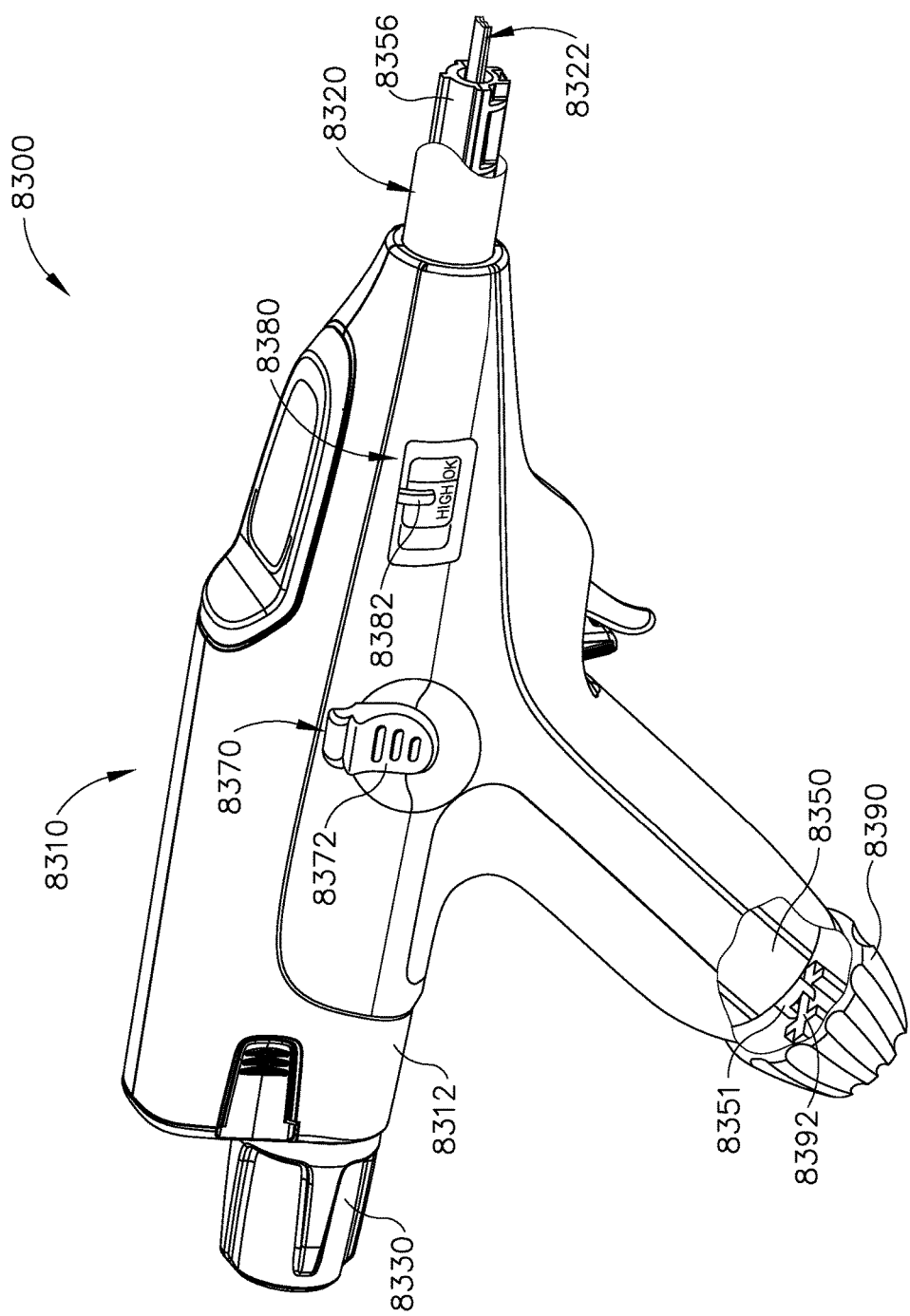
FIG. 40 depicts a detailed perspective cut-away view of the handle assembly of the surgical stapler of FIG. 39, with internal components of a manual stapling head assembly bailout knob visible.

FIGS. 39-40 show yet another exemplary alternative instrument (8300) that may be used to provide an end-to-end anastomosis between two sections of an anatomical lumen such as a portion of a patient's digestive tract. It should be understood that instrument (8300) of the present example is substantially the same as instrument (10) described above unless otherwise noted herein. For instance, like with instrument (10), instrument (8300) comprises a handle assembly (8310), a shaft assembly (8320), a stapling head assembly (not shown), and an anvil (not shown). Handle assembly (8310) comprises as casing (8312) is substantially the same has handle assembly (110) described above such that further details will not be described herein.

Like with instrument (10) described above, instrument (8300) is controlled by an operator via knob (8330) and triggers (8340, 8342). Knob (8330), like with knob (130) described above, is operatively connected to shaft assembly (8320) to actuate the anvil of the stapling head assembly. In particular, knob (8330) is rotatable to engage threads (not shown) of the shaft assembly to translate a trocar actuation rod (8322), which ultimately actuates the anvil as similarly described above with respect to shaft assembly (200) of instrument (10).

Triggers (8340, 8342) function similarly as triggers (140, 150) described above. For instance, a safety trigger (8340) may be first actuated by an operator to permit activation of stapling head assembly (8332). Instrument (8300) further includes a firing trigger (8342), which is similar to firing trigger (150) described above. In particular, once safety trigger (8340) has been activated, firing trigger (8342) is operable to initiate actuation of the stapling head assembly. Firing trigger (8342) is configured to engage a motor activation module (not shown) when firing trigger (8242) is advanced by an operator. Like with motor activation module (180) described above, the motor activation module of the present example initiates the stapling sequence by activating a motor (8350).

Figure 41:
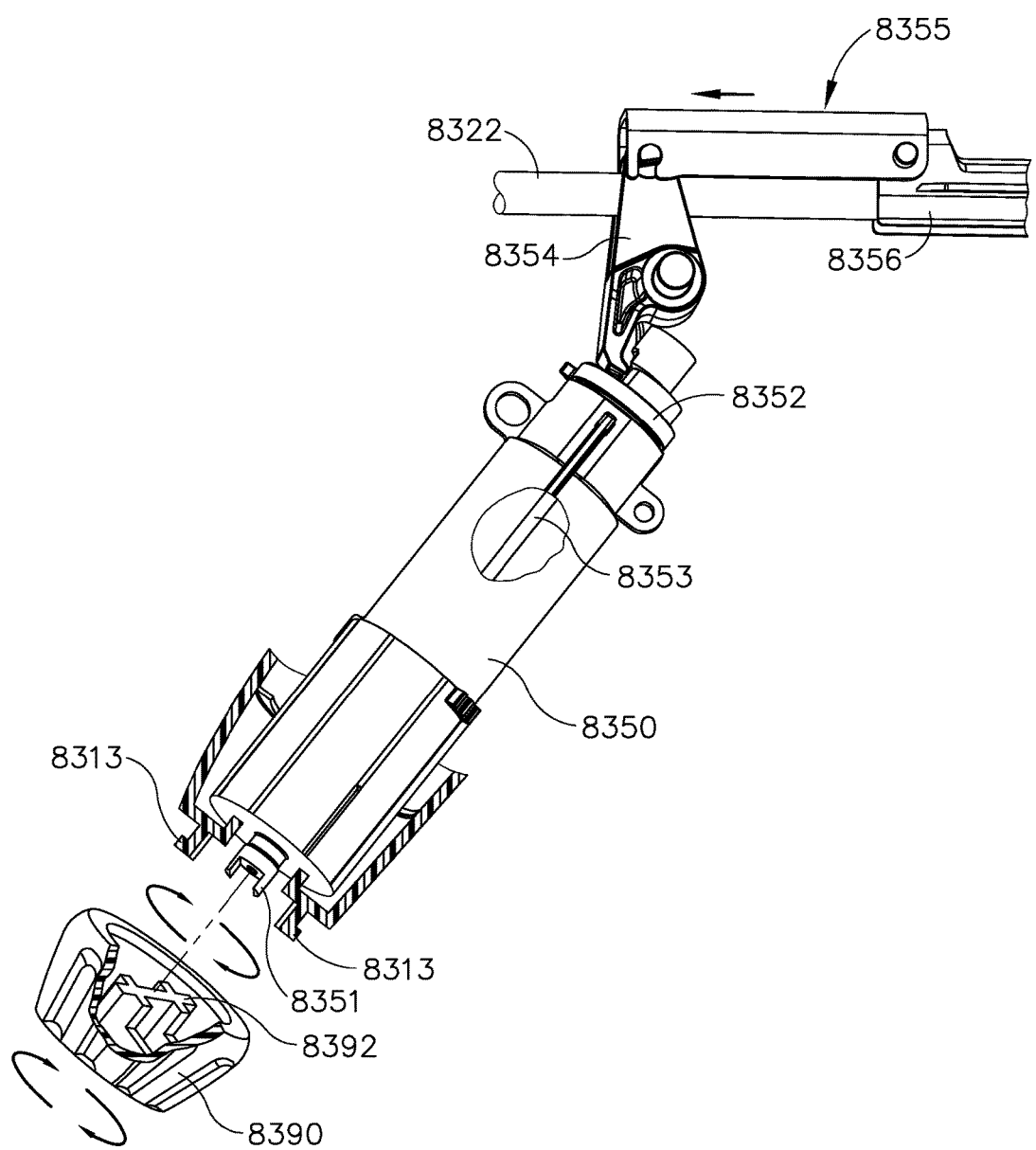
FIG. 41 depicts a detailed side elevational view of a stapling head actuation assembly of the surgical stapler of FIG. 39.

As best seen in FIG. 41, motor (8350) is operable to drive a cam member (8352), which in turn drives a cam follower (8354) to drive a bracket (8355) and stapling head assembly driver (8356) similar to bracket (250) and stapling head assembly driver (240), respectively, described above. Cam member (8352) is substantially the same as cam member (700) described above. Cam follower (8352) is substantially the same as cam follower (600) described above. Bracket (8355) is substantially the same as bracket (250) described above. Stapling head assembly driver (8356) is substantially the same as sapling head assembly driver (240). Thus, the stapling head assembly of instrument (8300) is driven just like stapling head assembly (300) described above.

Unlike instrument (10) described above, instrument (8200) of the present example comprises an anvil bailout assembly (8370) and a side window (8380). Anvil bailout assembly (8370) includes a release member (8372) that is similar to release members (8072, 8172) described above. Although not shown, it should be understood that release member (8372) is in communication with various mechanisms similar to those described above with respect to anvil bailout assemblies (8070, 8170) of instruments (8000, 8100) described above. Thus, anvil bailout assembly (8370) is operable to selectively release the anvil by pivoting release member (8372) like with anvil bailout assemblies (8070, 8170) of instruments (8000, 8100) described above. In other words, bailout assembly (8370) is operable to quickly release tension in trocar actuation rod (8355), thereby quickly releasing any compressive force supplied by the anvil during an anastomosis procedure.

Side window (8380) is similar in function to window (114) described above with respect to instrument (10). However, unlike window (114), side window (8380) is disposed on the side of handle assembly (8310). Although not shown, it should be understood that in some examples side window (8380) may be positioned on both sides of handle assembly (8310) because such positioning may generally promote ease of use. In some versions, side window (8380) includes an indicator (8382) that is operable to indicate a load being applied to instrument (8300). For instance, indicator (8382) may indicate a compressive load being applied to stapling head assembly driver (8356). Various suitable features that may be used to couple indicator (8382) with stapling head assembly driver (8356) to enable indicator (8382) to indicate the load being applied to stapling head assembly driver (8356) will be apparent to those of ordinary skill in the art in view of the teachings herein. As another merely illustrative example, indicator (8382) may indicate a compressive load being applied to trocar actuation rod (8322). Various suitable features that may be used to couple indicator (8382) with trocar actuation rod (8322) to enable indicator (8382) to indicate the load being applied to trocar actuation rod (8322) will be apparent to those of ordinary skill in the art in view of the teachings herein. Similarly, various suitable forms that indicator (8382) may take will be apparent to those of ordinary skill in the art in view of the teachings herein. Alternatively, indicator (8382) may be omitted.

Also unlike instrument (10) described above, instrument (8300) of the present example comprises a manual stapling head assembly bailout knob (8390). Bailout knob (8390) is generally configured to move telescopically and rotate to selectively rotate motor (8350) to thereby actuate stapling head assembly driver (8356) manually. As can be seen in FIGS. 40-41, bailout knob (8390) is configured to selectively communicate with a manual driver (8351) protruding proximally from motor (8350). Manual driver (8351) is in direct communication with a drive shaft (8353) of motor (8350). Thus, when bailout knob (8390) is coupled with driver (8351), rotation of bailout knob (8390) results in corresponding rotation of drive shaft (8353). Otherwise, drive shaft (8353) is driven by motor (8350) during normal operation of instrument (8300).

As described above, bailout knob (8390) is configured to selectively communicate with manual driver (8351) of motor (8350). In particular, casing (8312) of handle assembly (8310) comprises knob attachment features (8313), which are configured to translatably and rotatably fasten bailout knob (8390) to handle assembly (8310). Attachment features (8313) of the present example are spring loaded to resiliently bias a drive feature (8392) of bailout knob (8390) away from manual driver (8351). Thus, bailout knob (8390) is initially positioned by attachment features (8313) such that drive feature (8392) is disengaged from manual driver (8351), such that rotation of bailout knob (8390) has no impact on instrument (8300).

In an exemplary mode of operating bailout knob (8390), an operator may manually retract stapling head assembly driver (8356), thereby manually retracting staple driver member (350) and knife member (340) proximally, by actuating bailout knob (8390). In particular, the operator may first push bailout knob (8390) distally toward motor (8350) to engage drive feature (8392) of bailout knob (8390) with manual driver (8351) of motor (8350). Once drive feature (8392) is engaged with manual driver (8351), the operator may rotate bailout knob (8390) to manually actuate drive shaft (8353). Such rotation in turn drives drive cam member (8352). Cam member (8352) then drives cam follower (8354) to thereby retract bracket (8355) and stapling head assembly driver (8356) proximally. In some instances, the operator may be prompted to actuate bailout knob (8390) in this fashion in response to indicator (8382) indicating that stapling head assembly driver (8356) is experiencing an undesirably high compressive load.

IV. Exemplary Alternative Stapling Head Actuation Assembly

Figure 42:
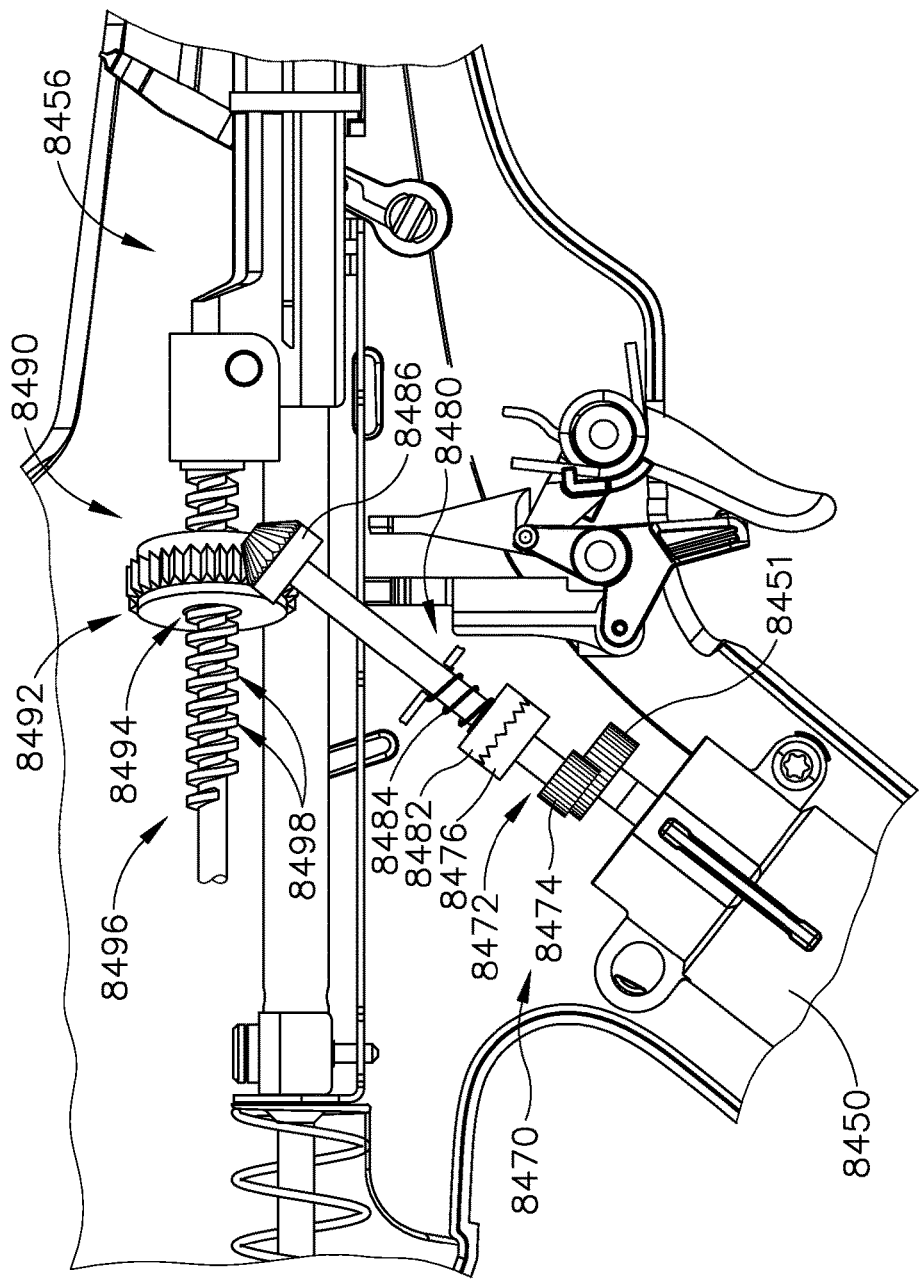
FIG. 42 depicts a detailed side elevational view of an exemplary alternative stapling head actuation assembly that may be readily incorporated into the circular staplers of FIGS. 1, 22, 29, 37 and 39.

FIG. 42 shows an exemplary stapling head actuation assembly (8470) that may be readily incorporated into instruments (10, 8000, 8100, 8200, 8300) described above. It should be understood that stapling head actuation assembly (8470) of the present example may be used in lieu of cam member (700) and cam follower (600) described above with respect to instrument (10). Stapling head actuation assembly (8470) comprises a first drive shaft (8472), a second drive shaft (8480), and a lead screw assembly (8490). First drive shaft (8472) is in communication with a motor (8450) that is similar to motor (160) described above with respect to instrument (10). In particular, motor (8450) includes a motor gear (8451) that meshes with a corresponding drive gear (8474) on first drive shaft (8472). Thus, motor (8450) is configured to drive first drive shaft (8472) via motor gear (8451) and drive gear (8474).

The end of first drive shaft (8472) opposite to drive gear (8474) includes a first slip gear (8476). First slip gear (8476) comprises a crown gear and is configured to mesh with a corresponding second slip gear (8482) of second drive shaft (8480). As will be described in greater detail below, first slip gear (8476) together with second slip gear (8482) are configured to act as a clutch to prevent stapling head actuation assembly (8470) from exerting more than a predetermined amount of force on tissue via a stapling head assembly.

As described above, second drive shaft (8480) comprises second slip gear (8482) that is in communication with first slip gear (8476) of first drive shaft (8472). Like first slip gear (8476), second slip gear (8482) of the present example comprises a crown gear. A resilient member (8484) is disposed adjacent to second slip gear (8482). Resilient member (8484) of the present example is shown as a coil spring, although any suitable resilient mechanism may be used. Resilient member (8484) bears against second slip gear (8482) to urge second slip gear (8482) into engagement with first slip gear (8476). As will be described in greater detail below, this permits first slip gear (8476) and second slip gear (8482) to act as a clutch for motor (8450).

The end of second drive shaft (8480) opposite to second slip gear (8482) includes a bevel gear (8486). Bevel gear (8486) is configured to mesh with a corresponding spur gear (8492) of lead screw assembly (8490). As will be described in greater detail below, bevel gear (8486) generally configured to be driven by second drive shaft (8480) to drive shaft (8480) to drive lead screw assembly (8490). In some alternative versions, gears (8486, 8492) comprise complementary helical gears.

Lead screw assembly (8490) comprises spur gear (8492) and a lead screw member (8496). As described above, spur gear (8492) is configured to mesh with bevel gear (8486) of second drive shaft (8480). Additionally, spur gear (8492) comprises an opening (8494) in spur gear (8492). Opening (8494) is configured to receive lead screw member (8496). The inner diameter of opening (8494) includes a series of threads (not shown). As will be described in greater detail below, the threads of opening (8494) are configured to engage with corresponding threads (8498) of lead screw member (8496) to thereby drive lead screw member (8496), spur gear (8492) serves as a drive nut.

Lead screw member (8496) is generally cylindrical in shape. Lead screw member (8496) further comprises threads (8498) on its outer diameter. The distal end of lead screw member (8496) is rotatably secured to a stapling head assembly driver (8456). As will be described in greater detail below, lead screw member (8496) is generally configured to translate via engagement between threads (8498) of lead screw member and the threads of spur gear (8492) to drive stapling head assembly via stapling head assembly driver (8456).

In an exemplary mode of operation, motor (8451) drives first drive shaft (8472) via gars (8451, 8474). First drive shaft (8472) then drives second drive shaft (8480) via slip gears (8476, 8482). Second drive shaft (8480) then drives lead screw assembly (8490) via bevel gear (8486) and spur gear (8492). In particular, spur gear (8482) is rotated by bevel gear (8486). As spur gear (8482) is rotated, the threads of the inner diameter of opening (8494) in spur gear (8482) engage threads (8498) of lead screw member (8496). Engagement between the threads of opening (8494) and threads (8498) of lead screw member (8496) drive lead screw member (8496) distally. As lead screw assembly (8490) is driven distally, stapling head assembly driver (8456) is correspondingly driven distally to actuate the stapling head assembly.

Figure 44:
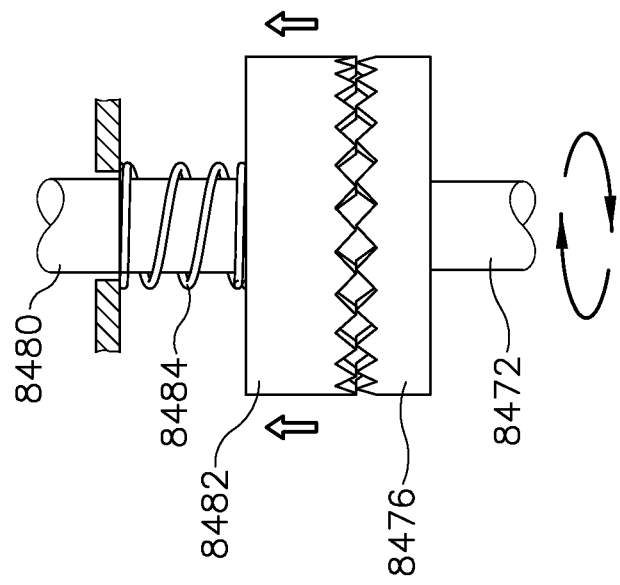
FIG. 44 depicts another detailed side elevational view of the slip clutch of FIG. 43, with the gears slipping to prevent further transfer of torque.
Figure 43:
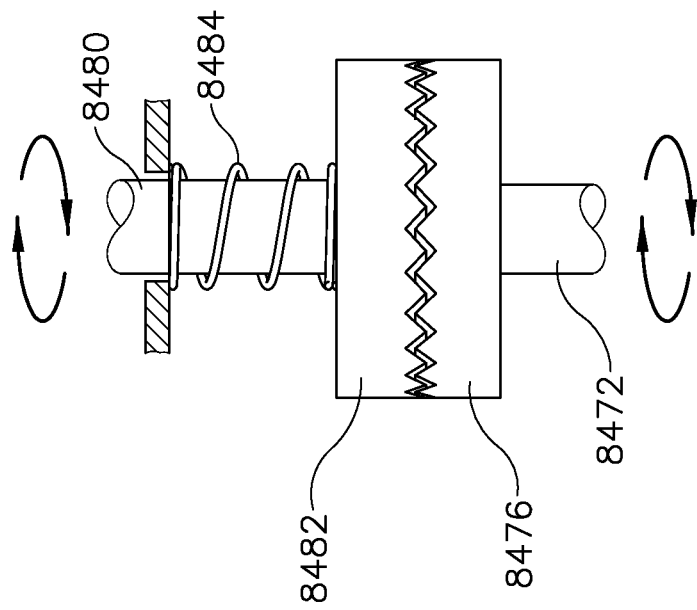
FIG. 43 depicts a detailed side elevational view of a slip clutch the stapling head actuation assembly of FIG. 42, with gears of the slip clutch engaged to transfer torque.

As the stapling head assembly is actuated to drive a knife member and staples through tissue, the torque required to drive lead screw assembly (8490) increases. Generally, slip gears (8476, 8482) are configured to communicate rotation of first drive shaft (8472) to drive second drive shaft (8480) until a predetermined amount of torque is reached. Then slip gears (8476, 8482) will begin to slip relative to each other. As can be seen in FIG. 43, resilient member (8484) of second drive shaft (8480) urges slip gears (8476, 8482) into engagement. However, when the amount of torque required to communicate rotation of first drive shaft (8472) to drive second drive shaft (8480) exceeds a certain threshold, resilient member (8484) will compress and slip gears (8476, 8482) will begin to slip as shown in FIG. 44 such that rotation of first drive shaft (8472) is no longer communicated to drive second drive shaft (8480). Thus, slip gears (8476, 8482) act as a clutching mechanism to restrict the force that may be used to actuate stapling head assembly. Such restriction may be desirable to prevent failure of an anastomosis that might otherwise be at least partially created by the stapling head assembly. In other words, when an unusually high amount of torque is required to actuate the stapling head assembly, this may indicate a problem that may create a risk of a failed anastomosis. It may be better for the outcome of the procedure if the stapling head assembly is not fully actuated under such conditions. The slipping of slip gears may thus provide no anastomosis in lieu of providing a failed or risky anastomosis.

V. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

EXAMPLE 1

A surgical instrument comprising: (a) an anvil; (b) a staple applying assembly, wherein the staple applying assembly comprises: (i) a distal surface defining openings, and (ii) a driver operable to drive an annular array of staples through the openings of the distal surface and into tissue; (c) an adjustment member, wherein the adjustment member is operable to adjust the position of the anvil to thereby vary a gap distance defined between the anvil and the distal surface, wherein the adjustment member comprises: (i) a first section, and (ii) a second section, wherein the first and second sections are configured to cooperate in a state of tension to maintain a selected gap distance between the anvil and the distal surface; (d) a user input feature in communication with the driver, wherein user input feature is operable to actuate the driver to thereby drive the staples; and (e) a bailout assembly in communication with the adjustment member, wherein the bailout assembly is operable to selectively separate the first section of the adjustment member from the second section of the adjustment member to thereby relieve the tension.

EXAMPLE 2

The surgical instrument of Example 1, wherein the adjustment member further comprises a knob.

EXAMPLE 3

The surgical instrument of Example 2, wherein the knob is in communication with the anvil via a rod extending from the anvil to the knob, wherein the first section and the second section of the adjustment member together define the rod.

EXAMPLE 4

The surgical instrument of any one or more of Examples 1 through 3, wherein the first section of the adjustment member has a first threaded portion, wherein the second section has a second threaded portion.

EXAMPLE 5

The surgical instrument of Example 4, wherein the bailout assembly comprises a coupling member, wherein the coupling member includes a first thread set and a second thread set, wherein the first thread set is engaged with the first threaded portion of the adjustment member, wherein the second thread set is engaged with the second threaded portion.

EXAMPLE 6

The surgical instrument of Example 5, wherein the first thread set of the coupling member has a thread pitch orientation that is opposite to a thread pitch orientation of the second thread set of the coupling member.

EXAMPLE 7

The surgical instrument of any one or more of Examples 5 through 6, wherein the coupling member is configured to drive the first and second sections of the adjustment member apart in response to rotation of the coupling member about a longitudinal axis of the adjustment member.

EXAMPLE 8

The surgical instrument of Example 7, wherein the coupling member further comprises a plurality of actuation teeth.

EXAMPLE 9

The surgical instrument of Example 8, wherein the bailout assembly further comprises a pawl member, wherein the pawl member is configured to selectively engage the actuation teeth of the coupling member to thereby rotate the coupling member.

EXAMPLE 10

The surgical instrument of any one or more of Examples 1 through 3, wherein the first section of the adjustment member comprises a female end, wherein the second section of the adjustment member comprises a male end, wherein the male end of the first section is insertable into the female end.

EXAMPLE 11

The surgical instrument of Example 10, wherein the female end of the first section includes a first opening, wherein the male end of the second section includes a second opening, wherein the first opening and the second opening are configured to align when the male end of the second section is inserted into the female end of the first section.

EXAMPLE 12

The surgical instrument of Example 11, wherein the bailout assembly includes a coupling member, wherein the coupling member is insertable through the first opening of the first section and the second opening of the second section.

EXAMPLE 13

The surgical instrument of Example 12, wherein the bailout assembly further comprises an actuator, wherein the actuator is operable to selectively pull the coupling member from the first and second openings to thereby decouple the first section from the second section.

EXAMPLE 14

The surgical instrument of any one or more of Examples 1 through 13, wherein the staple applying assembly further comprises: (i) a knife member, (ii) at least one pin, wherein the at least one pin couples the knife member with the driver such that the driver is operable to drive the knife through tissue in addition to driving staples through tissue, and (iii) a pin removal feature operable to selectively remove the pin to thereby selectively decouple the knife member from the driver.

EXAMPLE 15

The surgical instrument of Example 14, wherein the pin removal feature is operable independently relative to the bailout assembly.

EXAMPLE 16

A surgical instrument comprising: (a) a body assembly, wherein the body assembly comprises: (i) a first actuator and (ii) a second actuator; (b) an elongate shaft assembly, wherein the shaft assembly comprises: (i) a first drive member, wherein the first drive member has an effective length, and (ii) a second drive member; (c) an end effector, wherein the end effector disposed on the distal end of the shaft assembly, wherein the end effector comprises: (i) an anvil, wherein the anvil is in communication with the first drive member, wherein the first actuator is operable to adjust a longitudinal position of the anvil via the first drive member, and (ii) a staple driver, wherein the staple driver is in communication with the second drive member, wherein the second actuator is operable to initiate a firing sequence of the second drive member to fire the staple driver; and (d) an anvil release assembly, wherein the anvil release member is configured to selectively expand the effective length first drive member.

EXAMPLE 17

The surgical instrument of Example 16, wherein the anvil release assembly comprises a release member, wherein the release member is pivotable from a neutral position to a released position, wherein the released position corresponds to the first drive member being in an expanded state.

EXAMPLE 18

The surgical instrument of Example 17, wherein the anvil release assembly further comprises a coupling member, wherein the coupling member extends laterally from the release member, wherein the coupling member is responsive to the release member to selectively decouple at least a portion of the first drive member from being in communication with the anvil.

EXAMPLE 19

The surgical instrument of any one or more of Examples 17 through 18, wherein the anvil release assembly further comprises a coupling member, wherein the coupling member is rotatable relative to the first drive member to selectively expand the first drive member.

EXAMPLE 20

A surgical instrument comprising: (a) an end effector, wherein the end effector is operable to drive a plurality of staples into tissue; (b) a drive assembly comprising a first driver and a second driver, wherein the first driver is operable to adjust the end effector from a first position to a second position, wherein the second driver is operable to actuate the end effector to drive the plurality of staples into tissue; (c) a trigger in communication with the driver, wherein the trigger is operable to actuate the second driver to thereby actuate the end effector; and (e) a release member, wherein the release member is configured to actuate from a first position to a second position, wherein the release member is further configured to return the end effector to the first position in response to actuating the release member from the first position to the second position.

VI. Miscellaneous

It should also be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

At least some of the teachings herein may be readily combined with one or more teachings of U.S. Pat. No. 7,794,475, entitled "Surgical Staples Having Compressible or Crushable Members for Securing Tissue Therein and Stapling Instruments for Deploying the Same," issued Sep. 14, 2010, the disclosure of which is incorporated by reference herein; U.S. Pub. No. 2014/0151429, entitled "Trans-Oral Circular Anvil Introduction System with Dilation Feature," published Jun. 5, 2014, issued as U.S. Pat. No. 9,572,573 on Feb. 21, 2017, the disclosure of which is incorporated by reference herein; U.S. Pub. No. 2014/0144968, entitled "Surgical Staple with Integral Pledget for Tip Deflection," published May 29, 2014, issued as U.S. Pat. No. 9,289,207 on Mar. 22, 2016, the disclosure of which is incorporated by reference herein; U.S. Pub. No. 2014/0158747, entitled "Surgical Stapler with Varying Staple Widths along Different Circumferences," published Jun. 12, 2014, now abandoned, the disclosure of which is incorporated by reference herein; U.S. Pub. No. 2014/0144969, entitled "Pivoting Anvil for Surgical Circular Stapler," published May 29, 2014, issued as U.S. Pat. No. 9,498,222 on Nov. 22, 2016, the disclosure of which is incorporated by reference herein; U.S. Pub. No. 2014/0151430, entitled "Circular Anvil Introduction System with Alignment Feature," published Jun. 5, 2014, issued as U.S. Pat. No. 9,724,100 on Aug. 8, 2017, the disclosure of which is incorporated by reference herein; U.S. Pub. No. 2014/0166717, entitled "Circular Stapler with Selectable Motorized and Manual Control, Including a Control Ring," published Jun. 19, 2014, issued as U.S. Pat. No. 9,532,783 on Jan. 23, 2017, the disclosure of which is incorporated by reference herein; U.S. Pub. No. 2014/0166728, entitled "Motor Driven Rotary Input Circular Stapler with Modular End Effector," published Jun. 19, 2014, issued as U.S. Pat. No. 9,597,081 on Mar. 21, 2017, the disclosure of which is incorporated by reference herein; and/or U.S. Pub. No. 2014/0166718, entitled "Motor Driven Rotary Input Circular Stapler with Lockable Flexible Shaft," published Jun. 19, 2014, issued as U.S. Pat. No. 9,463,022 on Oct. 11, 2016, the disclosure of which is incorporated by reference herein. Various suitable ways in which such teachings may be combined will be apparent to those of ordinary skill in the art.

While the examples herein have been provided in the context of a circular stapling instrument, it should be understood that the various teachings herein may be readily applied to various other kinds of surgical instruments. By way of example only, the various teachings herein may be readily applied to linear stapling devices (e.g., endocutters). For instance, various teachings herein may be readily combined with various teachings of U.S. Pub. No. 2012/0239012, entitled "Motor-Driven Surgical Cutting Instrument with Electric Actuator Directional Control Assembly," published Sep. 20, 2012, issued as U.S. Pat. No. 8,453,914 on Jun 4, 2013, the disclosure of which is incorporated by reference herein, and/or U.S. Pub. No. 2010/0264193, entitled "Surgical Stapling Instrument with An Articulatable End Effector," published Oct. 21, 2010, issued as U.S. Pat. No. 8,408,439, Apr. 2, 2013, the disclosure of which is incorporated by reference herein, as will be apparent to those of ordinary skill in the art. As another merely illustrative example, the various teachings herein may be readily applied to a motorized electrosurgical device. For instance, various teachings herein may be readily combined with various teachings of U.S. Pub. No. 2012/0116379, entitled "Motor Driven Electrosurgical Device with Mechanical and Electrical Feedback," published May 10, 2012, issued as U.S. Pat. No. 9,161,803 on Oct. 20, 2015, the disclosure of which is incorporated by reference herein, as will be apparent to those of ordinary skill in the art. Other suitable kinds of instruments in which the teachings herein may be applied, and various ways in which the teachings herein may be applied to such instruments, will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument comprising:
   (a) an anvil;
   (b) a staple applying assembly, wherein the staple applying assembly comprises:
      (i) a distal surface defining openings, and
      (ii) a driver operable to drive an annular array of staples through the openings of the distal surface and into tissue;
   (c) a rotatable member;
   (d) an adjustment member operatively coupled with the rotatable member, wherein the adjustment member is operable to adjust the position of the anvil to thereby vary a gap distance defined between the anvil and the distal surface, wherein the adjustment member comprises:
      (i) a first section moveably engaged with the rotatable member, and
      (ii) a second section extending distally from the first section, wherein the first section is configured to exert a tension force on the second section in response to rotation of the rotatable member to decrease the gap distance between the anvil and the distal surface; and
   (e) a bailout assembly in communication with the adjustment member, wherein the bailout assembly comprises a coupling member configured to couple the first section of the adjustment member with the second section, wherein the coupling member is operable to transition between:
      (i) a first state in which the coupling member fixes the first section relative to the second section to thereby enable the first section to exert the tension force on the second section, and
      (ii) a second state in which the coupling member permits relative movement between the first section and the second section to thereby relieve at least a portion of the tension force.

2. The surgical instrument of claim 1, wherein the rotatable member comprises a knob, wherein the knob is threadedly coupled with the first section, wherein the first section is operable to translate in response to rotation of the knob.

3. The surgical instrument of claim 2, wherein the adjustment member comprises a rod extending from the anvil to the knob.

4. The surgical instrument of claim 1, wherein the first section of the adjustment member has a first threaded portion, wherein the second section has a second threaded portion.

5. The surgical instrument of claim 4, wherein the coupling member includes a first thread set and a second thread set, wherein the first thread set is engaged with the first threaded portion of the adjustment member, wherein the second thread set is engaged with the second threaded portion.

6. The surgical instrument of claim 5, wherein the first thread set of the coupling member has a thread pitch orientation that is opposite to a thread pitch orientation of the second thread set of the coupling member.

7. The surgical instrument of claim 5, wherein the coupling member is configured to drive the first and second sections of the adjustment member apart in response to rotation of the coupling member about a longitudinal axis of the adjustment member.

8. The surgical instrument of claim 7, wherein the coupling member further comprises a plurality of actuation teeth.

9. The surgical instrument of claim 8, wherein the bailout assembly further comprises a pawl member, wherein the pawl member is configured to selectively engage the actuation teeth of the coupling member to thereby rotate the coupling member.

10. The surgical instrument of claim 4, wherein the first section of the adjustment member comprises a female end, wherein the second section of the adjustment member comprises a male end, wherein the male end of the first section is insertable into the female end.

11. The surgical instrument of claim 10, wherein the female end of the first section includes a first opening, wherein the male end of the second section includes a second opening, wherein the first opening and the second opening are configured to align when the male end of the second section is inserted into the female end of the first section.

12. The surgical instrument of claim 11, wherein the bailout assembly includes a coupling member, wherein the coupling member is insertable through the first opening of the first section and the second opening of the second section.

13. The surgical instrument of claim 12, wherein the bailout assembly further comprises an actuator, wherein the actuator is operable to selectively pull the coupling member from the first and second openings to thereby decouple the first section from the second section.

14. The surgical instrument of claim 1, wherein the staple applying assembly further comprises:
   (i) a knife member,
   (ii) at least one pin, wherein the at least one pin couples the knife member with the driver such that the driver is operable to drive the knife through tissue in addition to driving staples through tissue, and
   (iii) a pin removal feature operable to selectively remove the pin to thereby selectively decouple the knife member from the driver.

15. The surgical instrument of claim 14, wherein the pin removal feature is operable independently relative to the bailout assembly.

16. The surgical instrument of claim 1, wherein the bailout assembly further comprises a release member, wherein the release member is operable to selectively actuate the coupling member between the first state and the second state.

17. A surgical instrument comprising:
   (a) an anvil;
   (b) a staple applying assembly, wherein the staple applying assembly comprises:
      (i) a distal surface defining openings, and
      (ii) a driver operable to drive an annular array of staples through the openings of the distal surface and into tissue;

(c) a rotatable member;

(d) an actuating rod operatively coupled with the rotatable member, wherein the actuating rod is operable to actuate the anvil relative to the staple applying assembly to thereby vary a gap distance defined between the anvil and the distal surface, wherein the actuating rod comprises:

(i) a proximal rod section, and (ii) a distal rod section, wherein the proximal rod section is configured to exert a proximally directed force on the distal rod section in response to rotation of the rotatable member to decrease the gap distance between the anvil and the distal surface; and (e) a bailout assembly in communication with the actuating rod, wherein the bailout assembly is operable to selectively permit the distal rod section to advance distally relative to the proximal rod section to thereby increase the gap distance between the anvil and the distal surface.

18. The surgical instrument of claim 17, wherein the actuating rod extends along a longitudinal axis, wherein the bailout assembly comprises a release member operable to exert a laterally directed force configured to enable a proximal end of the distal rod section to advance distally relative to a distal end of the proximal rod section.

19. A surgical instrument comprising:

(a) an anvil;

(b) a staple applying assembly, wherein the staple applying assembly comprises:

(i) a distal surface defining openings, and (ii) a driver operable to drive an annular array of staples through the openings of the distal surface and into tissue;

(c) a rotatable member;

(d) an actuating member operatively coupled with the rotatable member, wherein the actuating member is operable to actuate the anvil relative to the staple applying assembly in response to rotation of the rotatable member to thereby vary a gap distance defined between the anvil and the distal surface; and (e) a bailout assembly in communication with the actuating member, wherein the bailout assembly is operable to selectively lengthen the actuating member to thereby increase the gap distance between the anvil and the distal surface.

20. The surgical instrument of claim 19, wherein the actuating member comprises a first section and a second section, wherein the bailout assembly is operable to selectively permit the second section to advance longitudinally relative to the first section to lengthen the actuating member.

* * * * *